United States Patent
Ojard et al.

(10) Patent No.: US 11,188,778 B1
(45) Date of Patent: Nov. 30, 2021

(54) EQUALIZATION-BASED IMAGE PROCESSING AND SPATIAL CROSSTALK ATTENUATOR

(71) Applicant: Illumina, Inc., San Diego, CA (US)

(72) Inventors: Eric Jon Ojard, San Francisco, CA (US); Rami Mehio, San Diego, CA (US); Gavin Derek Parnaby, Laguna Niguel, CA (US); Nitin Udpa, San Diego, CA (US); John S. Vieceli, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 17/308,035

(22) Filed: May 4, 2021

Related U.S. Application Data

(60) Provisional application No. 63/020,449, filed on May 5, 2020.

(51) Int. Cl.
*G06K 9/40* (2006.01)
*G06K 9/38* (2006.01)
(Continued)

(52) U.S. Cl.
CPC .................. *G06K 9/40* (2013.01); *G06K 9/38* (2013.01); *G06K 9/4604* (2013.01); *G06K 9/52* (2013.01); *G16B 40/10* (2019.02); *G16B 40/20* (2019.02)

(58) Field of Classification Search
CPC .......... G06K 9/40; G06K 9/38; G06K 9/4604; G06K 9/52; G06T 7/0012–0016; G06T 2207/30004; G16B 40/10; G16B 40/20
See application file for complete search history.

(56) References Cited

U.S. PATENT DOCUMENTS

| 6,598,013 B1 * | 7/2003 | Domnisoru ...... G01N 27/44717 |
| | | 204/456 |
| 6,778,692 B1 * | 8/2004 | Yazici ..................... G06T 5/002 |
| | | 382/132 |

(Continued)

OTHER PUBLICATIONS

Wang et al. "An adaptive decorrelation method removes Illumina DNA base-calling errors caused by crosstalk between adjacent clusters" Scientific Reports vol. 7, Article No. 41348 (2017) (Year: 2017).*

(Continued)

*Primary Examiner* — Sean T Motsinger
(74) *Attorney, Agent, or Firm* — Haynes Beffel & Wolfeld, LLP; Sikander M. Khan

(57) ABSTRACT

The technology disclosed attenuates spatial crosstalk from sequencing images for base calling. In particular, the technology disclosed accesses an image whose pixels depict intensity emissions from a target cluster and intensity emissions from additional adjacent clusters. The pixels include a center pixel that contains a center of the target cluster. Each pixel in the pixels is divisible into a plurality of subpixels. Depending upon a particular subpixel, in a plurality of subpixels of the center pixel, which contains the center of the target cluster, the technology disclosed selects, from a bank of subpixel lookup tables, a subpixel lookup table that corresponds to the particular subpixel. The selected subpixel lookup table contains pixel coefficients that are configured to maximizes a signal-to-noise ratio. The technology disclosed element-wise multiplies the pixel coefficients with the pixels and determines a weighted sum.

20 Claims, 31 Drawing Sheets
(25 of 31 Drawing Sheet(s) Filed in Color)

(51) Int. Cl.
*G16B 40/20* (2019.01)
*G06K 9/52* (2006.01)
*G16B 40/10* (2019.01)
*G06K 9/46* (2006.01)

(56) References Cited

U.S. PATENT DOCUMENTS

| | | | | |
|---|---|---|---|---|
| 10,068,053 | B2 | 9/2018 | Kermani et al. | |
| 2002/0034337 | A1* | 3/2002 | Shekter | G06T 5/002 382/275 |
| 2006/0020203 | A1* | 1/2006 | Tamura | G06T 5/20 600/437 |
| 2007/0194249 | A1* | 8/2007 | Gavrilov | G01J 3/28 250/459.1 |
| 2009/0024331 | A1* | 1/2009 | Tomaney | C12Q 1/6869 702/19 |
| 2010/0034444 | A1* | 2/2010 | Emhoff | G06K 9/00 382/129 |
| 2010/0160172 | A1* | 6/2010 | Erlich | G16B 30/00 506/8 |
| 2011/0256631 | A1* | 10/2011 | Tomaney | C12Q 1/6869 436/94 |
| 2012/0015825 | A1* | 1/2012 | Zhong | G01N 21/6428 506/6 |
| 2013/0109577 | A1* | 5/2013 | Korlach | G01N 27/00 506/4 |
| 2014/0221216 | A1* | 8/2014 | Cope | G16B 15/00 506/1 |
| 2015/0065353 | A1* | 3/2015 | Turner | C12Q 1/6823 506/2 |
| 2015/0079596 | A1* | 3/2015 | Eltoukhy | G06F 16/214 435/6.11 |
| 2015/0169824 | A1* | 6/2015 | Kermani | G16B 30/10 702/19 |
| 2017/0318240 | A1* | 11/2017 | Yu | H04N 5/357 |
| 2018/0195953 | A1* | 7/2018 | Langlois | G16B 30/10 |
| 2018/0260940 | A1* | 9/2018 | Langlois | G06T 5/006 |
| 2020/0350037 | A1* | 11/2020 | Mishra | G16B 35/20 |
| 2020/0364496 | A1* | 11/2020 | Kostem | G16B 40/10 |
| 2020/0364565 | A1* | 11/2020 | Kostem | G06N 3/0481 |
| 2021/0118110 | A1* | 4/2021 | Langlois | G02B 21/0032 |

OTHER PUBLICATIONS

Oxford, Cacho et al., "A comparison of Base-calling Algorithms for Illumina Sequencing Technology", dated Oct. 5, 2015, 10 pages.

Abbaszadegan, "An Encoder-Decoder Based Basecaller for Nanopore DNA Sequencing", dated Feb. 2019, 112pgs.

Xuan Lv et al., "An end-to-end Oxford Nanopore Basecaller Using Convolution-augmented Transformer", dated 2020, 6 pages.

University of Cambridge, "Artificial Intelligence for genomic medicine", dated May 2020, 63 pages.

Genome Analysis Wiki, "Base Caller Summaries", date of last edit Mar. 12, 2010, 4 pages.

Kao et. al., "BayesCall: A model-based base-calling algorithm", dated Apr. 21, 2009, 13 pages.

Zeng et. al, "Causalcall: Nanopore Basecalling Using a Temporal Convolutional Network", dated Jan. 20, 2020, 11 pages.

Ratkovic, Deep Learning Model for Base Calling of MinION Nanopore Reads, dated Mar. 3, 2017, 48 pages, (University of Zagreb).

Boza et al., "DeepNano: Deep recurrent neural network for base calling in MinION nanopore reads", dated Jun. 5, 2017, 13 pages.

Konishi et al., "Halcyon: an accurate basecaller exploiting an encoder-decoder model with monotonic attention", dated Nov. 9, 2020, 7 pages.

Kircher et al., "Improved base calling for the Illumina Genome Analyzer using machine learning strategies", dated Aug. 14, 2009, 9 pages.

Thornley et. al., "Machine Learning in Basecalling—Decoding Trace Peak Behavior", dated Oct. 2006, 9 pages.

Miculinic et. al., "MinCall—MinION end2end convolutional deep learning basecaller", dated Apr. 22, 2019, 8 pages.

Peresini et. al., "Nanopore Base Calling on the Edge", dated Nov. 9, 2020, 15 pages.

Wick et. al., "Performance of neural network basecalling tools for Oxford Nanopore sequencing", dated 2019, 10 pages.

Huang et. al., "SACall: a neural network basecaller for Oxford Nanopore sequencing data based on self-attention mechanism", dated 2020, 10 pages.

Wang et. al., "WaveNano: a signal-level nanopore base caller simultaneous prediction of nucleotide labels and move labels through bi-directional WaveNets", dated 2018, 10 pages.

* cited by examiner

Lookup Tables (LUTs) 106

| LUT | Pixel Coefficients |
|---|---|
| LUT [0] | {a1, ....., a81} |
| LUT [1] | {b1, ....., b81} |
| LUT [2] | {c1, ....., c81} |
| LUT [3] | {d1, ....., d81} |
| LUT [4] | {e1, ....., e81} |
| LUT [5] | {f1, ....., F81} |
| LUT [6] | {g1, ....., g81} |
| LUT [7] | {h1, ....., h81} |
| LUT [8] | {i1, ....., i81} |
| LUT [9] | {j1, ....., j81} |
| LUT [10] | {k1, ....., k81} |
| LUT [11] | {l1, ....., l81} |
| LUT [12] | {m1, ....., m81} |
| LUT [13] | {n1, ....., n81} |
| LUT [14] | {o1, ....., o81} |
| LUT [15] | {p1, ....., p81} |
| LUT [16] | {q1, ....., q81} |
| LUT [17] | {r1, ....., r81} |
| LUT [18] | {s1, ....., s81} |
| LUT [19] | {t1, ....., t81} |
| LUT [20] | {u1, ....., u81} |
| LUT [21] | {v1, ....., v81} |
| LUT [22] | {w1, ....., w81} |
| LUT [23] | {x1, ....., x81} |
| LUT [24] | {y1, ....., y81} |

*Pixel Coefficients for Pixel Patch 300*

LUT [12]

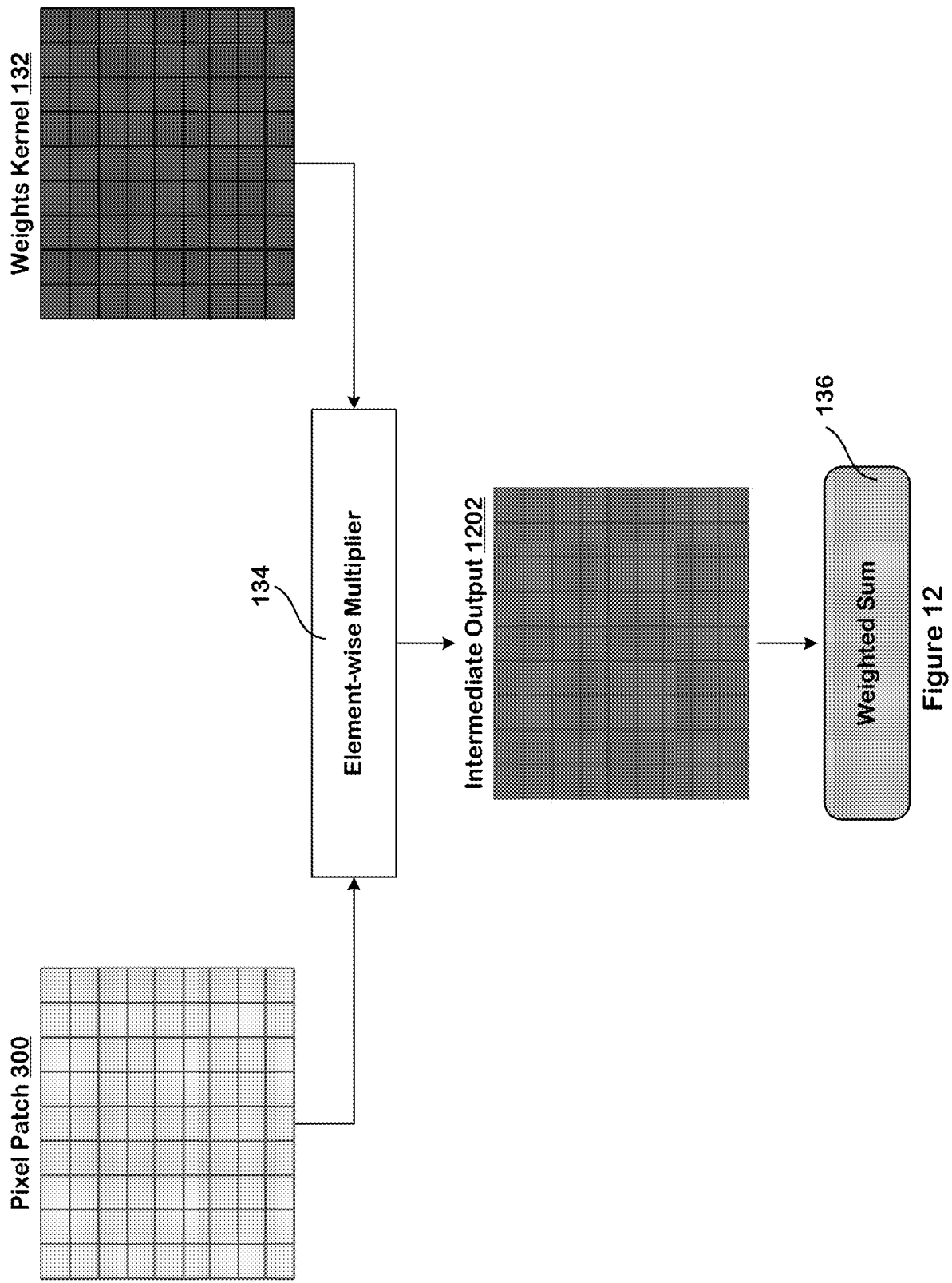

| | | | | | | | |
|---|---|---|---|---|---|---|---|
| 32 | | | | | | | |
| 33 | 0.00E+00 | -5.25E-06 | -4.26E-06 | 9.56E-06 | -2.40E-07 | 4.14E-06 | 2.25E-06 | 1.14E-06 | 7.21E-07 |
| 34 | -4.29E-06 | -1.30E-05 | -1.50E-05 | -1.21E-05 | 4.92E-06 | 6.32E-06 | -3.16E-06 | -1.94E-05 | -1.65E-06 |
| 35 | 9.73E-07 | 7.98E-06 | -5.28E-06 | 1.26E-05 | 1.62E-05 | 3.57E-05 | -1.12E-06 | -1.04E-05 | -1.20E-06 |
| 36 | 5.24E-06 | 8.39E-06 | 2.83E-05 | 1.05E-04 | 2.10E-04 | 1.23E-04 | 1.99E-05 | 3.33E-07 | 2.40E-07 |
| 37 | 3.66E-06 | 2.68E-06 | 1.07E-05 | 1.58E-04 | 3.28E-04 | 1.86E-04 | 2.49E-05 | 1.13E-05 | 4.33E-06 |
| 38 | -3.50E-06 | -4.82E-06 | -4.54E-06 | 5.21E-05 | 1.30E-04 | 8.02E-05 | 1.63E-05 | -5.56E-06 | 7.55E-06 |
| 39 | -4.32E-06 | -6.68E-06 | -1.89E-05 | 7.97E-06 | 2.43E-06 | 2.52E-06 | -2.65E-05 | -1.62E-05 | -5.23E-06 |
| 40 | 5.51E-06 | -9.64E-06 | -1.25E-05 | 4.87E-06 | 1.05E-05 | -7.54E-06 | -1.56E-05 | -1.34E-05 | 3.26E-06 |
| 41 | 2.33E-06 | -1.93E-06 | -8.12E-06 | 8.24E-06 | -3.73E-06 | -4.49E-06 | -9.16E-06 | 3.70E-06 | 3.54E-06 |
| 42 | | | | | | | | |

Weights Kernel 132 — Interpolated Coefficients 1412

Equalizer Primary Analysis Results

| | PhiX Error Rate | | %PF | | %>=Q30 | |
|---|---|---|---|---|---|---|
| Vega Run | Sample | Baseline | Equalizer | Baseline | Equalizer | Baseline | Equalizer |
| 200306_VH00106_26 | Human | 0.367 | 0.346 | 79.2 | 78.9 | 86.0 | 86.9 |
| 200306_VH00112_14 | Human | 0.385 | 0.353 | 80.5 | 80.5 | 85.4 | 86.6 |
| 200306_VH00114_7 | Human | 0.631 | 0.505 | 77.4 | 77.0 | 81.4 | 84.0 |
| 200306_VH00118_12 | Human | 0.403 | 0.365 | 81.2 | 81.1 | 84.5 | 85.6 |

* 10% decrease in error rate on average with no impact to throughput

Figure 19C

EQUALIZATION-BASED IMAGE PROCESSING AND SPATIAL CROSSTALK ATTENUATOR

PRIORITY APPLICATION

This application claims the benefit of U.S. Provisional Patent Application No. 63/020,449, entitled "EQUALIZATION-BASED IMAGE PROCESSING AND SPATIAL CROSSTALK ATTENUATOR," filed May 5, 2020. The provisional application is incorporated by reference for all purposes.

FIELD OF THE TECHNOLOGY DISCLOSED

The technology disclosed relates to apparatus and corresponding methods for the automated analysis of an image or recognition of a pattern. Included herein are systems that transform an image for the purpose of (a) enhancing its visual quality prior to recognition, (b) locating and registering the image relative to a sensor or stored prototype, or reducing the amount of image data by discarding irrelevant data, and (c) measuring significant characteristics of the image. In particular, the technology disclosed relates to removing spatial crosstalk from sensor pixels using equalization-based image processing techniques.

INCORPORATIONS

The following are incorporated by reference for all purposes as if fully set forth herein:

U.S. Nonprovisional patent application Ser. No. 15/936,365, entitled "DETECTION APPARATUS HAVING A MICROFLUOROMETER, A FLUIDIC SYSTEM, AND A FLOW CELL LATCH CLAMP MODULE," filed on Mar. 26, 2018;

U.S. Nonprovisional patent application Ser. No. 16/567,224, entitled "FLOW CELLS AND METHODS RELATED TO SAME," filed on Sep. 11, 2019;

U.S. Nonprovisional patent application Ser. No. 16/439,635, entitled "DEVICE FOR LUMINESCENT IMAGING," filed on Jun. 12, 2019;

U.S. Nonprovisional patent application Ser. No. 15/594,413, entitled "INTEGRATED OPTOELECTRONIC READ HEAD AND FLUIDIC CARTRIDGE USEFUL FOR NUCLEIC ACID SEQUENCING," filed on May 12, 2017;

U.S. Nonprovisional patent application Ser. No. 16/351,193, entitled "ILLUMINATION FOR FLUORESCENCE IMAGING USING OBJECTIVE LENS," filed on Mar. 12, 2019;

U.S. Nonprovisional patent application Ser. No. 12/638,770, entitled "DYNAMIC AUTOFOCUS METHOD AND SYSTEM FOR ASSAY IMAGER," filed on Dec. 15, 2009;

U.S. Nonprovisional patent application Ser. No. 13/783,043, entitled "KINETIC EXCLUSION AMPLIFICATION OF NUCLEIC ACID LIBRARIES," filed on Mar. 1, 2013;

U.S. Nonprovisional patent application Ser. No. 13/006,206, entitled "DATA PROCESSING SYSTEM AND METHODS," filed on Jan. 13, 2011;

U.S. Nonprovisional patent application Ser. No. 14/530,299, entitled "IMAGE ANALYSIS USEFUL FOR PATTERNED OBJECTS," filed on Oct. 31, 2014;

U.S. Nonprovisional patent application Ser. No. 15/153,953, entitled "METHODS AND SYSTEMS FOR ANALYZING IMAGE DATA," filed on Dec. 3, 2014;

U.S. Nonprovisional patent application Ser. No. 14/020,570, entitled "CENTROID MARKERS FOR IMAGE ANALYSIS OF HIGH DENSITY CLUSTERS IN COMPLEX POLYNUCLEOTIDE SEQUENCING," filed on Sep. 6, 2013;

U.S. Nonprovisional patent application Ser. No. 14/530,299, entitled "IMAGE ANALYSIS USEFUL FOR PATTERNED OBJECTS," filed on Oct. 31, 2014;

U.S. Nonprovisional patent application Ser. No. 12/565,341, entitled "METHOD AND SYSTEM FOR DETERMINING THE ACCURACY OF DNA BASE IDENTIFICATIONS," filed on Sep. 23, 2009;

U.S. Nonprovisional patent application Ser. No. 12/295,337, entitled "SYSTEMS AND DEVICES FOR SEQUENCE BY SYNTHESIS ANALYSIS," filed on Mar. 30, 2007;

U.S. Nonprovisional patent application Ser. No. 12/020,739, entitled "IMAGE DATA EFFICIENT GENETIC SEQUENCING METHOD AND SYSTEM," filed on Jan. 28, 2008;

U.S. Nonprovisional patent application Ser. No. 13/833,619, entitled "BIOSENSORS FOR BIOLOGICAL OR CHEMICAL ANALYSIS AND SYSTEMS AND METHODS FOR SAME," filed on Mar. 15, 2013;

U.S. Nonprovisional patent application Ser. No. 15/175,489, entitled "BIOSENSORS FOR BIOLOGICAL OR CHEMICAL ANALYSIS AND METHODS OF MANUFACTURING THE SAME," filed on Jun. 7, 2016;

U.S. Nonprovisional patent application Ser. No. 13/882,088, entitled "MICRODEVICES AND BIOSENSOR CARTRIDGES FOR BIOLOGICAL OR CHEMICAL ANALYSIS AND SYSTEMS AND METHODS FOR THE SAME," filed on Apr. 26, 2013;

U.S. Nonprovisional patent application Ser. No. 13/624,200, entitled "METHODS AND COMPOSITIONS FOR NUCLEIC ACID SEQUENCING," filed on Sep. 21, 2012;

U.S. Provisional Patent Application No. 62/821,602, entitled "Training Data Generation for Artificial Intelligence-Based Sequencing," filed 21 Mar. 2019;

U.S. Provisional Patent Application No. 62/821,618, entitled "Artificial Intelligence-Based Generation of Sequencing Metadata," filed 21 Mar. 2019;

U.S. Provisional Patent Application No. 62/821,681, entitled "Artificial Intelligence-Based Base Calling," filed 21 Mar. 2019;

U.S. Provisional Patent Application No. 62/821,724, entitled "Artificial Intelligence-Based Quality Scoring," filed 21 Mar. 2019;

U.S. Provisional Patent Application No. 62/821,766, entitled "Artificial Intelligence-Based Sequencing," filed 21 Mar. 2019;

NL Application No. 2023310, entitled "Training Data Generation for Artificial Intelligence-Based Sequencing," filed 14 Jun. 2019;

NL Application No. 2023311, entitled "Artificial Intelligence-Based Generation of Sequencing Metadata," filed 14 Jun. 2019;

NL Application No. 2023312, entitled "Artificial Intelligence-Based Base Calling," filed 14 Jun. 2019;

NL Application No. 2023314, entitled "Artificial Intelligence-Based Quality Scoring," filed 14 Jun. 2019; and NL Application No. 2023316, entitled "Artificial Intelligence-Based Sequencing," filed 14 Jun. 2019.

U.S. Nonprovisional patent application Ser. No. 16/825,987, entitled "Training Data Generation for Artificial Intelligence-Based Sequencing," filed 20 Mar. 2020;

U.S. Nonprovisional patent application Ser. No. 16/825,991 entitled "Training Data Generation for Artificial Intelligence-Based Sequencing," filed 20 Mar. 2020;

U.S. Nonprovisional patent application Ser. No. 16/826,126, entitled "Artificial Intelligence-Based Base Calling," filed 20 Mar. 2020;

U.S. Nonprovisional patent application Ser. No. 16/826,134, entitled "Artificial Intelligence-Based Quality Scoring," filed 20 Mar. 2020;

U.S. Nonprovisional patent application Ser. No. 16/826,168, entitled "Artificial Intelligence-Based Sequencing," filed 21 Mar. 2020;

U.S. Provisional Patent Application No. 62/849,091, entitled," Systems and Devices for Characterization and Performance Analysis of Pixel-Based Sequencing," filed May 16, 2019;

U.S. Provisional Patent Application No. 62/849,132, entitled, "Base Calling Using Convolutions," filed May 16, 2019;

U.S. Provisional Patent Application No. 62/849,133, entitled, "Base Calling Using Compact Convolutions," filed May 16, 2019;

U.S. Provisional Patent Application No. 62/979,384, entitled, "Artificial Intelligence-Based Base Calling of Index Sequences," filed Feb. 20, 2020;

U.S. Provisional Patent Application No. 62/979,414, entitled, "Artificial Intelligence-Based Many-To-Many Base Calling," filed Feb. 20, 2020;

U.S. Provisional Patent Application No. 62/979,385, entitled, "Knowledge Distillation-Based Compression of Artificial Intelligence-Based Base Caller," filed Feb. 20, 2020;

U.S. Provisional Patent Application No. 62/979,412, entitled, "Multi-Cycle Cluster Based Real Time Analysis System," filed Feb. 20, 2020;

U.S. Provisional Patent Application No. 62/979,411, entitled, "Data Compression for Artificial Intelligence-Based Base Calling," filed Feb. 20, 2020; and U.S. Provisional Patent Application No. 62/979,399, entitled, "Squeezing Layer for Artificial Intelligence-Based Base Calling," filed Feb. 20, 2020.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Various protocols in biological or chemical research involve performing a large number of controlled reactions on local support surfaces or within predefined reaction chambers. The desired reactions may then be observed or detected, and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis or cyclic-array sequencing. In cyclic-array sequencing, a dense array of DNA features (e.g., template nucleic acids) are sequenced through iterative cycles of enzymatic manipulation. After each cycle, an image may be captured and subsequently analyzed with other images to determine a sequence of the DNA features.

As a more specific example, one known DNA sequencing system uses a pyrosequencing process and includes a chip having a fused fiber-optic faceplate with millions of wells. A single capture bead having clonally amplified sstDNA from a genome of interest is deposited into each well. After the capture beads are deposited into the wells, nucleotides are sequentially added to the wells by flowing a solution containing a specific nucleotide along the faceplate. The environment within the wells is such that if a nucleotide flowing through a particular well complements the DNA strand on the corresponding capture bead, the nucleotide is added to the DNA strand. A colony of DNA strands is called a cluster. Incorporation of the nucleotide into the cluster initiates a process that ultimately generates a chemiluminescent light signal. The system includes a CCD camera that is positioned directly adjacent to the faceplate and is configured to detect the light signals from the DNA clusters in the wells. Subsequent analysis of the images taken throughout the pyrosequencing process can determine a sequence of the genome of interest.

However, the above pyrosequencing system, in addition to other systems, may have certain limitations. For example, the fiber-optic faceplate is acid-etched to make millions of small wells. Although the wells may be approximately spaced apart from each other, it is difficult to know a precise location of a well in relation to other adjacent wells. When the CCD camera is positioned directly adjacent to the faceplate, the wells are not evenly distributed along the pixels of the CCD camera and, as such, the wells are not aligned in a known manner with the pixels. Spatial crosstalk is inter-well crosstalk between the adjacent wells and makes distinguishing true light signals from the well of interest from other unwanted light signals difficult in the subsequent analysis. Also, fluorescent emissions are substantially isotropic. As the density of the analytes increases, it becomes increasingly challenging to manage or account for unwanted light emissions from adjacent analytes (e.g., crosstalk). As a result, data recorded during the sequencing cycles must be carefully analyzed.

Base calling accuracy is crucial for high-throughput DNA sequencing and downstream analysis such as read mapping and genome assembly. Spatial crosstalk between adjacent clusters accounts for a large portion of sequencing errors. Accordingly, an opportunity arises to reduce DNA sequencing errors and improve base calling accuracy by correcting spatial crosstalk in the cluster intensity data.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

FIG. 12 shows the element-wise multiplier element-wise multiplying the interpolated pixel coefficients of the weights kernel with the intensity values of the pixels in the pixel patch and summing intermediate products of the multiplications to produce the output.

Figure 13A:
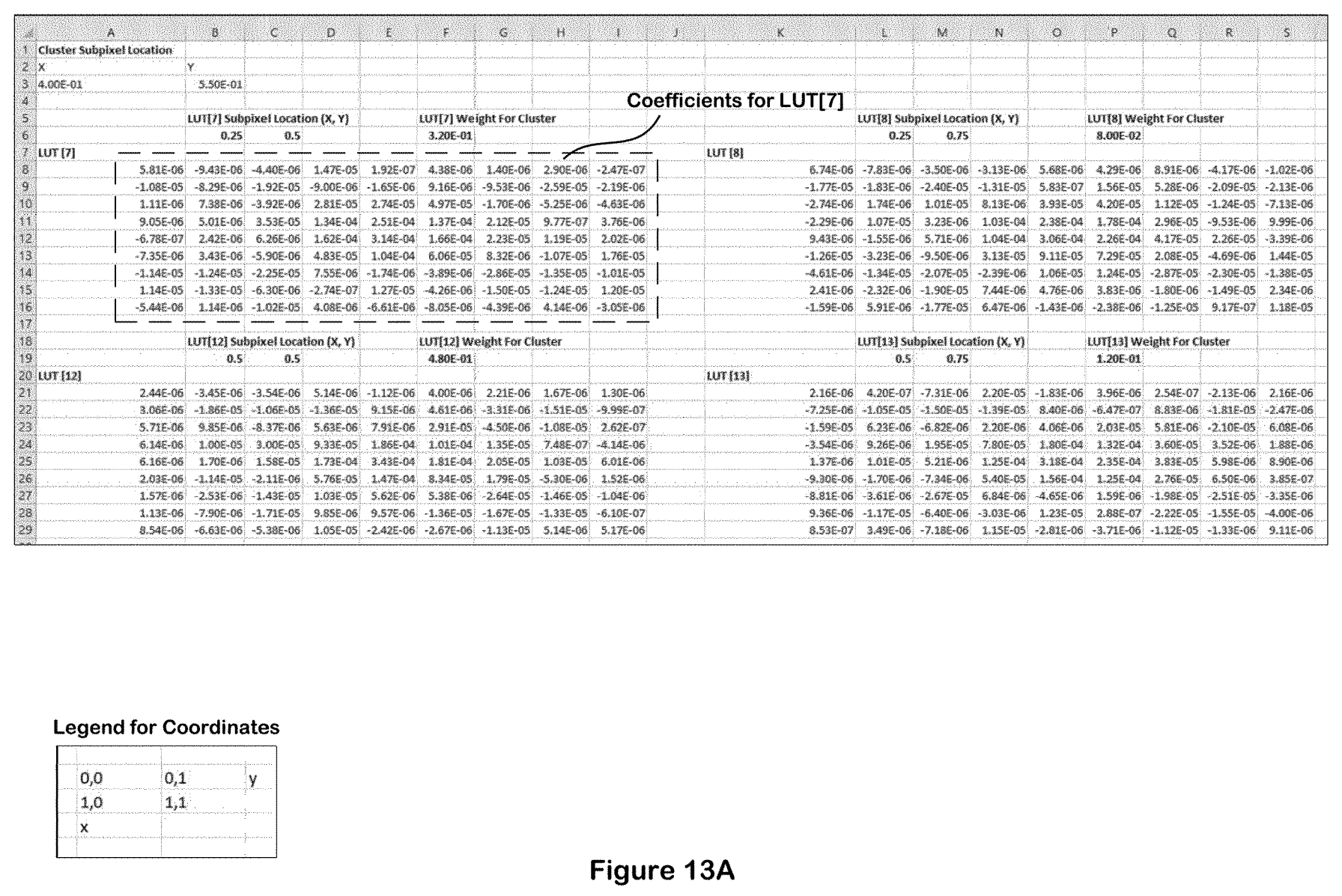
Figure 13D:
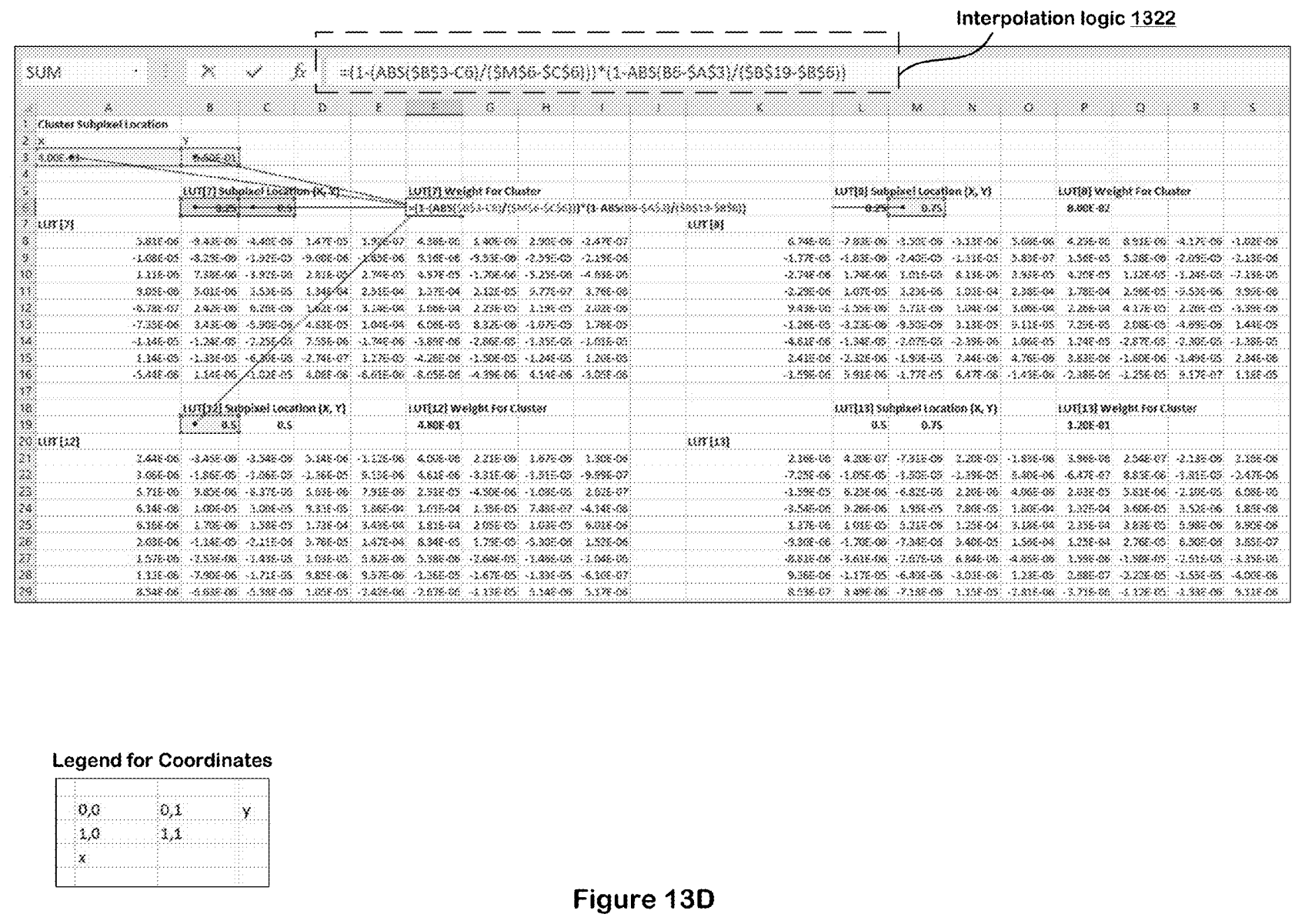
Figure 13F:
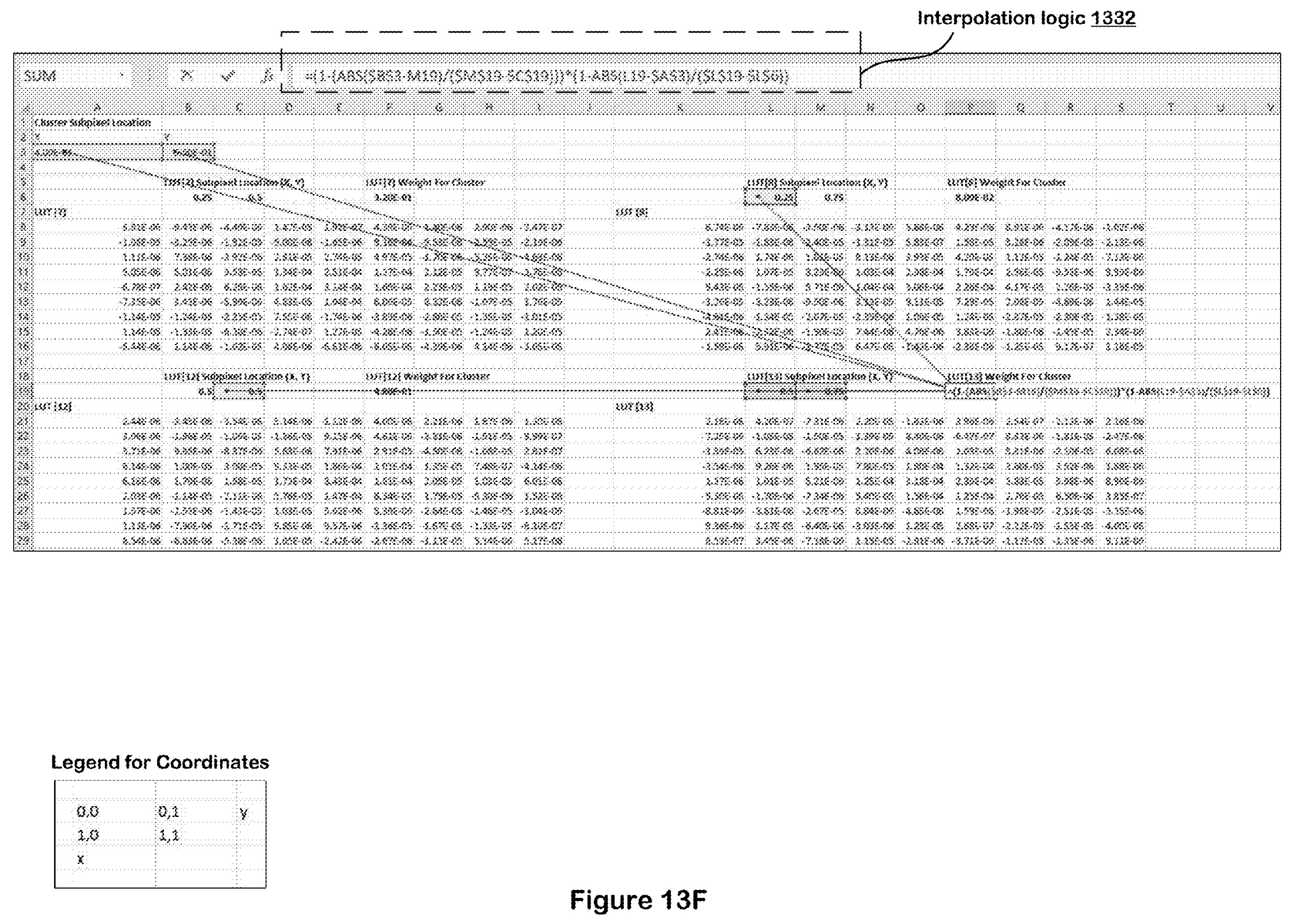

FIGS. 13A, 13B, 13C, 13D, 13E, and 13F show example of coefficients of the LUTs 12, 7, 8, and 13.

FIG. 14A depicts an example of the weights kernel.

FIGS. 15A and 15B demonstrate how the interpolated pixel coefficients of the weights kernel maximize a signal-to-noise ratio and recover an underlying signal of the target cluster 1 from a signal that is corrupted by crosstalk from the clusters 2, 3, 4, and 5.

FIGS. 19A, 19B, 19C, and 19D illustrate various performance metrics of the technology disclosed.

DETAILED DESCRIPTION

The following description will typically be with reference to specific structural implementations and methods. It is to be understood that there is no intention to limit the technology to the specifically disclosed implementations and methods but that the technology may be practiced using other features, elements, methods and implementations. Preferred implementations are described to illustrate the present technology, not to limit its scope, which is defined by the claims. Those of ordinary skill in the art will recognize a variety of equivalent variations on the description that follows.

Lookup Table Generation

Figure 1A:
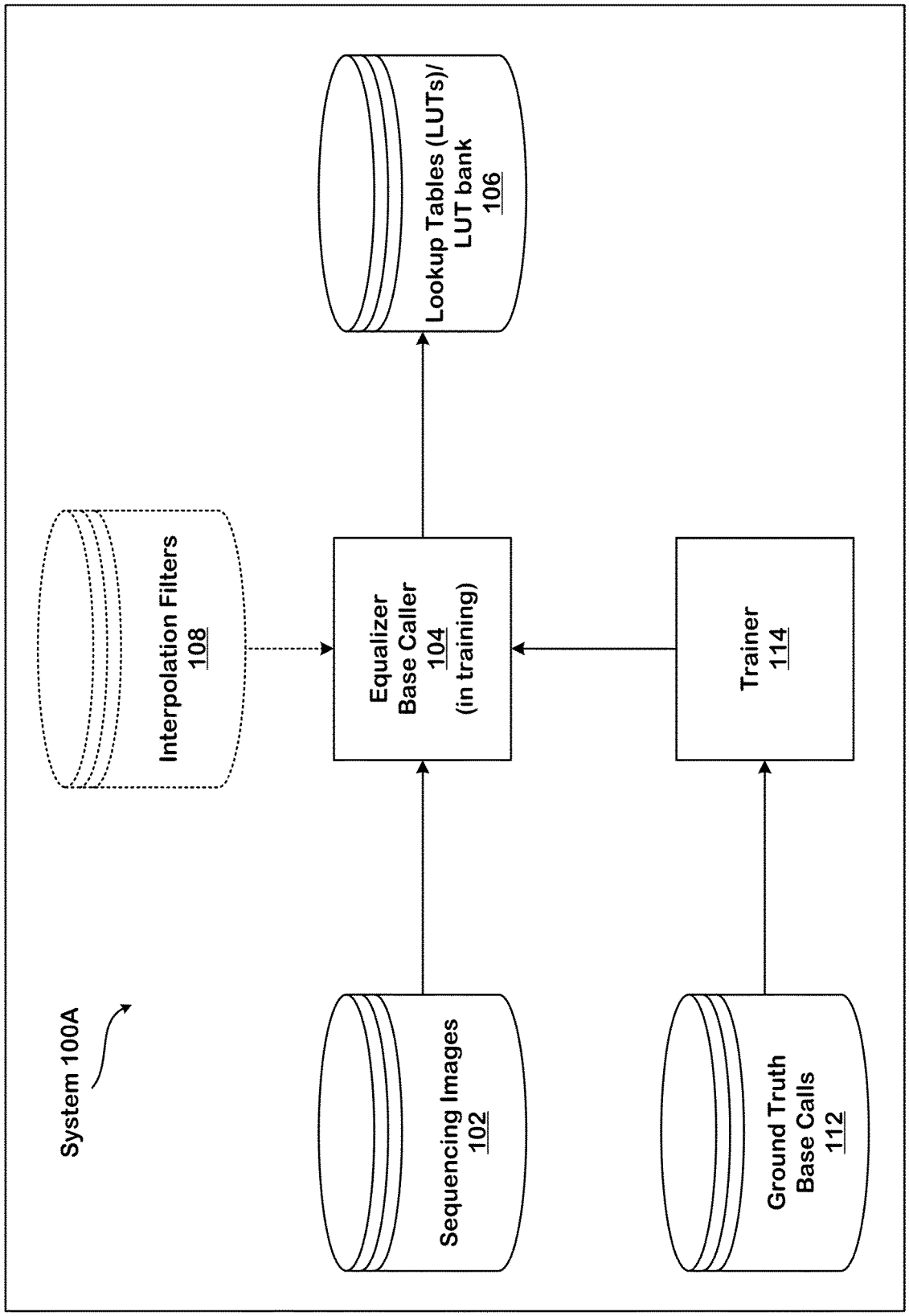
FIG. 1A shows one implementation of generating lookup tables (LUTs)/equalizer filters by training an equalizer.
Figure 1B:
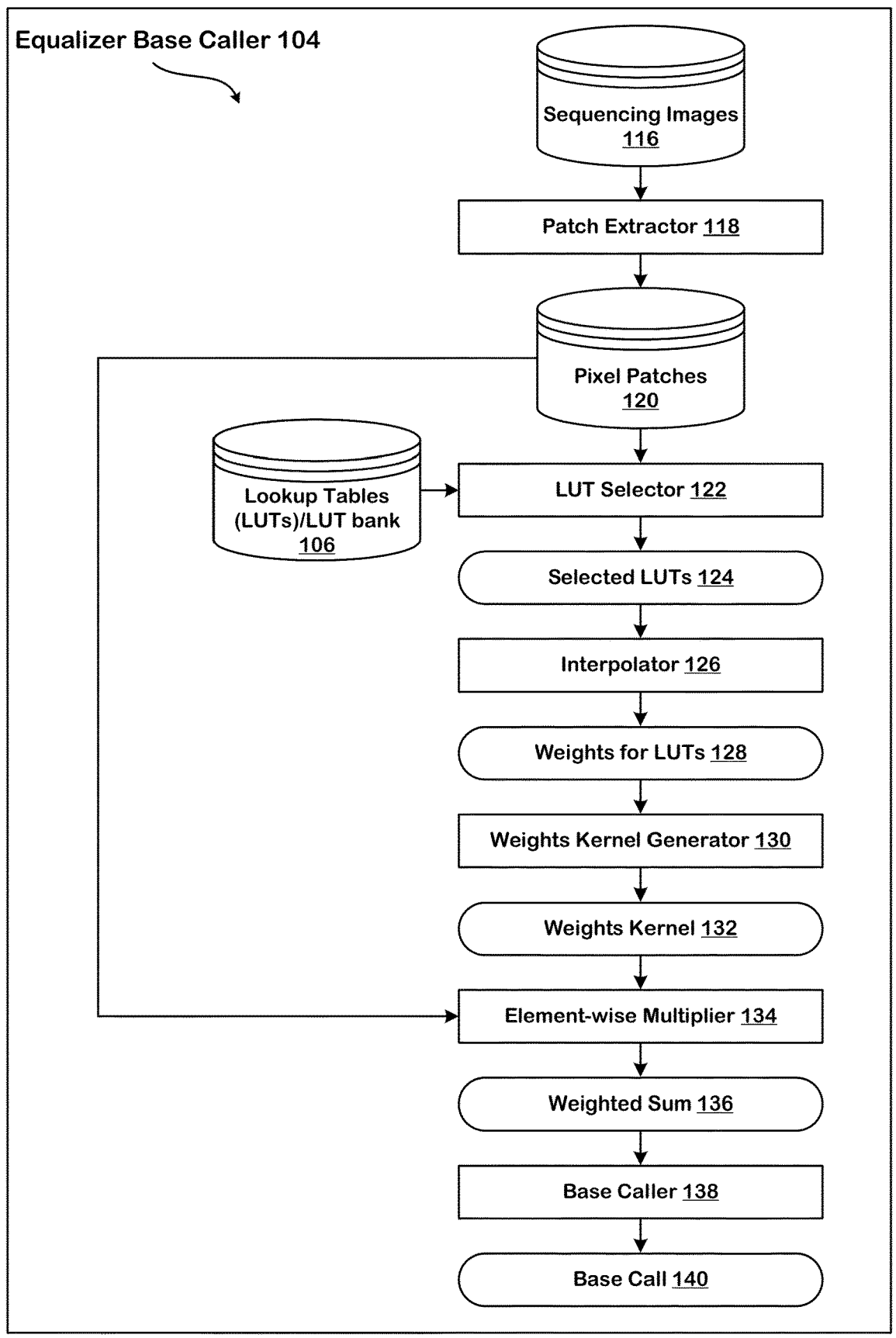
FIG. 1B depicts one implementation of using the LUTs/equalizer filters of FIG. 1 to attenuate spatial crosstalk from sensor pixels and to base call clusters using crosstalk-corrected sensor pixels.

FIG. 1 shows one implementation of generating lookup tables (LUTs) (or LUT bank) 106 by training an equalizer 104. Equalizer 104 is also referred to herein as the equalizer-based base caller 104. System 100A comprises a trainer 114 that trains the equalizer 104 using least square estimation. Additional details about equalizers and least square estimation can be found in the Appendix included with this filing.

Sequencing images 102 are generated during sequencing runs carried out by a sequencing instrument such as Illumina's iSeq, HiSeqX, HiSeq 3000, HiSeq 4000, HiSeq 2500, NovaSeq 6000, NextSeq 550, NextSeq 1000, NextSeq 2000, NextSeqDx, MiSeq, and MiSeqDx. In one implementation, the Illumina sequencers employ cyclic reversible termination (CRT) chemistry for base calling. The process relies on growing nascent strands complementary to template strands with fluorescently-labeled nucleotides, while tracking the emitted signal of each newly added nucleotide. The fluorescently-labeled nucleotides have a 3' removable block that anchors a fluorophore signal of the nucleotide type.

Sequencing occurs in repetitive cycles, each comprising three steps: (a) extension of a nascent strand by adding the fluorescently-labeled nucleotide; (b) excitation of the fluorophore using one or more lasers of an optical system of the sequencing instrument and imaging through different filters of the optical system, yielding the sequencing images; and (c) cleavage of the fluorophore and removal of the 3' block in preparation for the next sequencing cycle. Incorporation and imaging cycles are repeated up to a designated number of sequencing cycles, defining the read length. Using this approach, each cycle interrogates a new position along the template strands.

The tremendous power of the Illumina sequencers stems from their ability to simultaneously execute and sense millions or even billions of analytes (e.g., clusters) undergoing CRT reactions. A cluster comprises approximately one thousand identical copies of a template strand, though clusters vary in size and shape. The clusters are grown from the template strand, prior to the sequencing run, by bridge amplification or exclusion amplification of the input library. The purpose of the amplification and cluster growth is to increase the intensity of the emitted signal since the imaging device cannot reliably sense fluorophore signal of a single strand. However, the physical distance of the strands within a cluster is small, so the imaging device perceives the cluster of strands as a single spot.

Sequencing occurs in a flow cell—a small glass slide that holds the input strands. The flow cell is connected to the optical system, which comprises microscopic imaging, excitation lasers, and fluorescence filters. The flow cell comprises multiple chambers called lanes. The lanes are physically separated from each other and may contain different tagged sequencing libraries, distinguishable without sample cross contamination. In some implementations, the flow cell comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some implementations, the pattern can be an x-y format of features that are in rows and columns. In some implementations, the pattern can be a repeating arrangement of features and/or interstitial regions. In some implementations, the pattern can be a random arrangement of features and/or interstitial regions. Exemplary patterned surfaces that can be used in the methods and compositions set forth herein are described in U.S. Pat. Nos. 8,778,849, 9,079,148, 8,778,848, and US Pub. No. 2014/0243224, each of which is incorporated herein by reference.

In some implementations, the flow cell comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015-002813, each of which is incorporated herein by reference in its entirety). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However, in many implementations, the gel need not be covalently linked to the wells. For example, in some conditions silane free acrylamide (SFA, see, for example, U.S. Pat. No. 8,563,477, which is incorporated herein by reference in its entirety) which is not covalently attached to any part of the structured substrate, can be used as the gel material.

In particular implementations, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is manufacturable, being scalable and utilizing conventional micro- or nano-fabrication methods.

The imaging device of the sequencing instrument (e.g., a solid-state imager such as a charge-coupled device (CCD) or a complementary metal-oxide-semiconductor (CMOS) sensor) takes snapshots at multiple locations along the lanes in a series of non-overlapping regions called tiles. For example, there can be sixty four or ninety six tiles per lane. A tile holds hundreds of thousands to millions of clusters.

The output of the sequencing runs is the sequencing images, each depicting intensity emissions of the clusters and their surrounding background. The sequencing images depict intensity emissions generated as a result of nucleotide incorporation in the sequences during the sequencing. The intensity emissions are from associated analytes/clusters and their surrounding background.

Sequencing images 102 are sourced from a plurality of sequencing instruments, sequencing runs, cycles, flow cells, tiles, wells, and clusters. In one implementation, the sequencing images are processed by the equalizer 104 on an imaging-channel basis. Sequencing runs produce m image(s) per sequencing cycle that correspond to m imaging channels. In one implementation, each imaging channel corresponds to one of a plurality of filter wavelength bands. In another implementation, each imaging channel corresponds to one of a plurality of imaging events at a sequencing cycle. In yet another implementation, each imaging channel corresponds to a combination of illumination with a specific laser and imaging through a specific optical filter. In different implementations such as 4-, 2-, and 1-channel chemistries, m is 4 or 2. In other implementations, m is 1, 3, or greater than 4.

In another implementation, the input data is based on pH changes induced by the release of hydrogen ions during molecule extension. The pH changes are detected and converted to a voltage change that is proportional to the number of bases incorporated (e.g., in the case of Ion Torrent). In yet another implementation, the input data is constructed from nanopore sensing that uses biosensors to measure the disruption in current as an analyte passes through a nanopore or near its aperture while determining the identity of the base. For example, the Oxford Nanopore Technologies (ONT) sequencing is based on the following concept: pass a single strand of DNA (or RNA) through a membrane via a nanopore and apply a voltage difference across the membrane. The nucleotides present in the pore will affect the pore's electrical resistance, so current measurements over time can indicate the sequence of DNA bases passing through the pore. This electrical current signal (the 'squiggle' due to its appearance when plotted) is the raw data gathered by an ONT sequencer. These measurements are stored as 16-bit integer data acquisition (DAC) values, taken at 4 kHz frequency (for example). With a DNA strand velocity of −450 base pairs per second, this gives approximately nine raw observations per base on average. This signal is then processed to identify breaks in the open pore signal corresponding to individual reads. These stretches of raw signal are base called—the process of converting DAC values into a sequence of DNA bases. In some implementations, the input data comprises normalized or scaled DAC values. Additional information about non-image based sequenced data can be found in U.S. Provisional Patent Application No. 62/849,132, entitled, "Base Calling Using Convolutions," filed May 16, 2019, U.S. Provisional Patent Application No. 62/849,133, entitled, "Base Calling Using Compact Convolutions," filed May 16, 2019, and U.S. Nonprovisional patent application Ser. No. 16/826,168, entitled "Artificial Intelligence-Based Sequencing," filed 21 Mar. 2020.

Training

The equalizer 104 generates a LUT bank with a plurality of LUTs (equalizer filters) 106 with subpixel resolution. In one implementation, the number of LUTs 106 generated by the equalizer 104 for the LUT bank depends on the number of subpixels into which a sensor pixel of sequencing images 102 is divided or can be divided. For example, if sensor pixels of the sequencing images 102 is each divisible into n by n subpixels (e.g., 5×5 subpixels), then the equalizer 104 generates $n^2$ LUTs 106 (e.g., 25 LUTs).

In one implementation of the training, data from the sequencing images is binned by well subpixel location. For example, for a 5×5 LUT, $1/25^{th}$ of the wells have a center that is in bin (1,1) (e.g., the upper left corner of a sensor pixel), $1/25^{th}$ of the wells are in bin (1,2), and so on. The equalizer coefficients for each well-center-bin are determined using least squares estimation on the subset of data from the wells that are in each bin. The input to the equalizer 104 is the raw sensory pixels of the sequencing images for those bins. The resulting estimated equalizer coefficients are different per bin.

Each LUT has a plurality of coefficients that are learned from the training. In one implementation, the number of coefficients in a LUT corresponds to the number of sensor pixels that are used for base calling a cluster. For example, if a local grid of sensor pixels (image or pixel patch) that is used to base call a cluster is of size p×p (e.g., 9×9 pixel patch), then each LUT has $p^2$ coefficients (e.g., 81 coefficients).

The training produces equalizer coefficients that are configured to mix/combine intensity values of pixels that depict intensity emissions from a target cluster being base called and intensity emissions from one or more adjacent clusters in a manner that maximizes a signal-to-noise ratio. The signal maximized in the signal-to-noise ratio is the intensity emissions from the target cluster, and the noise minimized in the signal-to-noise ratio is the intensity emissions from the adjacent clusters, i.e., spatial crosstalk, plus some random noise (e.g., to account for background intensity emissions). The equalizer coefficients are used as weights and the mixing/combining includes executing element-wise multiplication between the equalizer coefficients and the intensity values of the pixels to calculate a weighted sum of the intensity values of the pixels.

During training, the equalizer 104 learns to maximize the signal-to-noise ratio by least squares estimation, according to one implementation. Using the least squares estimation, the equalizer 104 is trained to estimate shared equalizer coefficients from the pixel intensities around a subject well and a desired output. Least squares estimation is well suited for this purpose because it outputs coefficients that minimize squared error and take into account the effects of noise amplification.

The desired output is an impulse at the well location (the point source) when the intensity channel is ON and the background level when the intensity channels is OFF. In some implementations, ground truth base calls 112 are used to generate the desired output. In some implementations, the ground truth base calls 112 are modified to account for per-well DC offset, amplification coefficient, degree of polyclonality, and gain offset parameters that are included in the least squares estimate. In one implementation, during the training, a DC offset, i.e., a fixed offset is calculated as part of the least squares estimate. During inference, the DC offset is added as a bias to each equalizer calculation.

In one implementation, the desired output is estimated using Illumina's Real-time Analysis (RTA) base caller, which does not use an equalizer. Details about the RTA can be found in U.S. patent application Ser. No. 13/006,206, which is incorporated by reference as if fully set forth herein. RTA base caller is used to source the ground truth base calls 112 because RTA has a low base calling error rate. The base calling errors get averaged out across many training examples. In another implementation, the ground truth base calls 112 are sourced using aligned genomic data, which has better quality because aligned genomic data can use reference genome and truth information which incorporate the knowledge gained from multiple sequencing platforms and sequencing runs to average out the noise.

The ground truth base calls 112 are base-specific intensity values that reliably represent intensity profiles of bases A, C, G, and T, respectively. A base caller like the RTA base calls clusters by processing the sequencing images 102 and producing, for each base call, color-wise intensity values/outputs. The color-wise intensity values can be considered base-wise intensity values because, depending on the type of chemistry (e.g., 2-color chemistry or 4-color chemistry), the colors map to each of the bases A, C, G, and T. The base with the closest matching intensity profile is called.

Figure 16:
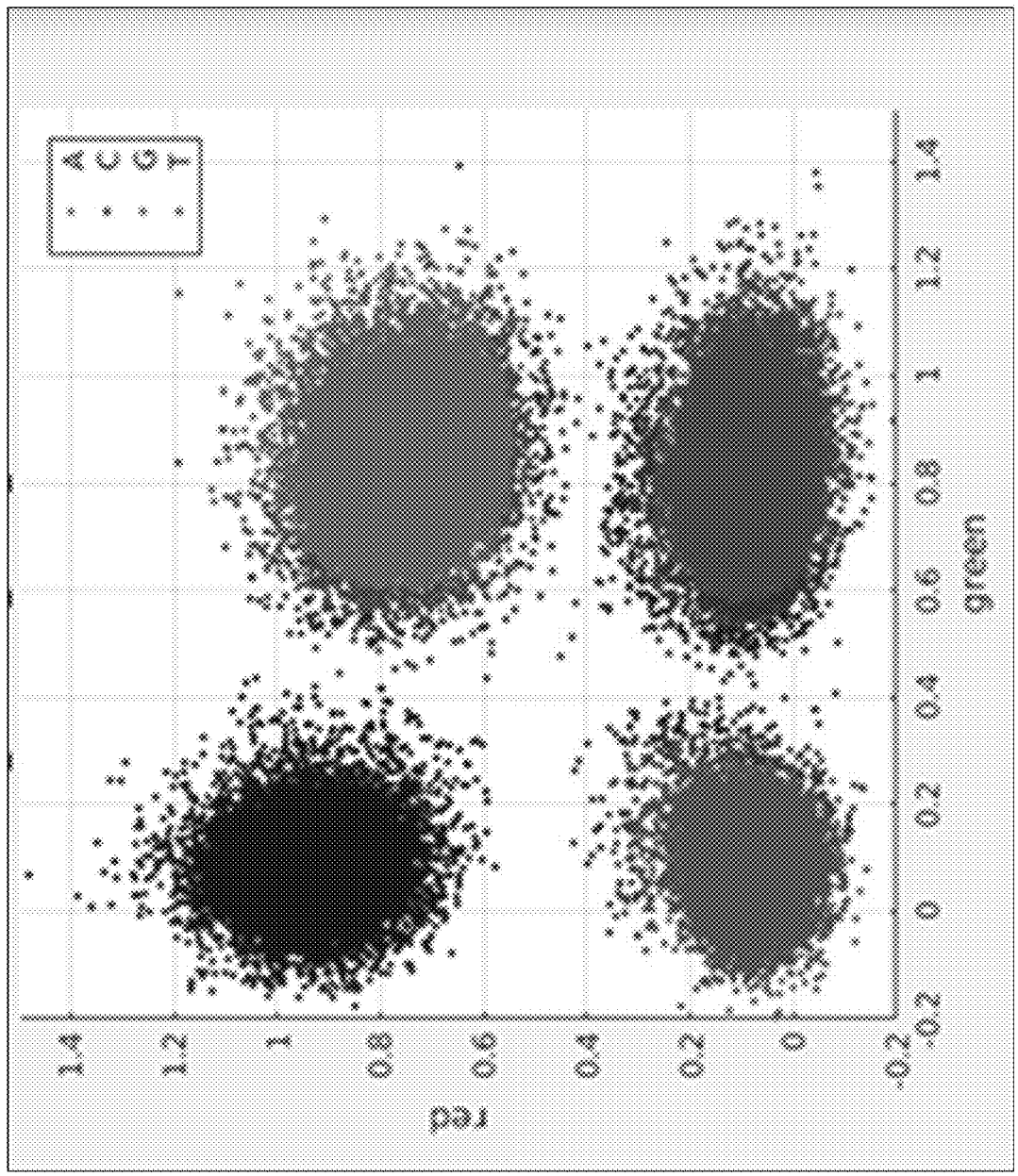
FIG. 16 shows one implementation of base-wise Gaussian fits that contain at their centers base-wise intensity targets which are used as ground truth values for error calculation during training.

FIG. 16 shows one implementation of base-wise Gaussian fits that contain at their centers base-wise intensity targets which are used as ground truth values for error calculation during training. Base-wise intensity outputs produced by the base caller for a multiplicity of base calls in the training data (e.g., tens, hundreds, thousands, or millions of base calls) are used to produce a base-wise intensity distribution. FIG. 16 shows a chart with four Gaussian clouds that are a probabilistic distribution of the base-wise intensity outputs of the bases A, C, G, and T, respectively. Intensity values at the centers of the four Gaussian clouds are used as the ground truth intensity targets given ground truth base calls 112 for the bases A, C, G, and T, respectively, and referred to herein as the intensity targets.

Consider that, during the training, input image data that is fed to the equalizer 104 is annotated with base "A" as the ground truth base call. Then, the target/desired output of the equalizer 104 is the intensity value at the center of the green cloud in FIG. 16, i.e., the intensity target for base A. Similarly, for base "C" ground truth base call, the desired output of the equalizer 104 is the intensity value at the center of the blue cloud in FIG. 16, i.e., the intensity target for base C. Accordingly, targets or desired outputs during the training of the equalizer 104 are the average intensities for the respective bases A, C, G, and T after averaging in the training data. In one implementation, the trainer 114 uses the least squares estimation to fit the coefficients of the equalizer 104 to minimize the equalizer output error to these intensity targets.

In one implementation, during the training, the equalizer 104 applies the coefficients in a given look table (LUT) to pixels of a sequencing image labelled with a given base. This includes element-wise multiplying the coefficients with the intensity values of the pixels and generating a weighted sum of the intensity values, with the coefficients serving/acting/used as the weights. The weighted sum then becomes the predicted output of the equalizer 104. Then, based on a cost/error function (e.g., sum of squared errors (SSE)), an error (e.g., the least square error, the least means squared error) is calculated between the weighted sum and the intensity target determined for the given base (e.g., from the center of the corresponding intensity Gaussian fit as the average intensity observed for the given base). The cost function, such as the SSE, is a differentiable function used to estimate equalizer coefficients using an adaptive approach, and we can therefore evaluate the derivatives of the error with respect to the coefficients, and these derivatives are then used to update the coefficients with values that minimize the error. This process is repeated until the updated coefficients do not reduce the error anymore. In other implementations, batch least squares approach is used to train the equalizer 104.

In other implementations, the base-wise intensity distributions/Gaussian clouds shown in FIG. 16 can be generated on a well-by-well basis and corrected for noise by addition of a DC offset, amplification coefficient, and/or phasing parameter. This way, depending upon the well location of a particular well, the corresponding base-wise Gaussian clouds can be used to generate target intensity values for that particular well.

In one implementation, a bias term is added to the dot product that produces the output of the equalizer 104. During training, the bias parameter can be estimated using a similar approach used to learn the equalizer coefficients, i.e. least squares or least mean squares (LMS). In some implementations, the value for the bias parameter is a constant value equal to one, i.e., a value that does not vary with the input pixel intensities. There is one bias per set of equalizer coefficients. The bias is learned during the training and thereafter fixed for use during inference. The learned bias represents a DC offset that is used in every equalizer calculation during the inference, along with the learned coefficients of each LUT. The bias accounts for random noise caused by different cluster sizes, different background intensities, varying stimulation responses, varying focus, varying sensor sensitivities, and varying lens aberrations.

In yet other decision-directed implementations, the outputs of the equalizer 104 are presumed to be correct for the training purposes.

In another implementation of the training, the equalizer 104 generates only a single LUT (equalizer filter) for a bin, and then uses a plurality of per-bin interpolation filters 108 to generate the remaining equalizer filters for the remaining bins. In this implementation, the sensor pixels around every well for every training example are resampled/interpolated to a well-aligned space (i.e., the wells are centered in their respective pixel patches/local grids). Then, the resampled pixels for every example are consistently aligned across all wells.

However, to apply the single equalizer filter produced by the equalizer 104 in the real online system for base calling, we need to preprocess the raw sensor pixels of the sequencing images to get back to the well-aligned space, i.e., perform interpolation on the raw pixels around each well, with the interpolation parameters varying depending upon the subpixel location of a given well. To avoid this interpolation process, we precompute the overall response for a given well subpixel location. We compute the well-aligned equalizer input values by interpolating the raw pixel intensities to the well-aligned pixel space. We convolve the interpolation response and the equalizer response together to reduce computation. Since the interpolation filter varies by subpixel well location, this gives a different equalizer coefficient set/equalizer filter per subpixel well location, thereby generating the remaining LUTs for the remaining bins. Therefore, in this implementation of the training, coefficients of only the single equalizer filter are trained during the training, but the precompute process generates a bank of LUT-based equalizers by applying the bin-specific interpolation filter 108 in conjunction with the single equalizer filter, where the LUT index is the subpixel well location.

The trainer 114 can train the equalizer 104 and generate the trained coefficients of the LUTs 106 using a plurality of training techniques. Examples of the training techniques include least squares estimation, ordinary least squares, least-mean squares, and recursive least-squares. The least squares technique adjusts the parameters of a function to best fit a data set so that the sum of the squared residuals is minimized. Additional details about the least square estimation algorithm can be found here—Least squares, https://en.wikipedia.org/w/index.php?title=Least_squares&oldid=951737821 (last visited Apr. 28, 2020), which is incorporated by reference as if fully set forth herein. Ordinary least squares is a type of the least squares method for estimation in a linear regression model. Additional details about the ordinary least squares algorithm can be found here—Ordinary least squares, https://en.wikipedia.org/w/index.php?title=Ordinary_least_squares&oldid=951770366 (last visited Apr. 28, 2020), which is incorporated by reference as if fully set forth herein. In other implementations, other estimation algorithms and adaptive equalization algorithms can be used to train the equalizer 104.

The equalizer 104 can be trained in an offline mode. In the offline mode, according to one implementation, the trained coefficients of the LUTs 106 are generated using the following batch least squares equalization logic:

$$\beta = (X^T X)^{-1} X^T y.$$

In the equation above, the LUT coefficients are beta hat, the pixel intensities are X, the targets are y. A DC term is also added to the pixel intensities and the coefficients (e.g., an extra intensity term that is fixed at 1 for all cases). Then, as an example, consider that X is a matrix of size 82 (=9×9 input intensities plus constant DC term)×the number of training examples in the batch, Y is a target output for every training example, i.e., each value is the intensity center of an ON/OFF cloud depending upon the training example truth. Beta hat is then the set of coefficients that minimizes the sum of the squared residuals and is also of size 82 (=9×9 coefficients plus 1 DC term).

The equalizer 104 can also be trained in an online mode to adapt the coefficients of the LUTs 106 to track changes in the temperature (e.g., optical distortion), focus, chemistry, machine-specific variation etc. on a tile-by-tile or sub-tile basis while the sequencer is running and the sequencing run is cyclically progressing. In the online mode, the trained coefficients of the LUTs 106 are generated using adaptive equalization. The online mode uses the least-mean squares as the training algorithm, which is a form of stochastic gradient descent. Additional details about the least-mean squares algorithm can be found here—Least mean squares filter, https://en.wikipedia.org/w/index.php?title=Least mean squares filter&oldid=941899198 (last visited Apr. 28, 2020), which is incorporated by reference as if fully set forth herein.

The least-mean squares technique uses the gradient of the squared error with respect to each coefficient, to move the coefficients in a direction that minimizes the cost function which is the expected value of the squared error. This has a very low computational cost—only a multiply and accumulate operation per coefficient is executed. No long-term storage is needed, except for the coefficients. The least-mean squares technique is well suited to for processing huge amounts of data (e.g., processing data from billions of clusters in parallel). Extensions of the least-mean squares technique include normalized least-mean-square and frequency-domain least-mean-square, which can also be used herein. In some implementations, the least-mean squares technique can be applied in a decision-directed fashion in which we assume that our decisions are correct, i.e., our error rate is very low and small mu values will filter out any disturbed updates due to incorrect base calls.

Figure 18:
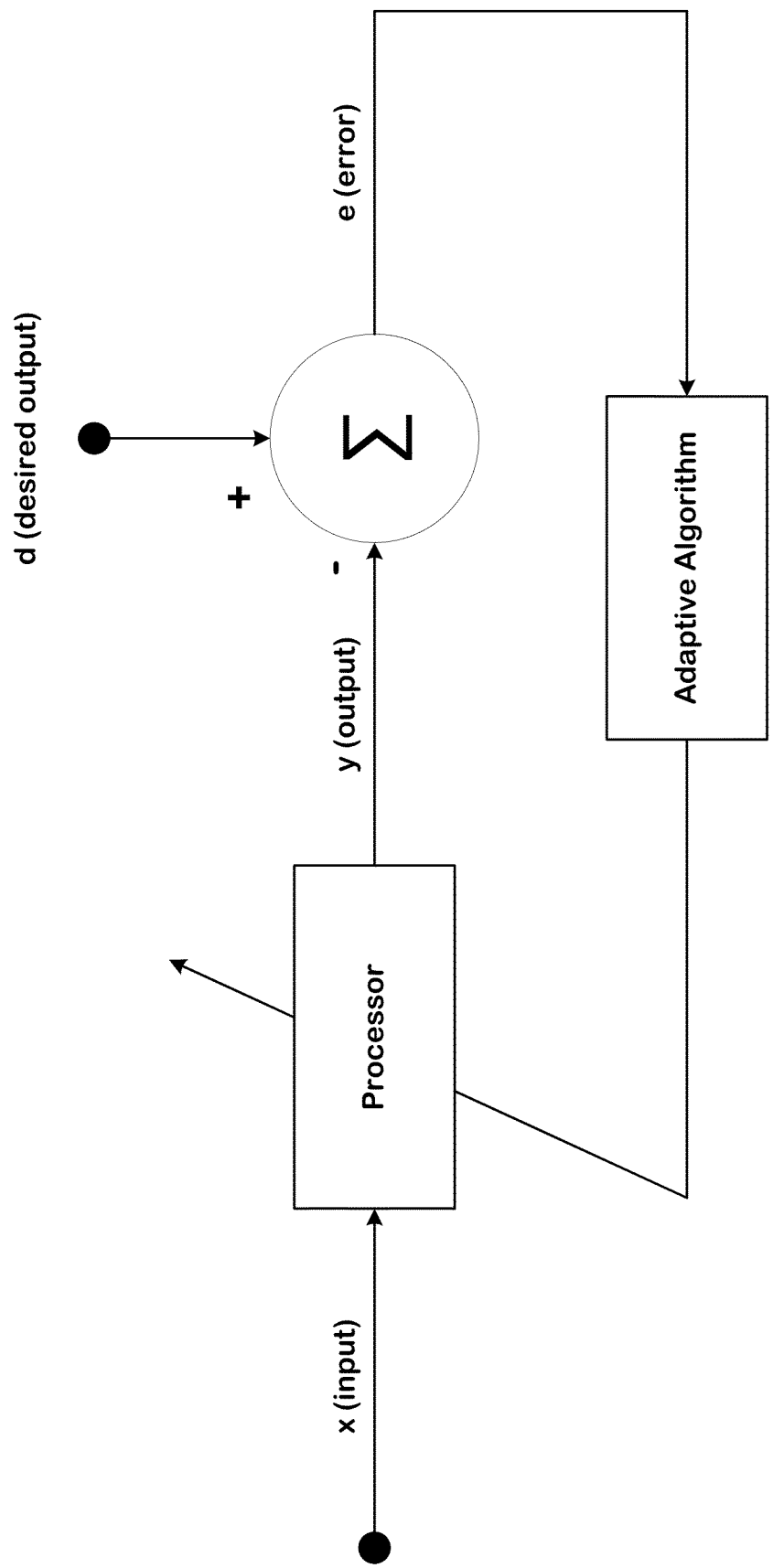
FIG. 18 shows one implementation of an adaptive equalization technique that can be used to train the equalizer.

FIG. 18 shows one implementation of an adaptive equalization technique that can be used to train the equalizer 104. Here, the equalization logic is y=x·h+d, where x is the input pixel intensities, h is the equalizer coefficients, d is the DC offset. In one implementation, x and h are row and column vectors respectively, with length 81. This vector model is equivalent to a dot product of 9×9 matrices representing input pixels and coefficients. The cost is the expected value of error squared. The gradient update moves each coefficient in a direction that reduces the expected value of error squared. This leads to the following update:

$$\hat{h}(n+1) = \hat{h}(n) - \frac{\mu}{2}\nabla C(n) = \hat{h}(n) + \mu E\{x(n)e^*(n)\}$$

For most systems the expectation function $E\{x(n)e^*(n)\}$ must be approximated. This can be done with the following unbiased estimator $$\hat{E}\{x(n)e^*(n)\} = \frac{1}{N}\sum_{i=0}^{N-1} x(n-i)e^*(n-i)$$

where N indicates the number of samples we use for that estimate. The simplest case is N=1

$$\hat{E}\{x(n)e^*(n)\} = x(n)e^*(n)$$

For that simple case the update algorithm follows as $$\hat{h}(n+1) = \hat{h}(n) + \mu x(n)e^*(n)$$

Indeed, this constitutes the update algorithm for the LMS filter.

In equations above, h is a vector of equalizer coefficients (e.g., 9×9 equalizer coefficients), x is a vector of equalizer input intensities (e.g., 9×9 pixels in a pixel patch), and e is the error for the equalizer calculation that was performed using the 81 values in x, i.e., only 1 error term per equalizer output.

Applying this update generates a new estimate of the 9×9 equalizer coefficients that moves them in a direction that (on average) reduces the mean squared error (MSE). There are 81 updates, one for each equalizer coefficient. In some implementations, Mu is a small constant used to change the adaptation rate/convergence speed. A DC term update can be calculated in a similar way. A gain term update also can be calculated in a similar way.

A coefficient set can be shared between, e.g., a tile, a region of a tile, or a flow cell surface. This is done by saving and restoring coefficient sets as the input data is changed.

In some implementations, since linear interpolation is applied on the coefficient sets, the updates are applied slightly differently in the following manner:

$$h(q,n+1) = h(q,n) + \text{lambda\_q} \cdot \mu \cdot x(n) \cdot e(n)$$

In the equation above, h(q, n) is weight q at cycle n, lambda_q is the linear interpolation weight for a particular set of coefficients and can include four updates per equalizer output due to linear interpolation in two dimensions.

The recursive least-squares technique extends the least squares technique to a recursive algorithm. Additional details about the recursive least-squares algorithm can be found here—Recursive least squares filter, https://en.wikipedia.org/w/index.php?title=Recursive_least_squares_filter&oldid=916406502 (last visited Apr. 28, 2020), which is incorporated by reference as if fully set forth herein.

In a multi-domain implementation, the LUTs 106 and their trained coefficients can be generated along a plurality of domains. Examples of the domains include sequencers or sequencing instruments/machines (e.g., Illumina's NextSeq, MiSeq, HiSeq and their respective models), sequencing protocols and chemistries (e.g., bride amplification, exclusion amplification), sequencing runs (e.g., forward and reverse direction), sequencing illumination (e.g., structured, unstructured, angled), sequencing equipment (e.g., overhead CCD cameras, underlying CMOS sensors, one lasers, multiple lasers), imaging techniques (one-channel, two-channel, four-channel), flow cells (e.g., patterned, unpatterned, embedded on a CMOS chip, underlying CCD cameras), and spatial resolutions on a flow cell (e.g., at different regions or quadrants within the flow cell (e.g., different tiles on the flow cell (e.g., for edge wells that are on tiles closer to lasers or cameras or the fluidic system)) and at different regions within a tile (e.g., different lanes on a tile (e.g., for edge wells that are on lanes closer to lasers or cameras or the fluidic system)). Those skilled in the art will appreciate that other selectable domains and parameters typically associated with sequencing are similarly included (e.g., image processing algorithm, image registering algorithm, ground truth annotation schemes (e.g., continuous labels like intensity values, hard labels like one-hot encodings, soft labels like softmax scores), temperature, focus, lens, sequencing reagents, sequencing buffers).

Sequencing images generated using respective ones of the domains can be used to create discrete and different training sets for the respective domains. The discrete training sets can be used to train the equalizer 104 to generate LUTs with trained coefficients for corresponding domains. The trained coefficients specifically trained generated for respective domains in a plurality of the domains can be stored and accessed accordingly during the online mode depending upon which domain or combination of the domains is at use in the current or ongoing sequencing operation. For example, for the sequencing operation, a first coefficient set that is more suitable for edge wells of a flow cell can be used, along with a second coefficient set that is more suitable for center wells of the same flow cell.

In one implementation, a configuration file can specify different combinations of the domains and can be analyzed during the online mode to select different sets of coefficients that are specific to the domains identified by the configuration file.

In a multi-training implementation, the equalizer 104 is subjected to pre-training as well as training. That is, the LUTs 106 and their coefficients are first trained during a pre-training stage using a first training technique and then retrained or further trained during a further training stage using a second training technique. The first and second training techniques can be any of the training techniques listed above. The first and the second training techniques can be same, or they can be different. For example, the pre-training stage can be the offline mode that uses the batch ordinary least squares training technique, and the training stage can be the online mode that uses the iteratively stochastic least-mean squares technique.

In some implementations, the multi-domain and the multi-training implementations can be combined such that the domain-specific coefficients are pre-trained and then further trained in a domain-specific manner. That is, the further training (e.g., the online mode), retrains the coefficients of a particular domain using only data which is representative of that particular domain and similar to the data used in the pre-training stage. In other knowledge transfer implementations, the pre-training and the training can use training data from across the domains, e.g., a coefficient set is generated during the pre-training using images from a patterned flow cell but is retrained during the subsequent training stage using images from an unpatterned flow cell.

Spatial Crosstalk Attenuator

Figure 2:
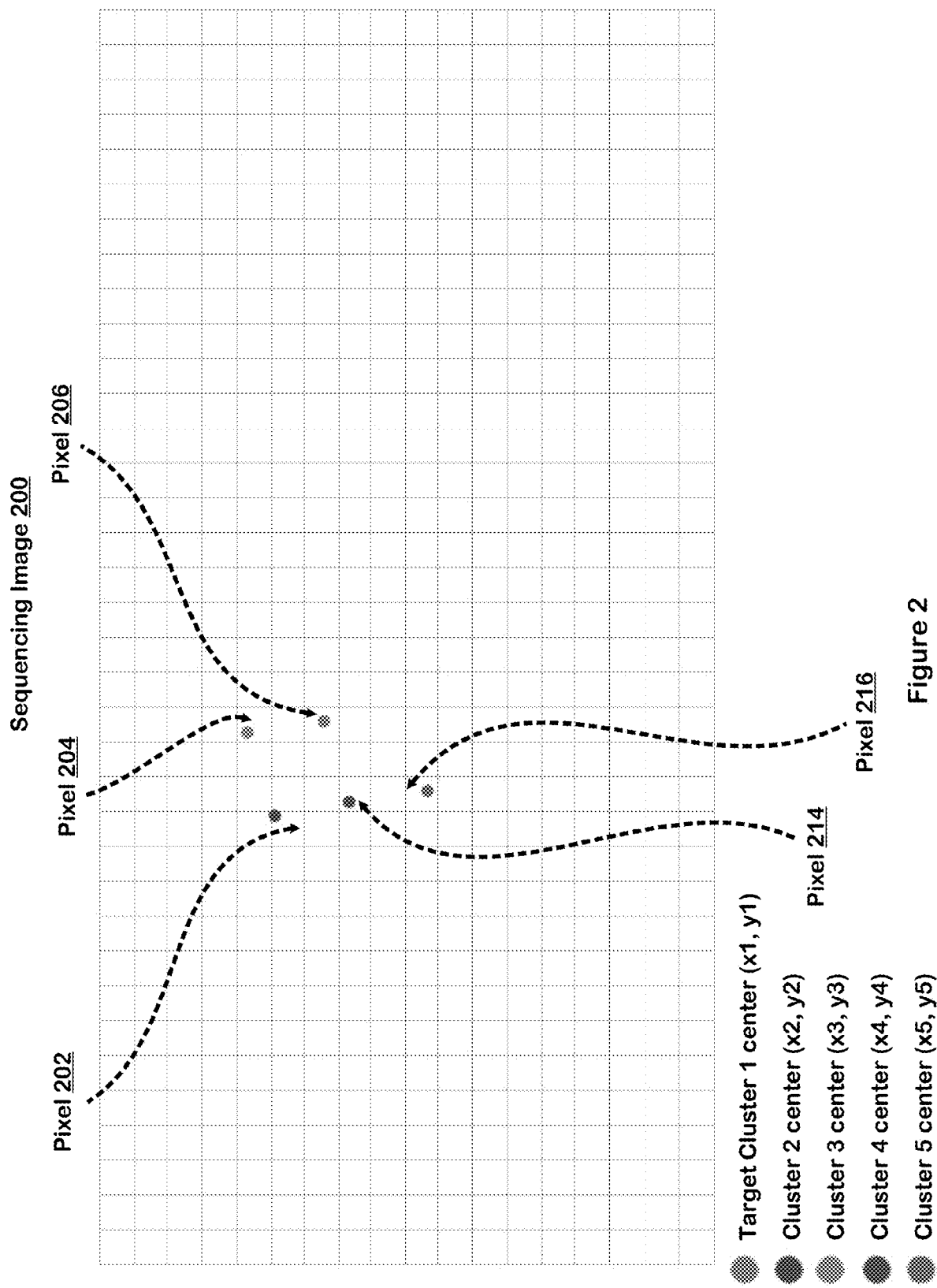
FIG. 2 visualizes one example of a sequencing image that contains centers/point sources of at least five clusters/wells on a flow cell.

FIG. 2 depicts one implementation of using the trained LUTs/equalizer filters 106 of FIG. 1 to attenuate spatial crosstalk from sensor pixels and to base call clusters using crosstalk-corrected sensor pixels. The trained equalizer base caller 104 operates during the inference stage when the base calling takes place. In some implementations, the actions shown in FIG. 2 execute at the preprocessing stage prior to the base calling stage and generates crosstalk-corrected image data that is used by a base caller for base calling.

In one implementation, the equalizer coefficients are applied on pixel patches 120 (image patches or local grids of sensor pixels) that are extracted from sequencing images 116 on an imaging-channel basis and a target cluster basis. Regarding the imaging-channel basis, in some implementations, each sequencing image has image data for a plurality of imaging channels. Consider an optical system of an Illumina sequencer that uses two different imaging channels: a red channel and a green channel. Then, at each sequencing cycle, the optical system produces a red image with red channel intensities and a green image with green channel intensities, which together form a single sequencing image (like RGB channels of a typical color image).

During the training, the coefficients are trained/configured to maximize the signal-to-noise ratio (SNR) by minimizing the error between the predicted/estimated output and the desired/actual output. One example of the error is mean squared error (MSE) or mean squared deviation (MSD). The signal maximized in the signal-to-noise ratio is intensity emissions from a target cluster being base called (e.g., the cluster centered in an image patch), and the noise minimized in the signal-to-noise ratio is intensity emissions from one or more adjacent clusters, i.e., spatial crosstalk, plus other noise sources (e.g., to account for background intensity emissions). The trained coefficients are element-wise multiplied to pixels of the image patch to calculate a weighted sum of the intensity values of the pixels. The weighted sum is then used to base call the target cluster.

In one implementation, patch extractor 118 extracts, from a single sequencing image, a red pixel patch from the red channel and a green pixel patch for the green channel. In other implementations, the red pixel patch is extracted from a red sequencing image of a subject sequencing cycle and the green pixel patch is extracted from a green sequencing image of the subject sequencing cycle. Coefficients of the LUTs 106 are used to generate a red weighted sum for the red pixel patch and a green weighted sum for the green pixel patch. Then, the red weighted sum and the green weighted sum are both used to base call the target cluster. The pixel patches 120 have dimensions w×h, where w (width) and h (height) are any numbers ranging from 1 and 10,000 (e.g., 3×3, 5×5, 7×7, 9×9, 15×15, 25×25). In some implementations, w and h are the same. In other implementations, w and h are different. Those skilled in the art will appreciate that data for one, two, three, four, or more channels or images can be generated per sequencing cycle for the target cluster, and one, two, three, four, or more patches are respectively extracted to respectively generate one, two, three, four or more weights sums for base calling the target cluster.

Regarding the target cluster basis of extracting the pixel patches 120 from the sequencing images 116, the pixel extractor 118 extracts the pixel patches 120 based on where the centers of the clusters/wells are located on the sequencing images 116 such that the center pixel of each extracted pixel patch contains a center of a target cluster/well. In some implementations, the patch extractor 118 locates cluster/well centers on a sequencing image, identifies those pixels of the sequencing image that contain the cluster/well centers (i.e., center pixels), and extracts pixel patches of contiguously adjacent pixel neighborhoods around the center pixels.

FIG. 2 visualizes one example of a sequencing image 200 that contains centers/point sources of at least five clusters/wells on a flow cell. Pixels of the sequencing image 200 depict intensity emissions from a target cluster 1 (in blue) and intensity emissions from additional adjacent cluster 2 (in purple), cluster 3 (in orange), cluster 4 (in brown), and cluster 5 (in green).

Figure 3:
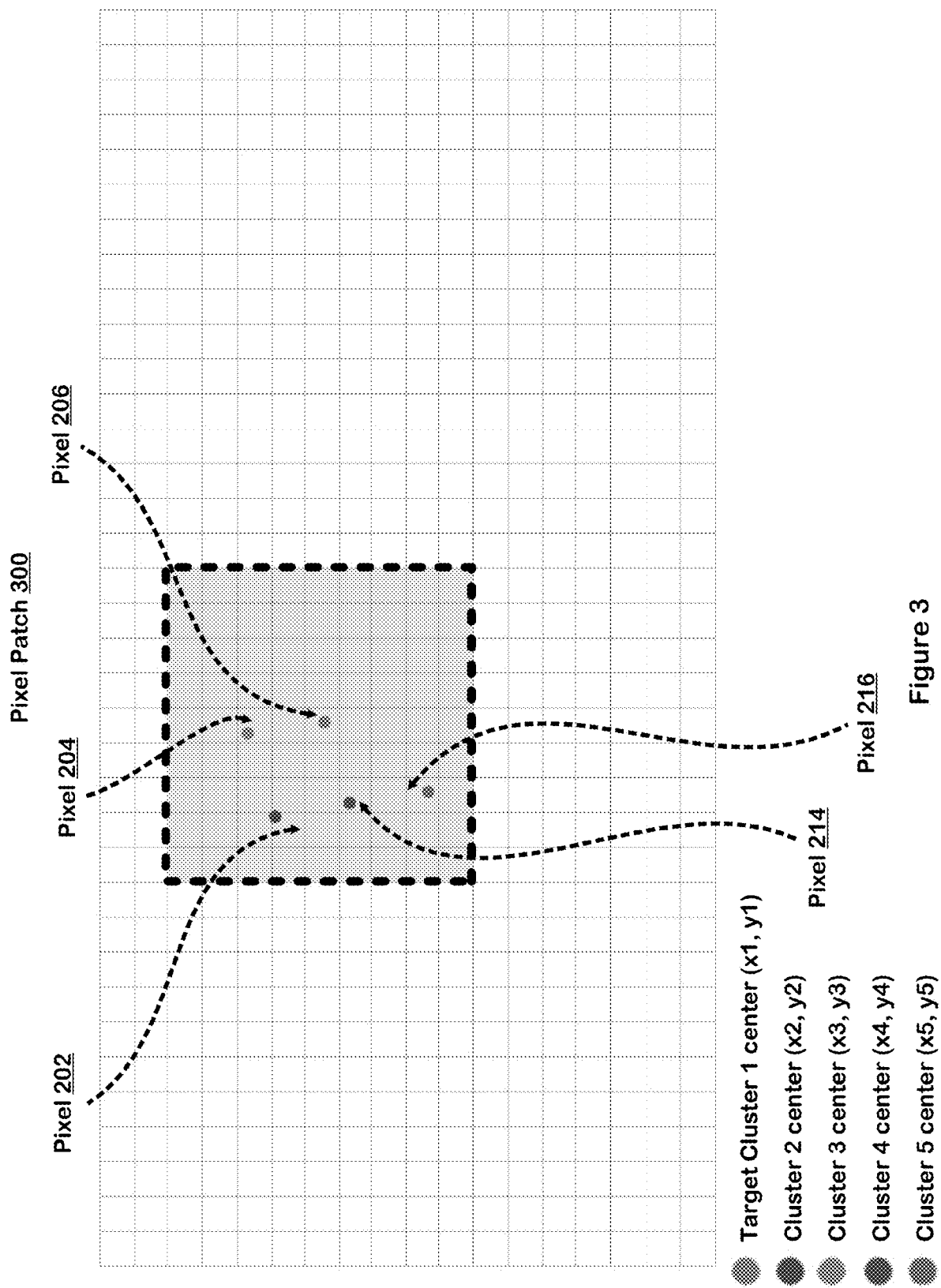
FIG. 3 visualizes one example extracting a pixel patch (in yellow) from the sequencing image of FIG. 2 such that the center of the target cluster 1 (in blue) is contained in the center pixel of the pixel patch.

FIG. 3 visualizes one example extracting a pixel patch 300 (in yellow) from the sequencing image 200 such that the center of the target cluster 1 (in blue) is contained in the center pixel 206 of the pixel patch 300. FIG. 3 also shows other pixels 202, 204, 214, and 216 that respectively contain centers of the adjacent cluster 2 (in purple), cluster 3 (in orange), cluster 4 (in brown), and cluster 5 (in green).

Figure 4:
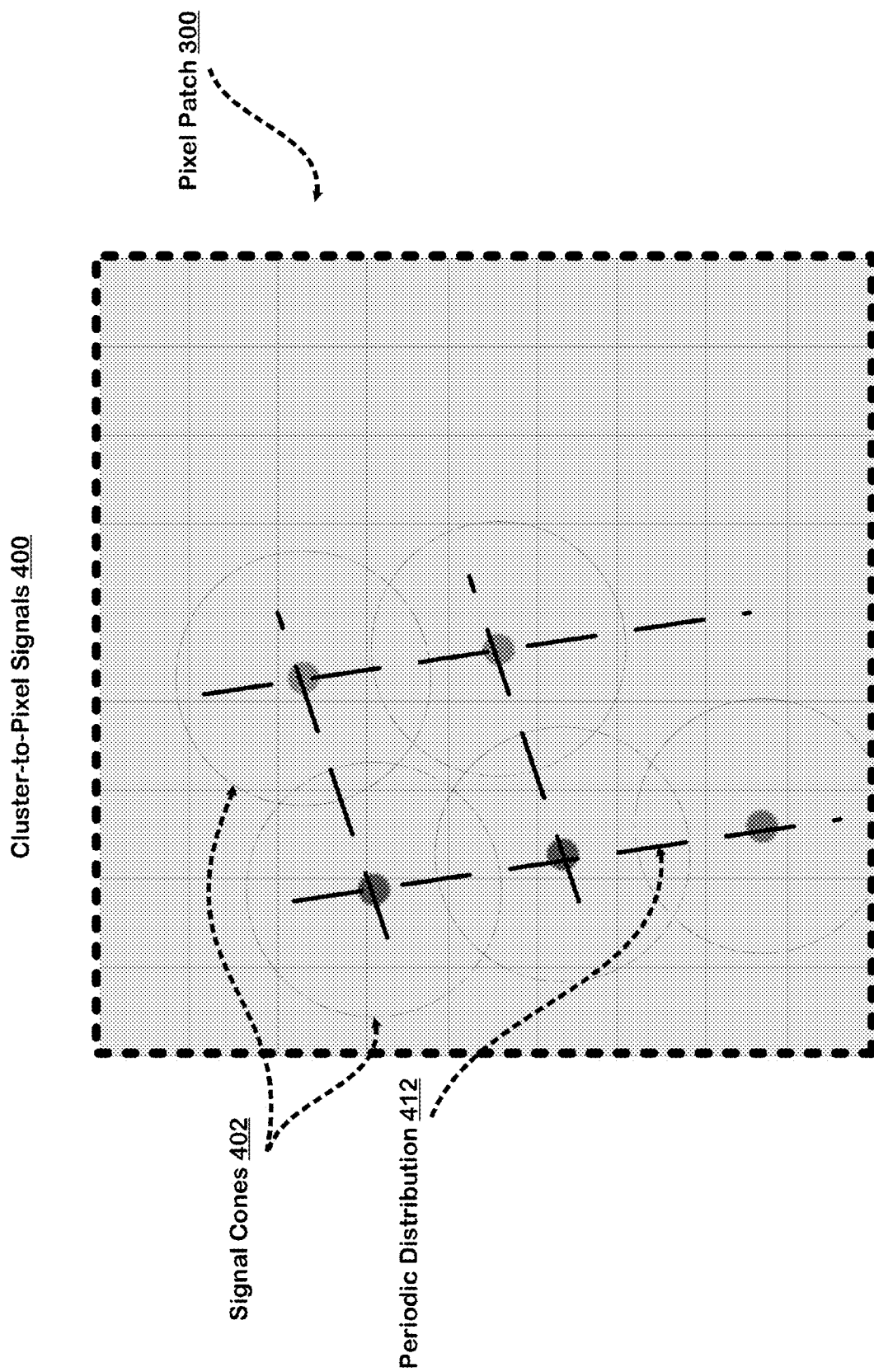
FIG. 4 visualizes one example of cluster-to-pixel signals.

FIG. 4 visualizes one example of cluster-to-pixel signals 400. In one implementation, the sensor pixels (in yellow) are in a pixel plane. The spatial crosstalk is caused by periodically distributed clusters 412 in a sample plane (e.g., a flow cell). In one implementation, the target cluster and the additional adjacent clusters are periodically distributed on the flow cell in a diamond shape and immobilized on wells of the flow cell. In another implementation, the target cluster and the additional adjacent clusters are periodically distributed on the flow cell in a hexagonal shape and immobilized on wells of the flow cell. Signal cones 402 from the cluster are optically coupled to local grids of the sensor pixels (e.g., pixel patch 300) through at least one lens (e.g., one or more lenses of overhead or adjacent CCD cameras).

In addition to the diamond shape and hexagonal shape, the clusters can be arranged in other regular shapes such as a square, a rhombus, a triangle, and so on. In yet other implementations, the clusters are arranged on the sample plane in a random, non-periodic arrangement. One skilled in the art will appreciate that the clusters can be arranged on the sample plane in any arrangement, as needed by a particular sequencing implementation.

Figure 5:
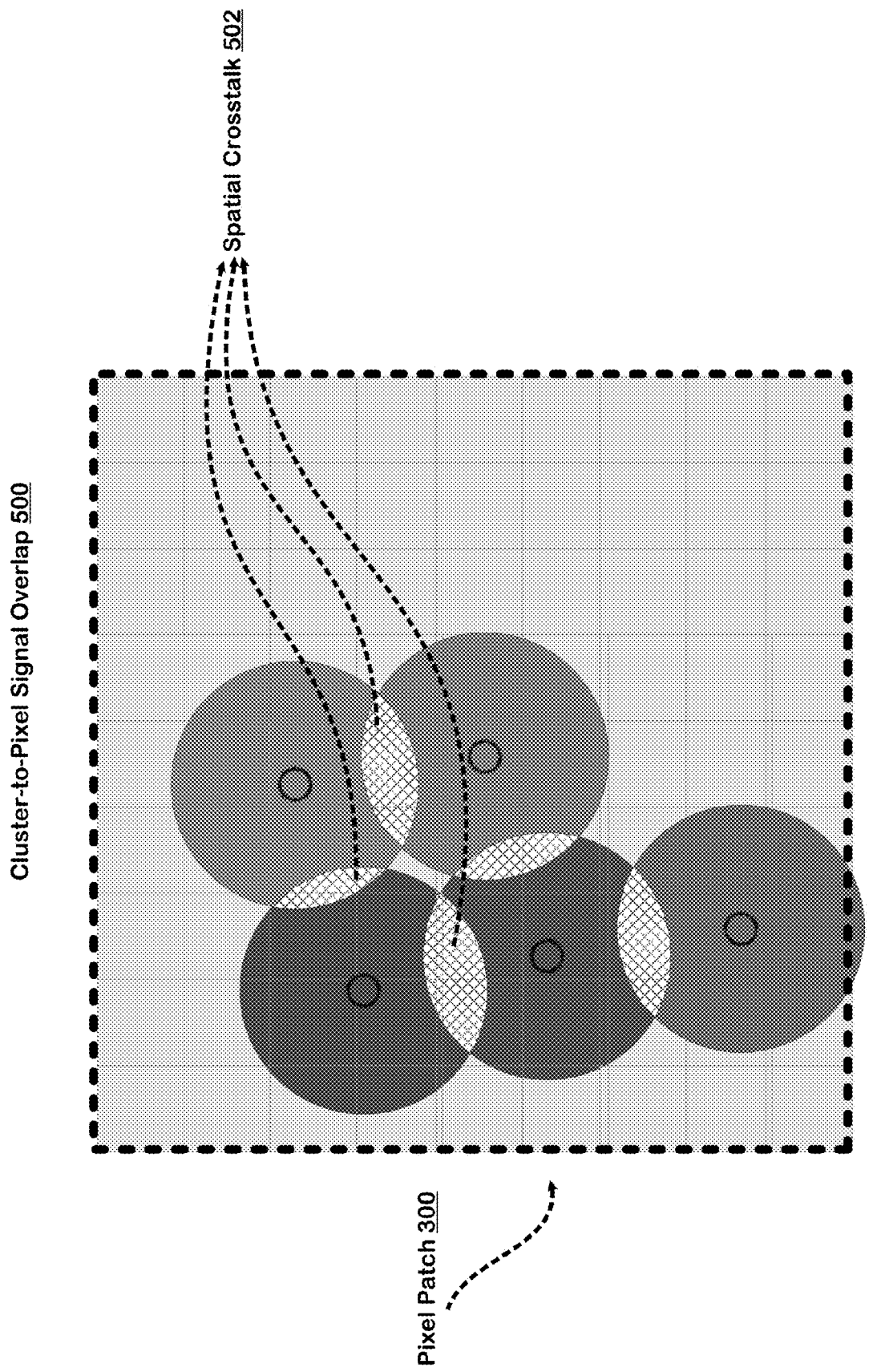
FIG. 5 visualizes one example of cluster-to-pixel signal overlap.

FIG. 5 visualizes one example of cluster-to-pixel signal overlap 500. The signal cones 402 overlap and impinge on the sensor pixels, creating spatial crosstalk 502.

Figure 6:
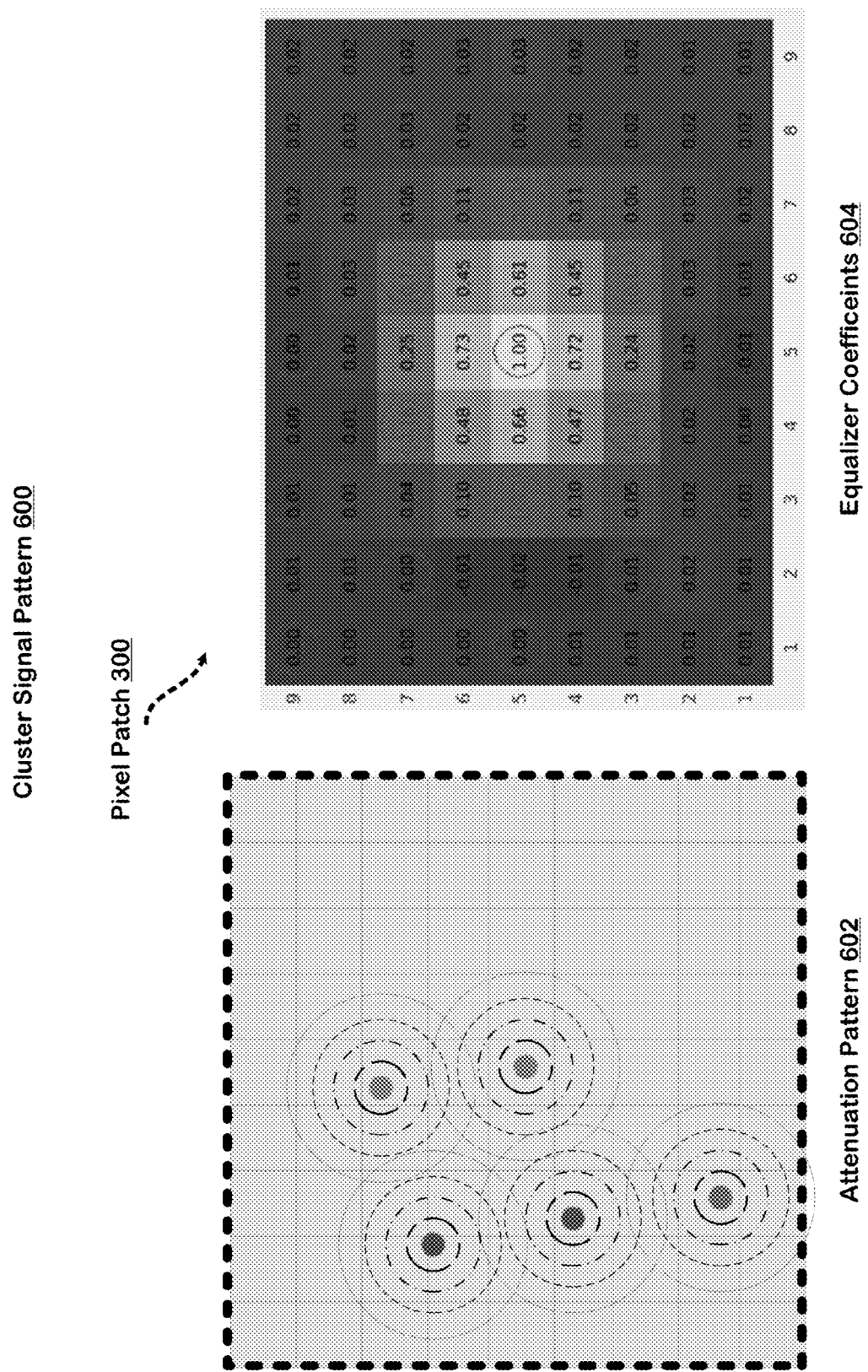
FIG. 6 visualizes one example of cluster signal pattern.

FIG. 6 visualizes one example of cluster signal pattern 600. In one implementation, the cluster signal pattern 600 follows an attenuation pattern 602 in which the cluster signal is strongest at a cluster center and attenuates as it propagates away from the cluster center.

FIG. 6 also shows one example of equalizer coefficients 604 that are trained/configured to maximize the signal-to-noise ratio by calculating a weighted sum of the intensity emissions from the target cluster 1 and intensity emissions from the adjacent cluster 2, cluster 3, cluster 4, and cluster 5. The equalizer coefficients 604 serve as the weights. The weighted sum is calculated by element-wise multiplying a first matrix that comprises the equalizer coefficients 604 with a second matrix that comprises pixels intensity values, with each pixel intensity value being the sum of the emissions from one or more of the clusters 1, 2, 3, 4, and 5, plus other noise sources in the system measured by the pixel sensors.

Figure 7:
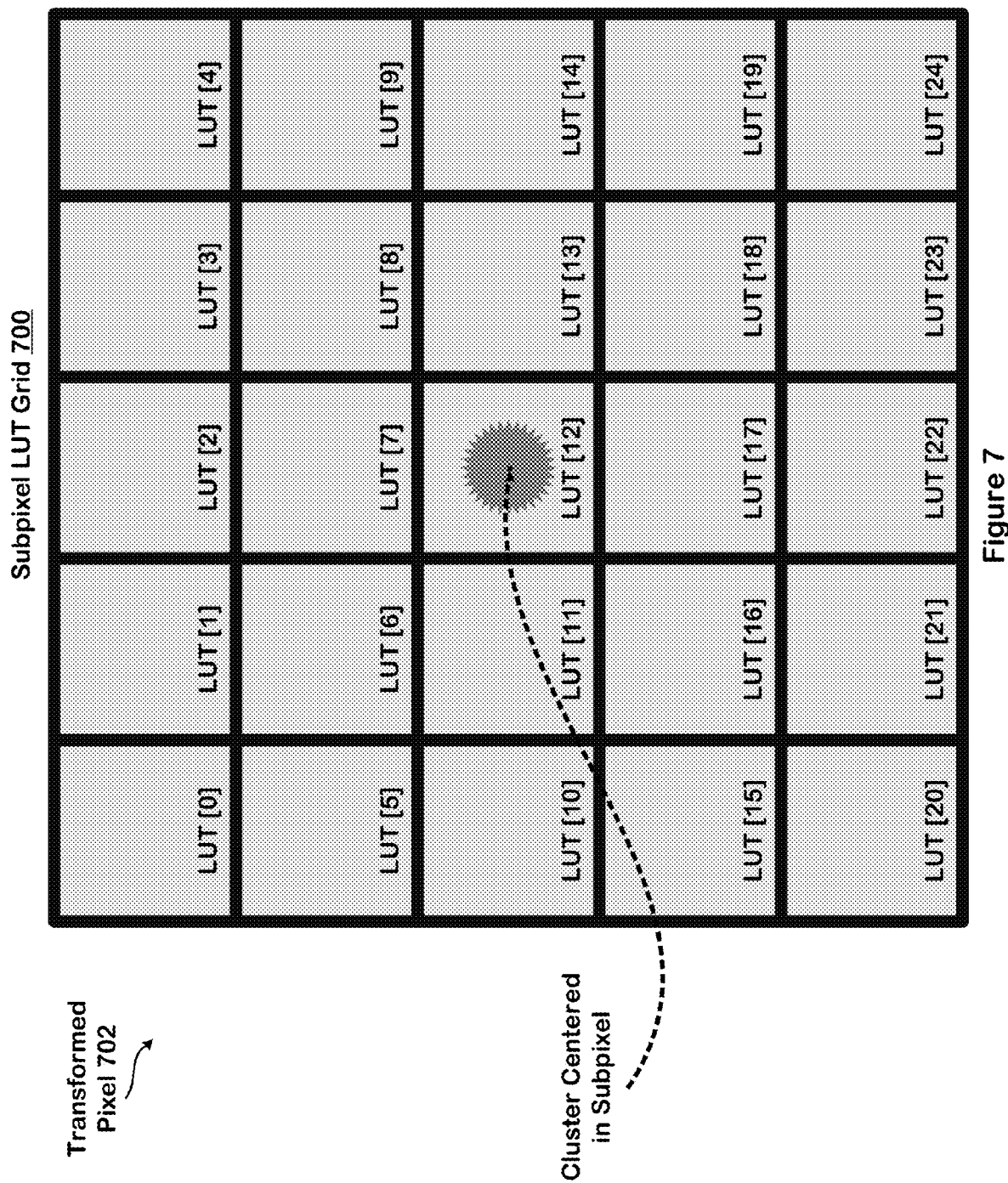
FIG. 7 visualizes one example of a subpixel LUT grid that is used to attenuate spatial crosstalk from the pixel patch of FIG. 3.

FIG. 7 visualizes one example of a subpixel LUT grid 700 that is used to attenuate spatial crosstalk from the pixel patch 300. Each pixel in the pixel patch 300 is divisible into a plurality of subpixels. In FIG. 7, the pixel 206 that contains the center of the target cluster 1 (in blue), is divided into as many subpixels as the number of trained LUTs 106. That is, the pixel 206 is partitioned into the same number of subpixels as the number of bins for which, during the training, the equalizer 104 generated the LUTs 106. As a result, each subpixel of the pixel 206 corresponds to a respective LUT in the LUT bank produced by the equalizer 104 using the decision-directed feedback and the least square estimation.

In the example shown in FIG. 7, the pixel 206 (the center pixel) is divided into a 5×5 subpixel LUT grid 700 to produce 25 subpixels that respectively correspond to 25 LUTs (equalizer filters) generated by the adaptive filter 104 as a result of the training. Each of the 25

LUTs comprises coefficients that are configured to mix/combine intensity values of pixels in the pixel patch 300 that depict intensity emissions from the target cluster 1 and intensity emissions from the adjacent cluster 2, cluster 3, cluster 4, and cluster 5 in a manner that maximizes the signal-to-noise ratio. The signal maximized in the signal-to-noise ratio is the intensity emissions from the target cluster, and the noise minimized in the signal-to-noise ratio is the intensity emissions from the adjacent cluster 2, cluster 3, cluster 4, and cluster 5., i.e., spatial crosstalk, plus some random noise (e.g., to account for background intensity emissions). The LUT coefficients are used as weights and the mixing/combining includes executing element-wise multiplication between the LUT coefficients and the intensity values of the pixels in the pixel patch 300 to calculate a weighted sum of the intensity values of the pixels.

The number of coefficients in each of the 25 LUTs is the same as the number of pixels in the pixel patch 300, i.e., 9×9 coefficient grid in each LUT for 9×9 pixels in the pixel patch 300. This is the case because the coefficients are element-wise multiplied with the pixels in the pixel patch 300.

In one implementation, a pixel-to-subpixel converter (not shown in FIG. 1B) divides the pixel 206 into the subpixel LUT grid 700 based on a preset pixel divisor parameter (e.g., 1/5 pixel per subpixel to generate the 5×5 subpixel LUT grid 700). For example, a pixel can be divided into five subpixel bins with the following boundaries: −0.5, −0.0.3, −0.1, 0.1, 0.3, 0.5.

In FIG. 7, note that the center of the target cluster 1 (in blue) is substantially concentric with the center of a transformed pixel 702. This is the case because the sequencing image 200, and therefore the pixel patch 300, is resampled to make the center of the target cluster 1 (in blue) substantially concentric with the center of the transformed pixel 702 by (i) registering the sequencing image 200 against a template image and determining affine transformation and non-linear transformation parameters, (ii) using the parameters to transform location coordinates of the target cluster 1 (in blue) to image coordinates of the sequencing image 200, and (iii) applying interpolation using the transformed location coordinates of the target cluster 1 (in blue) to make its center substantially concentric with the center of the transformed pixel 702. The location of the wells in the sample plane is known and can be used to calculate where the equalizer inputs for a particular well are in the in raw-pixel space. We can then use interpolation to recover the intensity at those positions from the raw images.

Figure 8:
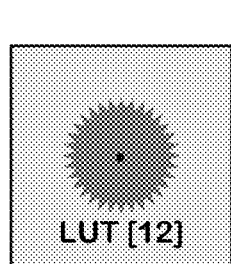
FIG. 8 shows selection of a LUT/equalizer filter from the LUT bank of FIG. 1B based on a subpixel location of a cluster/well center within a pixel.

FIG. 8 shows selection of a LUT/equalizer filter from the LUT bank 106 based on a subpixel location of a cluster/well center within a pixel. Since the center of the target cluster (in blue) falls in a particular subpixel 12 of the subpixel LUT grid 700, and the particular subpixel 12 of the pixel 206 corresponds to LUT 12 in the LUT bank 106, the LUT selector 122 selects LUT 12 and its coefficients from the LUT bank 106 for application on the pixels of the pixel patch 300. Then, a element-wise multiplier 134 element-wise multiplies the coefficients of LUT 12 to intensity values of the pixels in the pixel patch 300, and sums products of the multiplications to produce an output (e.g., weighted sum 136). The output is used to base call the target cluster 1 (e.g., by feeding the output as input to a base caller 138).

The equalizer 104 implements the following equalization logic when the target cluster is substantially concentric with the center of a pixel, as discussed above with respect to FIGS. 7 and 8:

$$y_{m,n} = \sum_{i,j} p(m+i, n+j) \cdot w(i, j) + \text{dc offset}$$

In the equation above, the well center coordinates (m, n) are integers to ensure the well is aligned substantially with a pixel; p(i, j) is the pixel intensity at position i, j; w(i, j) is the equalizer weight for the pixel at position i, j; the i, j are the summation limits that operate over the pixel range that surrounds the well centered in p(m, n), e.g. −4<=i<=4, −4<=j<=4; and the output is a weighted average of the input pixels.

Figure 9:
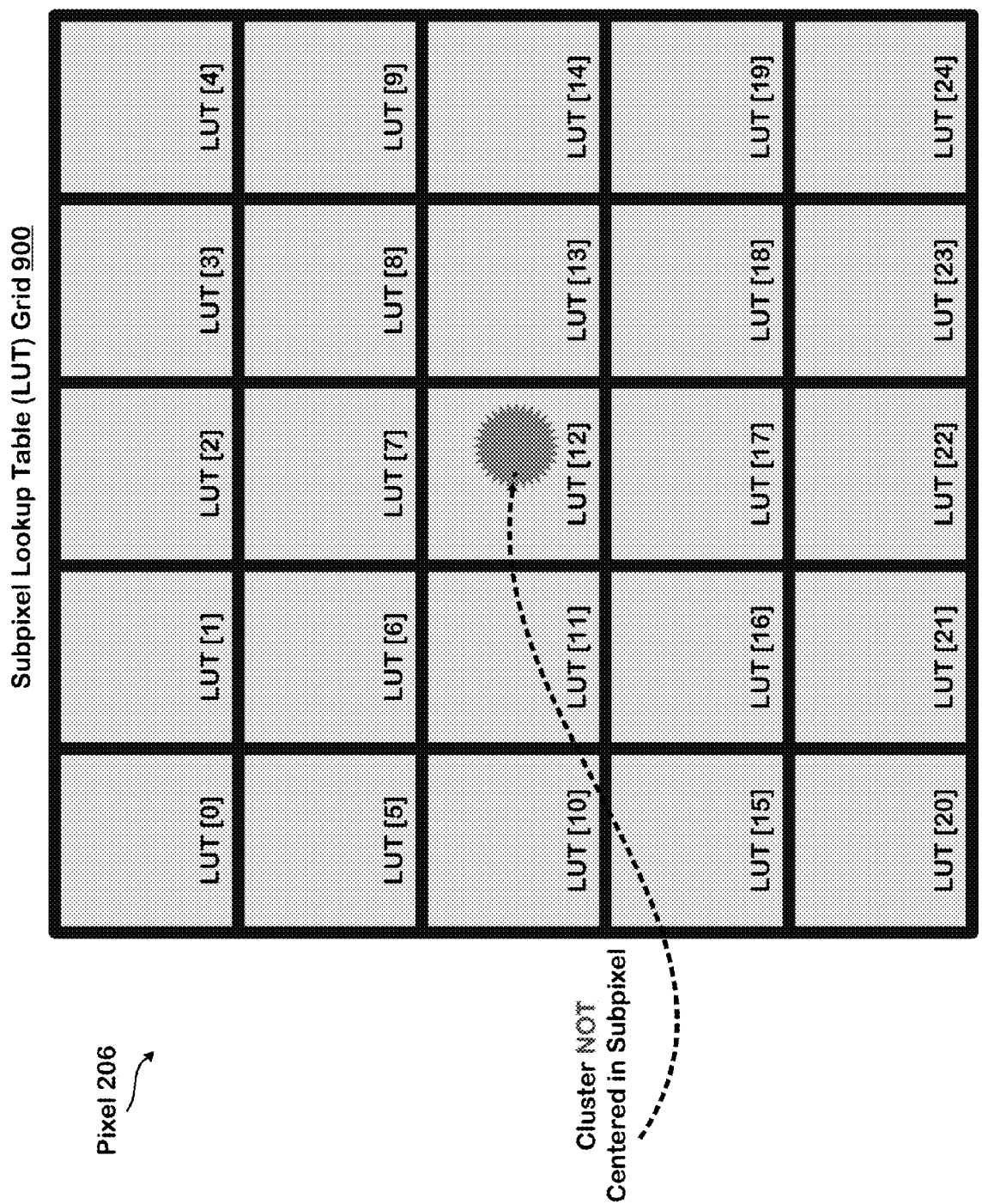
FIG. 9 illustrates one implementation in which the center of the target cluster 1 (in blue) is NOT substantially concentric with the center of the pixel.

FIG. 9 illustrates one implementation in which the center of the target cluster 1 (in blue) is NOT substantially concentric with the center of the pixel 206 because no resampling is performed such as the one discussed with respect to FIG. 8. In such an implementation, the interpolation occurs among a set of selected LUTs 124 to produce an interpolated LUT with interpolated coefficients. The interpolated LUT with the interpolated coefficients is also referred to herein as a weights kernel 132.

First, like in FIG. 8, a first LUT is selected that corresponds to the particular subpixel in which the center of the target cluster 1 (in blue) falls, i.e., LUT 12. Then, the LUT selector 122 selects additional subpixel lookup tables, from the bank of subpixel look tables 106, which correspond to subpixels that are most contiguously adjacent to the particular subpixel. In FIG. 9, the nearest contiguously adjacent subpixels that abut the particular subpixel 12 are subpixels 7, 8, and 13, and therefore LUTs 7, 8, and 13 are respectively selected from the LUT bank 106.

Figure 10:
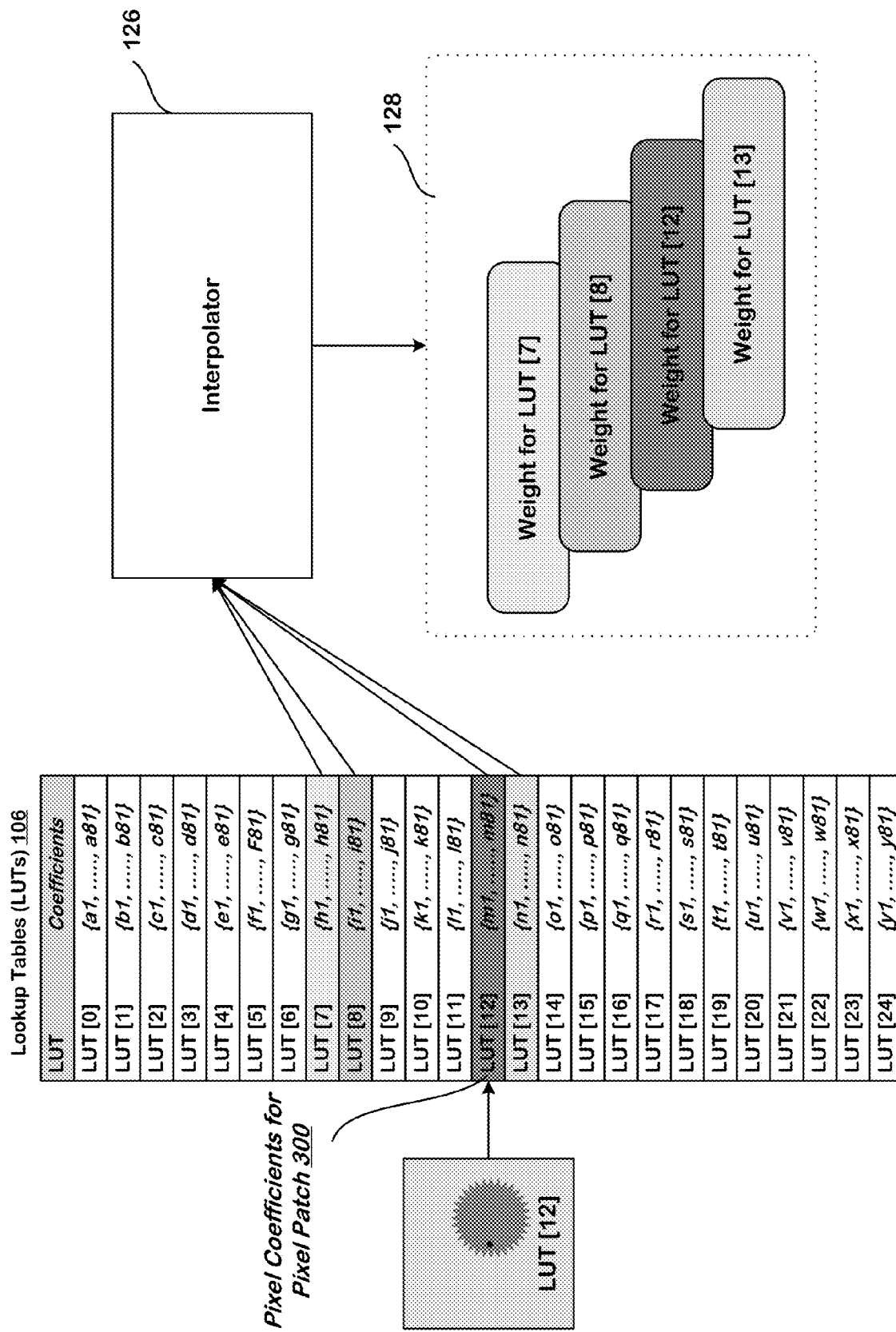
FIG. 10 depicts one implementation of interpolating among a set of selected LUTs and generating respective LUT weights.

FIG. 10 depicts one implementation of interpolating among a set of selected LUTs and generating respective LUT weights. Interpolator 126 is configured with an interpolation logic (e.g., linear, bilinear, or bicubic interpolation) that uses the coefficients of the selected LUTs 12, 7, 8, and 13 and generates weights 128 for each of the LUTs 12, 7, 8, and 13.

FIGS. 13A, 13B, 13C, 13D, 13E, and 13F show example of coefficients of the LUTs 12, 7, 8, and 13. These figures also show examples 1312, 1322, and 1332 of the interpolation logic that is used by the interpolator 126 to calculate the weights 128 for the LUTs 12, 7, 8, and 13. These figures also show examples of the calculated weights 128 for the LUTs 12, 7, 8, and 13. These figures are snapshots of an Excel sheet, and the blue arrows and color coding in these figures are generated by the Track Precedence feature of Excel to demonstrate the interpolation logic.

Figure 11:
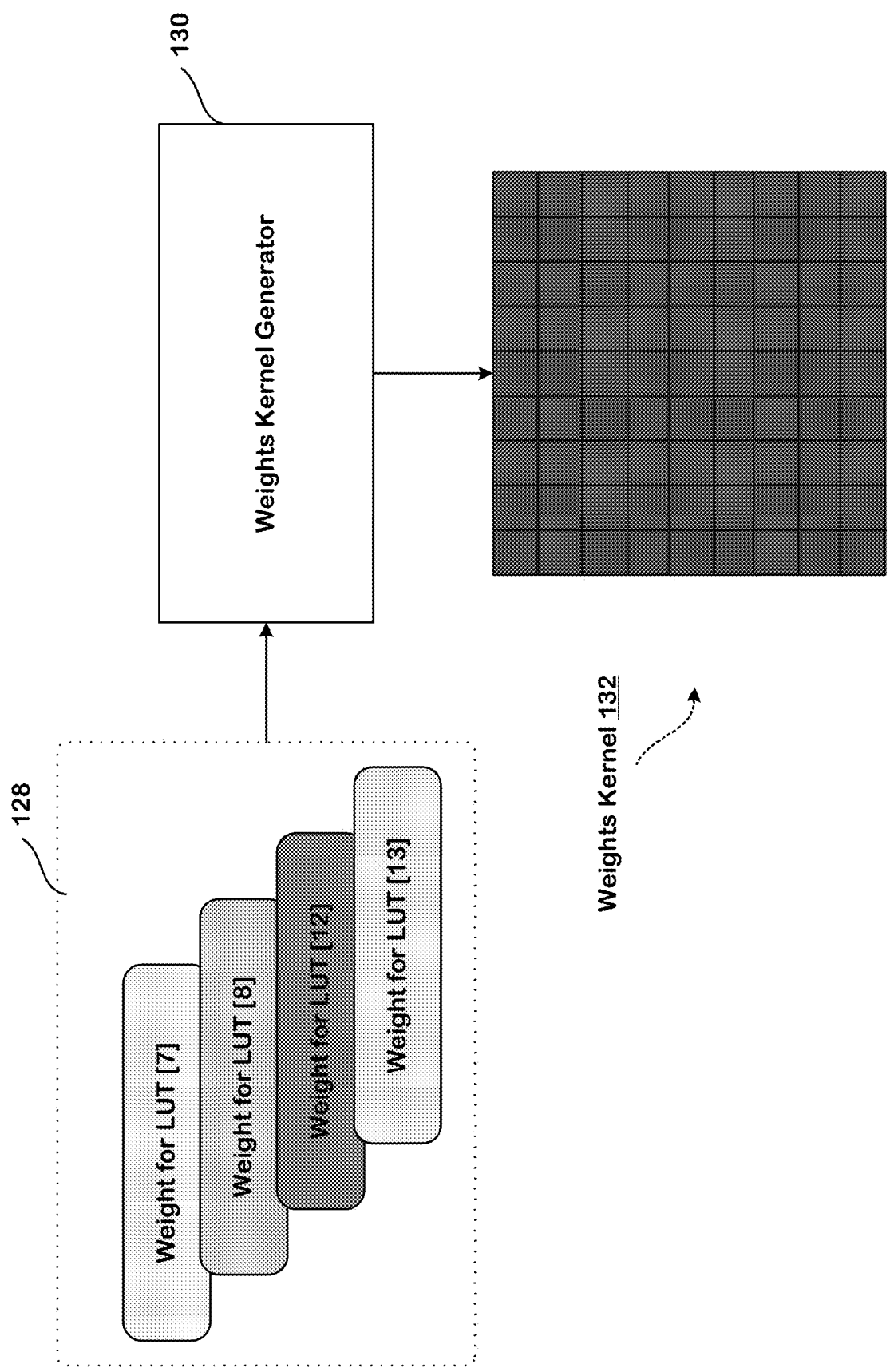
FIG. 11 shows a weights kernel generator generating the weights kernel using the calculated weights of the LUTs 12, 7, 8, and 13.
Figure 13B:
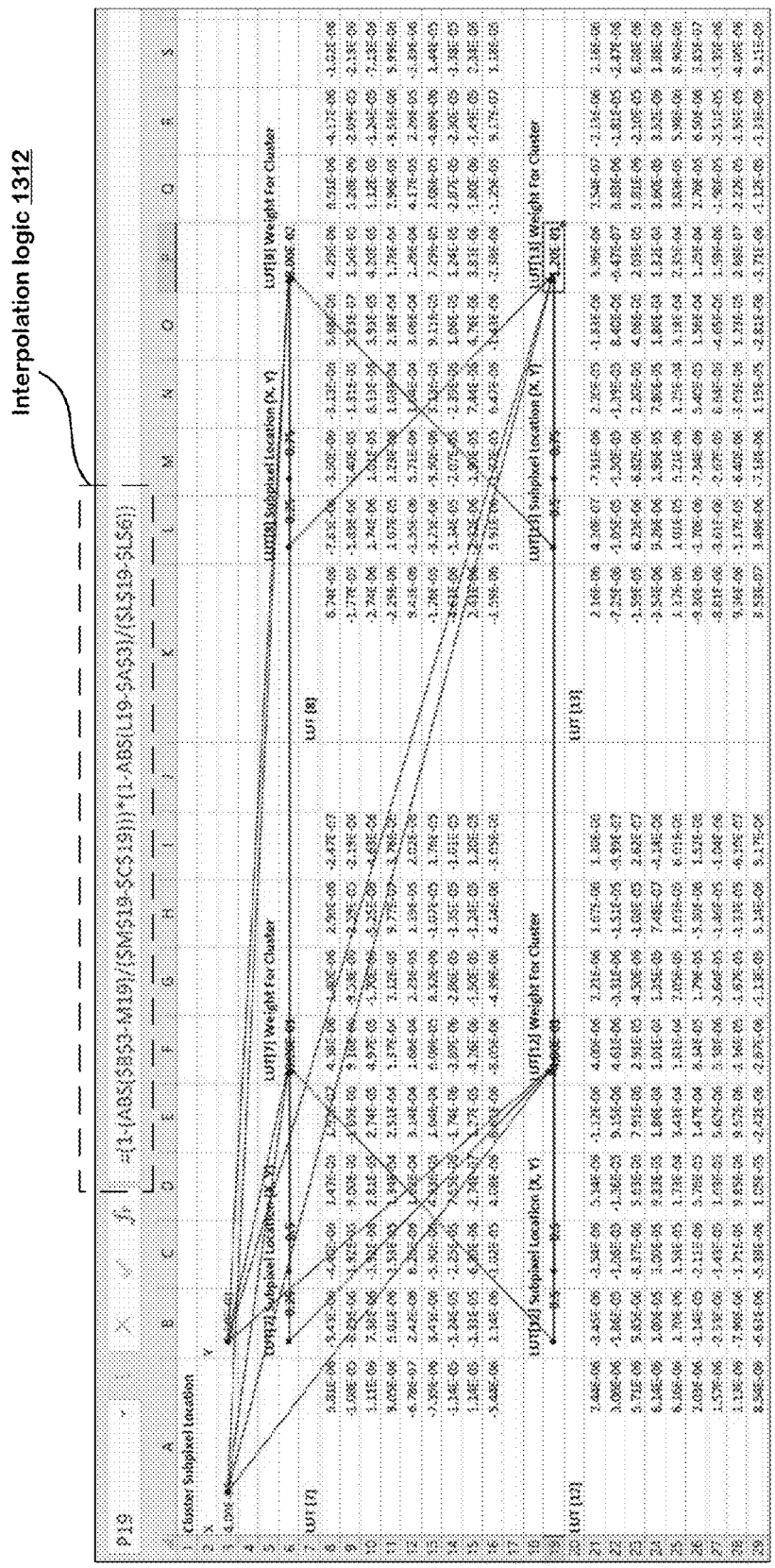
Figure 13C:
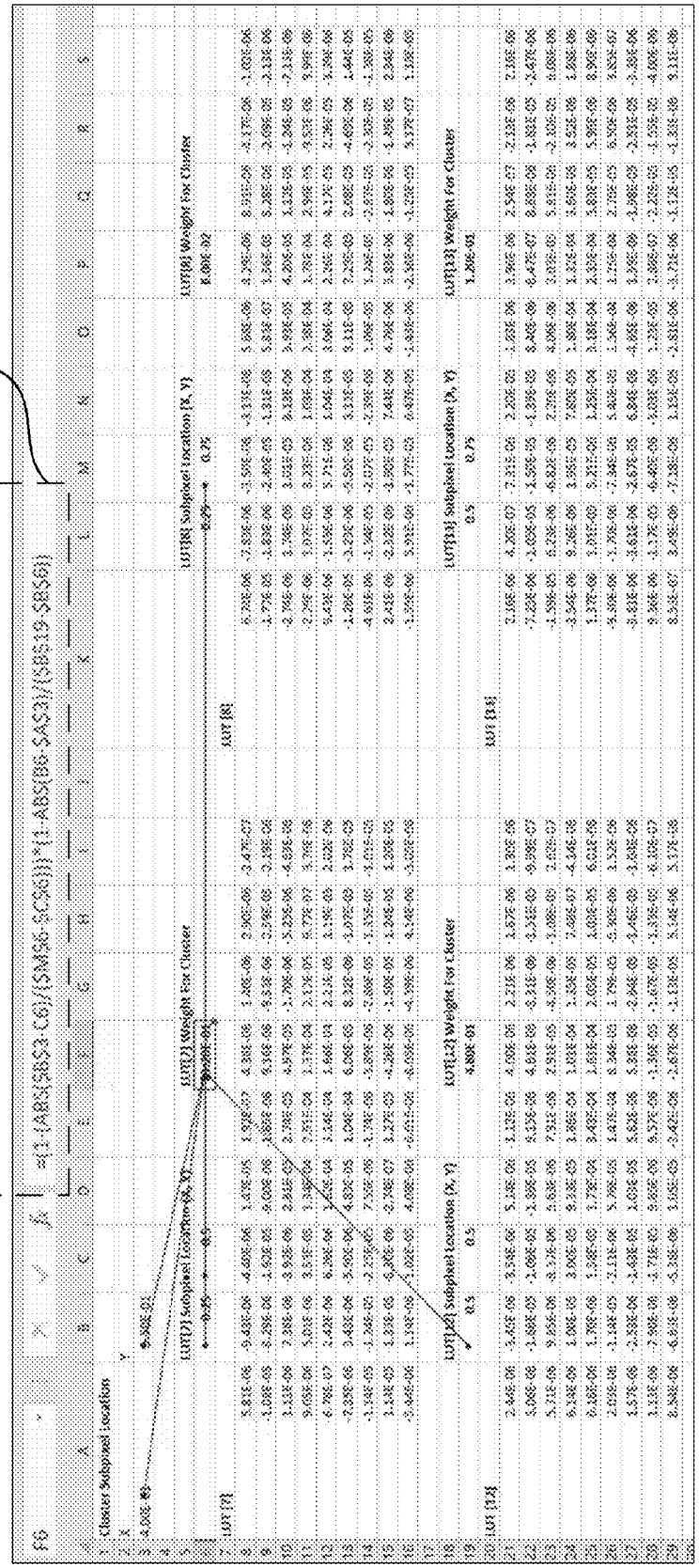
Figure 13E:
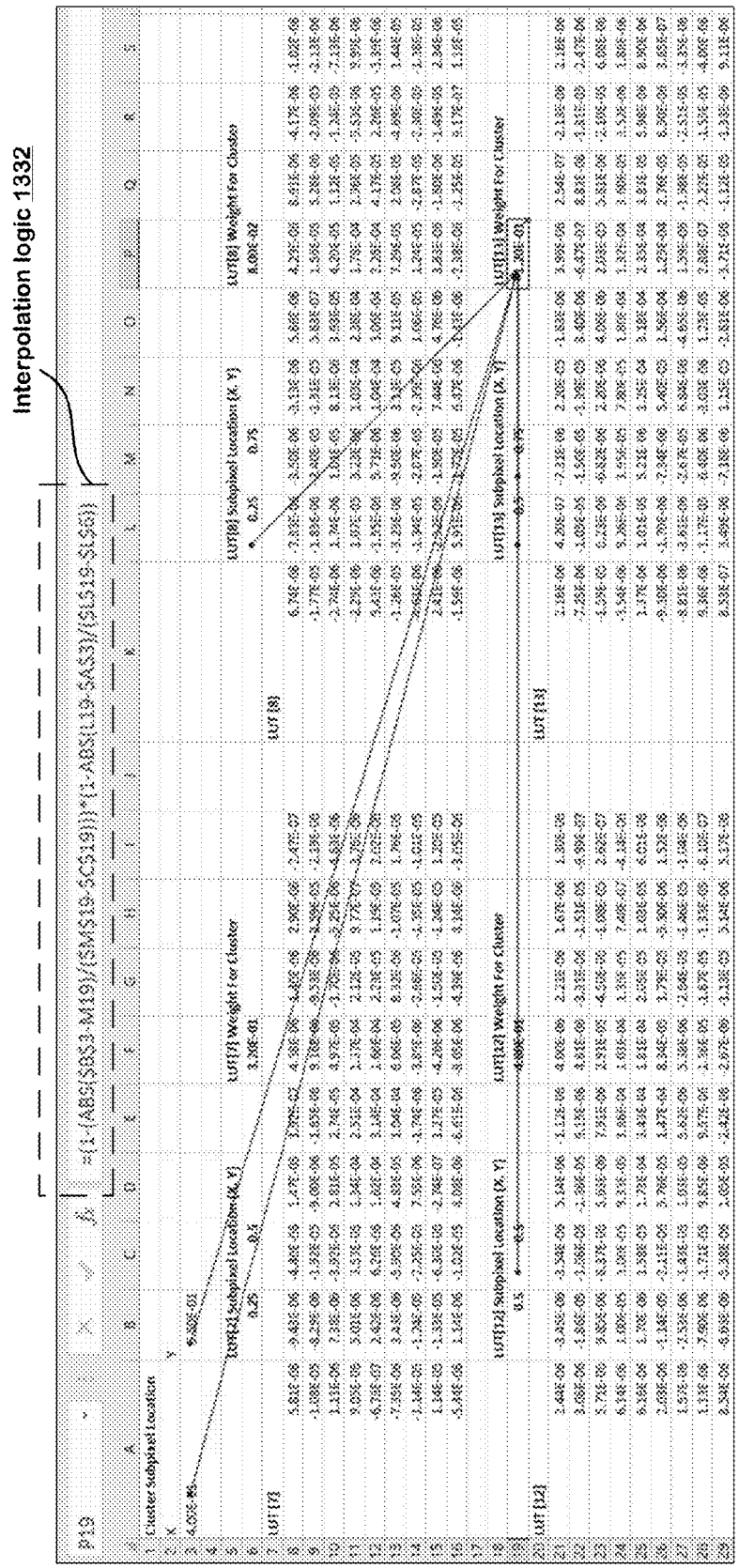
Figure 14B:
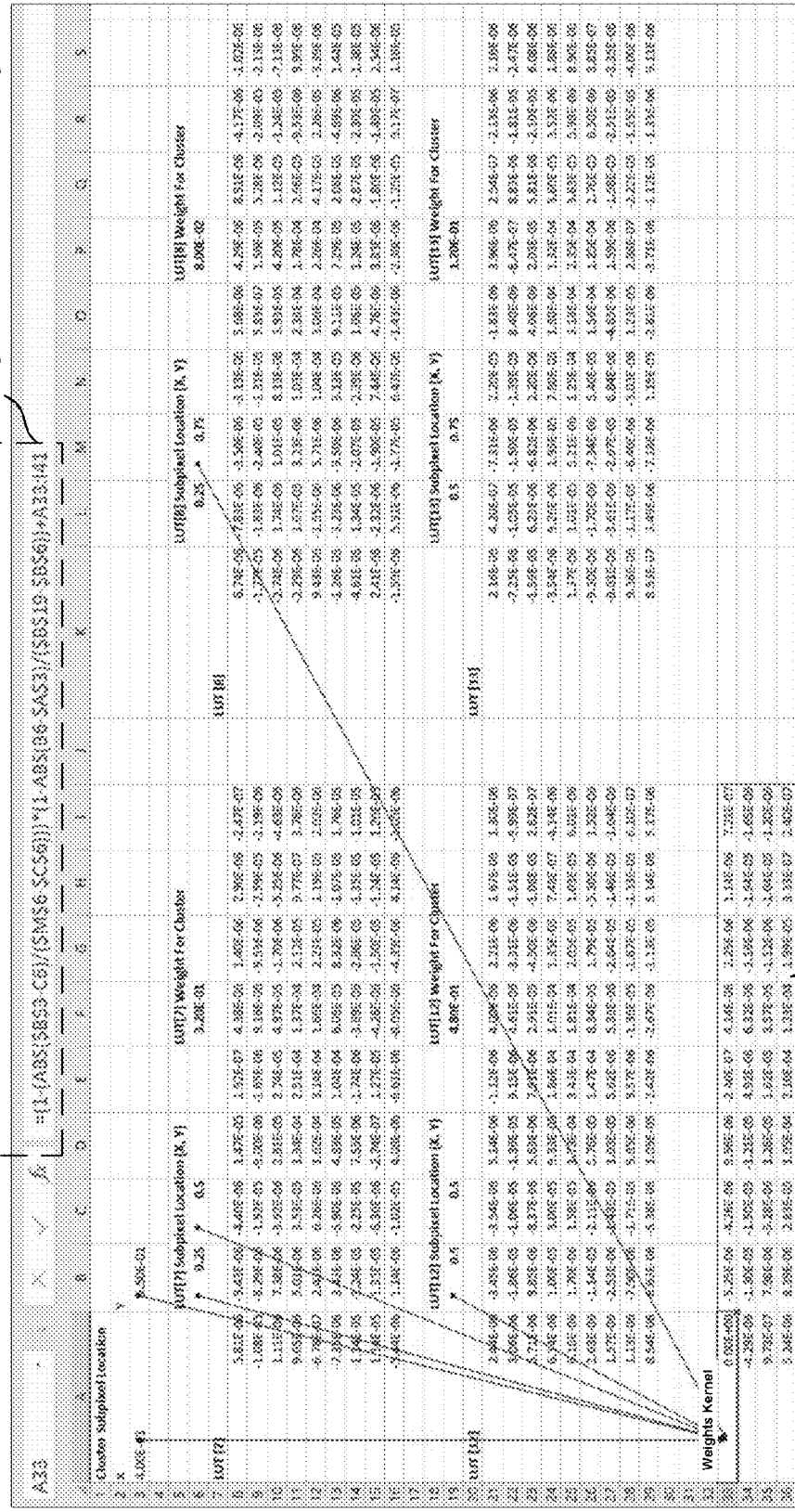
FIGS. 14B and 14C illustrate one example of the weights kernel generation logic used by the weights kernel generator to generate the weights kernel from the calculated weights of the LUTs 12, 7, 8, and 13.
Figure 14C:
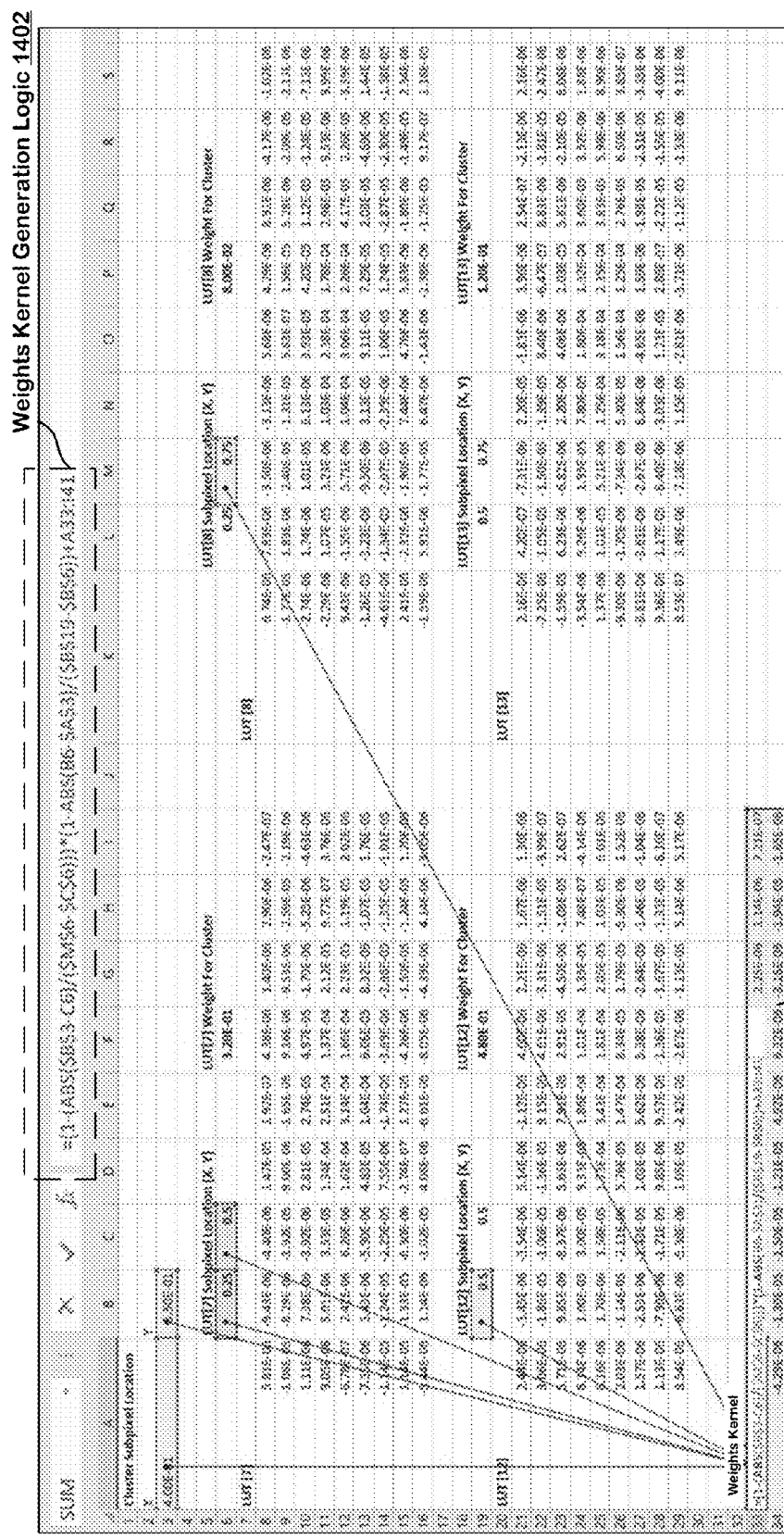

FIG. 11 shows a weights kernel generator 130 generating the weights kernel 132 using the calculated weights 128 for the LUTs 12, 7, 8, and 13. FIG. 14A depicts an example of the weights kernel 132. FIGS. 14B and 14C illustrate one example 1402 of the weights kernel generation logic used by the weights kernel generator 130 to generate the weights kernel 132 from the calculated weights 128 for the LUTs 12, 7, 8, and 13. The weights kernel 132 comprises interpolated pixel coefficients 1412 that are configured to mix/combine intensity values of pixels in the pixel patch 300 that depict intensity emissions from the target cluster 1 and intensity emissions from the adjacent cluster 2, cluster 3, cluster 4, and cluster 5 in a manner that maximizes the signal-to-noise ratio. The signal maximized in the signal-to-noise ratio is the intensity emissions from the target cluster, and the noise minimized in the signal-to-noise ratio is the intensity emissions from the adjacent cluster 2, cluster 3, cluster 4, and cluster 5., i.e., spatial crosstalk, plus some random noise (e.g., to account for background intensity emissions). The interpolated pixel coefficients 1412 are used as weights and the mixing/combining includes executing element-wise multiplication between the LUT coefficients and the intensity values of the pixels in the pixel patch 300 to calculate a weighted sum of the intensity values of the pixels.

FIG. 12 shows the element-wise multiplier 134 element-wise multiplying the interpolated pixel coefficients 1412 of the weights kernel 132 with the intensity values of the pixels in the pixel patch 300 and summing intermediate products 1202 of the multiplications to produce the weighted sum 136. For each well, the optical system operates over a point source (the cluster intensity in the well) with a point spread function (the response of the optical system). In some implementations, a bias is added to the operation to account for noise caused by different cluster sizes, different background intensities, varying stimulation responses, varying focus, varying sensor sensitivities, and varying lens aberrations. The captured image is a superposition of the responses from all the wells. The selected LUT equalizes the system response around each well to estimate the intensity of the point source from that well i.e. it processes the PSF intensity over the local neighborhood/grid of sensor pixels to estimate the intensity of the point source that generated the local grid of sensor pixels. This equalizer operation is a dot product on the sensor pixels in the local grid with the equalizer coefficients.

The equalizer 104 implements the following equalization logic when the target cluster is NOT substantially concentric with the center of the center pixel, as discussed above with respect to FIGS. 9, 10, 11, and 12. When the well is not centered in a pixel, the output of the equalizer 104 is calculated as a function of virtual pixel intensities p'(i, j) that are derived from the actual pixel intensities of the pixels of the sequencing image:

$$y_{m,n} = \Sigma_{i,j} p'(m+i, n+j) \cdot w(i,j) \quad (1)$$

In the equation above, the well center coordinates (m, n) can have fractional parts. Each 'virtual' equalizer input p'(i, j) is generated by applying an interpolation filter to the pixel neighborhood. In one implementation, a windowed-sinc low-pass filter h(x, y) is used for interpolation. In other implementations, some other filters like bi-linear interpolation filters can be used.

The virtual pixel at location (i, j) is calculated using the interpolation filter as:

$$p'(i,j) = \Sigma_{u,v} p(u,v) \cdot h(i-u, j-v) \quad (2)$$

By combining equations (1) and (2), the equalizer 104 uses only the raw pixel intensities as follows:

$$y_{m,n} = \sum_{i,j} \sum_{u,v} p(u, v) \cdot h(i - u, j - v) \cdot w(i, j)$$

In the equation above, h is fixed given a subpixel offset frac(m), frac(n); u, v specify the range of pixels used for interpolation to generate the equalizer inputs; and i, j specify the range of virtual pixels used as inputs to the equalizer 104.

For a given subpixel offset, all that changes is the input pixels, not the filter or weights. Therefore, for the center of each binned subpixel offset, we calculate a fixed set of interpolated equalizer coefficients. Then the output is:

$$y_{m,n} = \sum_{i,j} \sum_{u,v} p(u, v) \cdot h_{fm,fn}(i - u, j - v)$$

In equation above, $h_{fm,fn}$ denotes the LUT equalizer coefficients for wells with binned fractional subpixel offset fm, fn, where (fm, fn) are the LUT indices.

Figure 15A:
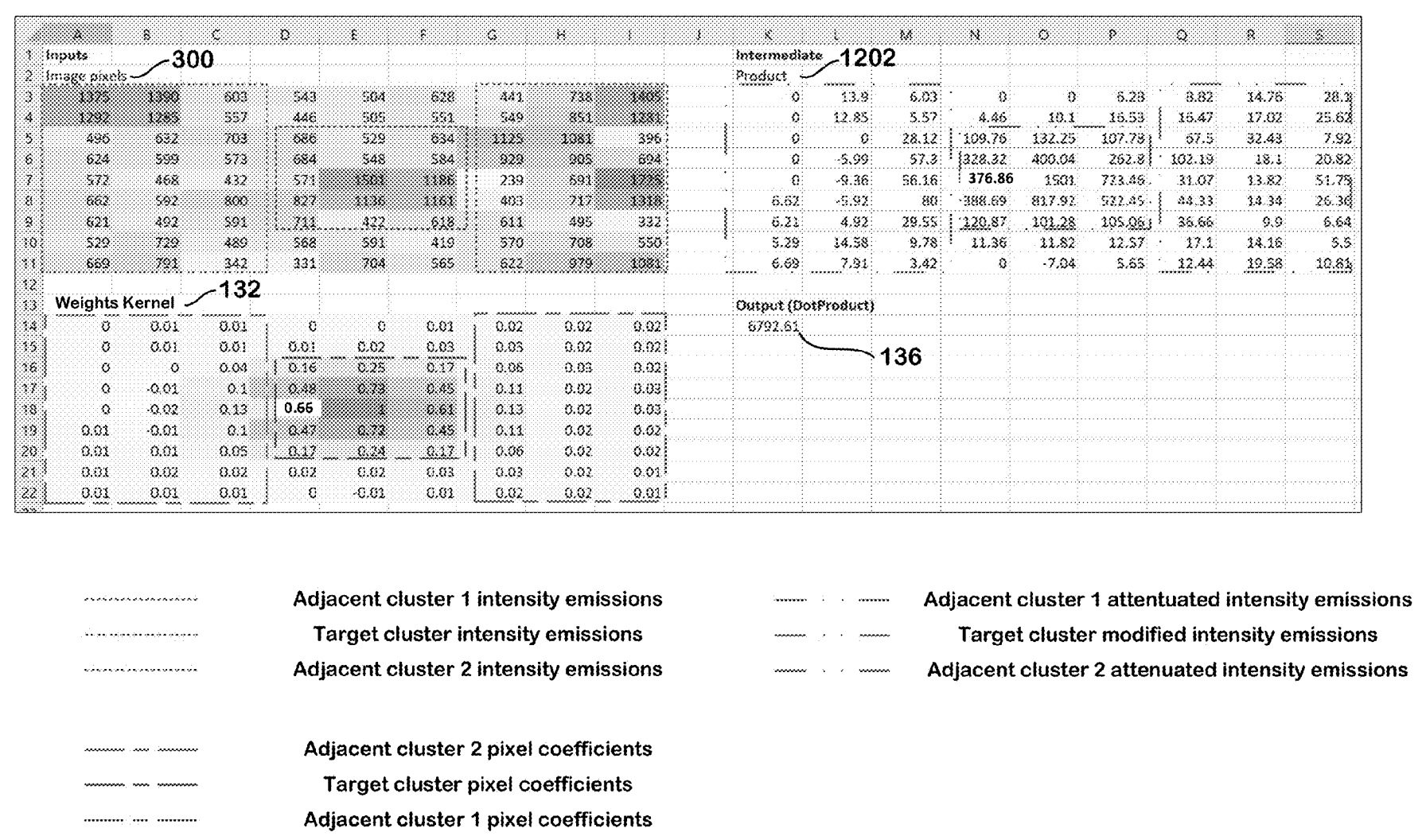
Figure 15B:
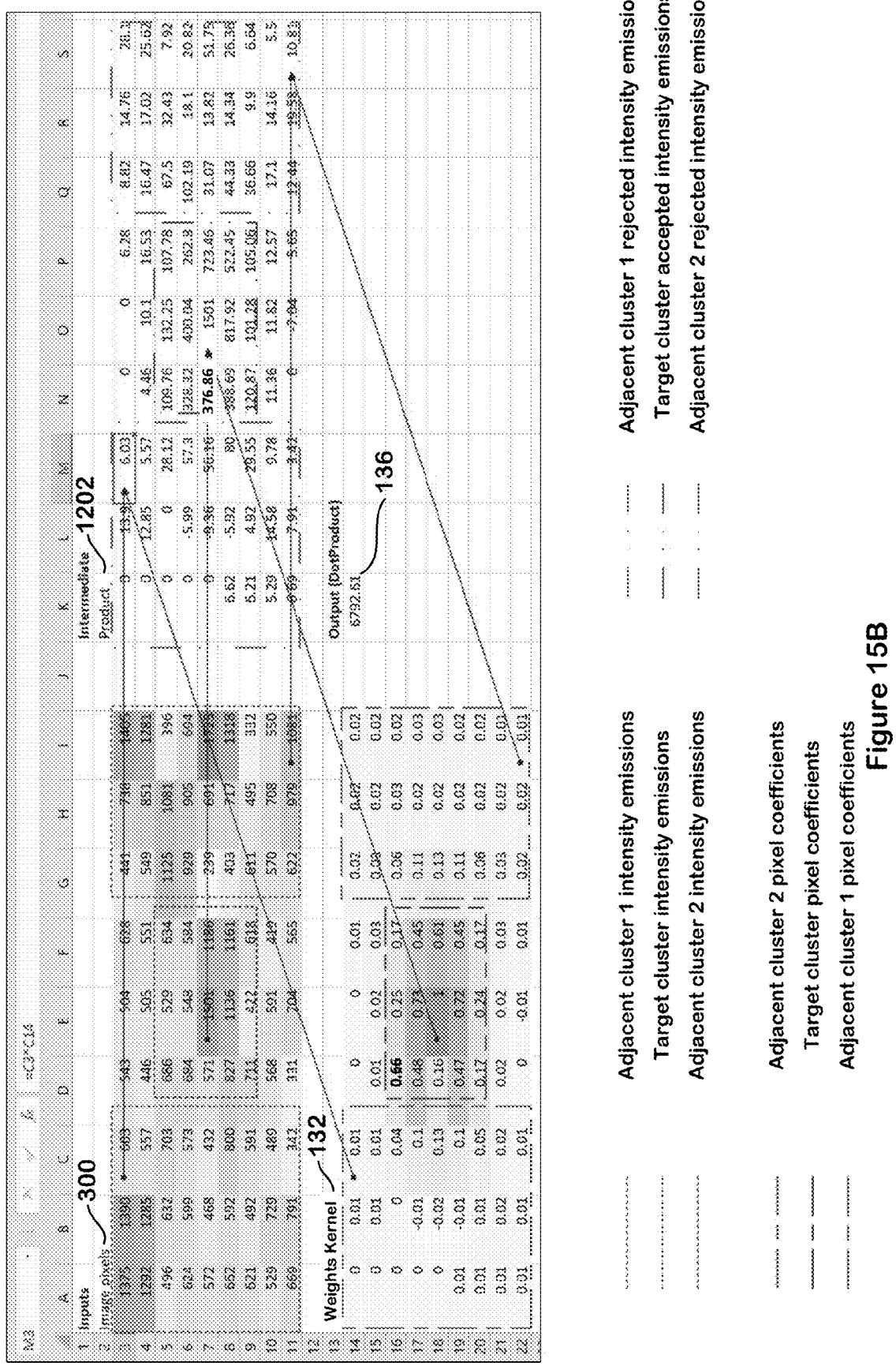

FIGS. 15A and 15B demonstrate how the interpolated pixel coefficients 1412 of the weights kernel maximize the signal-to-noise ratio and recover an underlying signal of the target cluster 1 from a signal that is corrupted by crosstalk from the clusters 2, 3, 4, and 5.

The weighted sum 136 is fed as input to the base caller 138 to produce a base call 140. The base caller 138 can be a non-neural network-based base caller or a neural network-based base caller, examples of both are described in applications incorporated herein by reference such as U.S. Patent Application No. 62/821,766 and Ser. No. 16/826,168.

In yet other implementations, the need for interpolation is eliminated by having large LUTs, each with large number of subpixel bins (e.g., 50, 75, 100, 150, 200, 300, etc. subpixel bins per LUT).

Figure 19A:
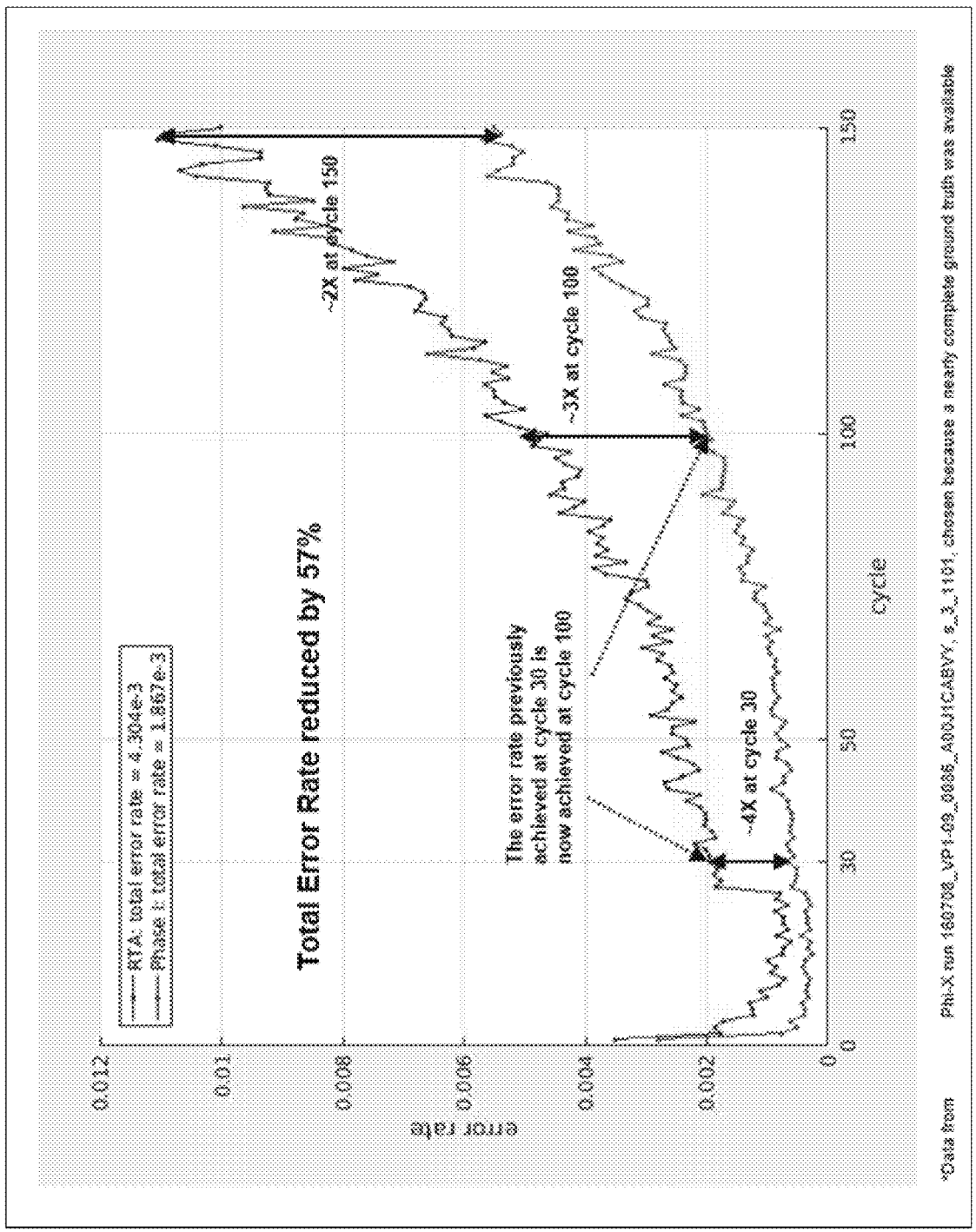

FIG. 19A shows a graph that represents base-calling error rate using images from a NovaSeq sequencer. Error rate is shown by cycle on the x axis. 0.004 on the y axis represents a base call error rate of 0.4%. The error rate here is calculated after mapping and aligning reads to a Phi-X reference, which is a high confidence ground truth set. The blue line is the legacy base caller. The red line is the improved equalizer-based base-caller 104 disclosed herein. The total error rate is reduced by 57% at the cost of limited extra computation. Base error rates at later cycles are higher due to extra noise in the system—e.g. prephasing/phasing, cluster dimming.

Performance gains in later cycles increase & this is valuable since it indicates we can support longer reads. Cycle to cycle performance variation is also markedly reduced.

Figure 19B:
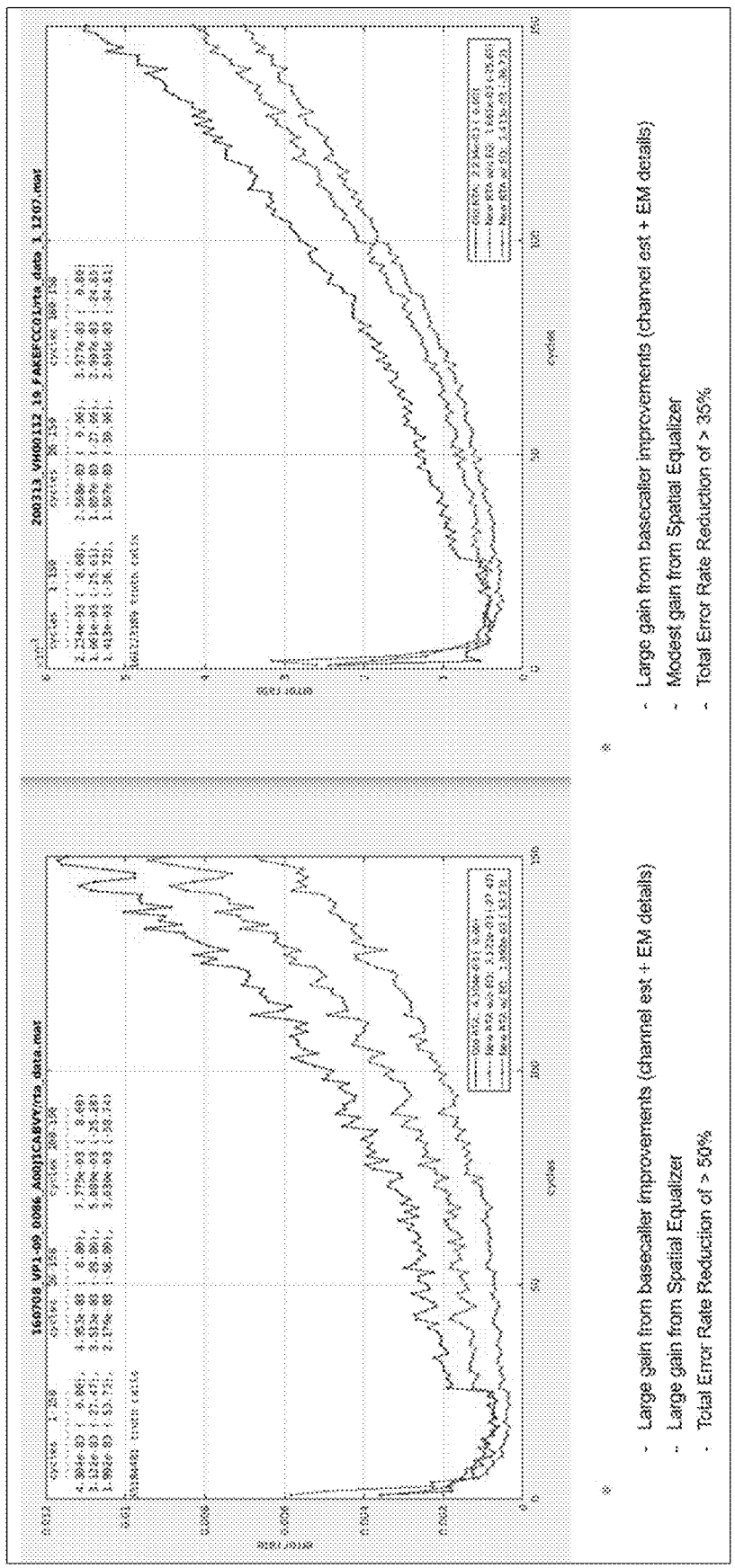

FIG. 19B shows another example of the performance results of the disclosed equalizer-based base caller 104 on sequencing data from the NovaSeq sequencer and the Vega sequencer. For the NovaSeq sequencer, the disclosed equalizer-based base caller 104 reduces the base calling error rate by more than 50%. For the Vega sequencer, the disclosed equalizer-based base caller 104 reduces the base calling error rate by more than 35%.

FIG. 19C shows another example of the performance results of the disclosed equalizer-based base caller 104 on sequencing data from the NextSeq 2000 sequencer. For the NextSeq 2000 sequencer, the disclosed equalizer-based base caller 104 reduces the base calling error rate by 10% on an average without comprising throughput.

Figure 19D:
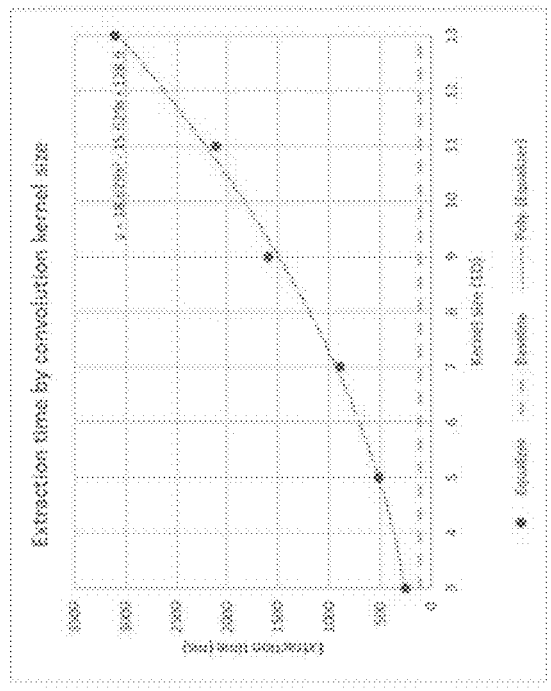

FIG. 19D shows one implementation of compute resources required by the disclosed equalizer-based base caller 104. As shown, the disclosed equalizer-based base caller 104 can be run using small number of CPU threads, ranging from two to seven threads. Thus, the disclosed equalizer-based base caller 104 is a computationally efficient base caller, which significantly reduces the base error rate, and therefore can be integrated into most existing sequencers without requiring any additional compute resources or specialized processors like GPUs, FPGAs, ASICs, and so on.

In this application, the terms "cluster", "well", "sample", and "fluorescent sample" are interchangeably used because a well contains a corresponding cluster/sample/fluorescent sample. As defined herein, "sample" and its derivatives, is used in its broadest sense and includes any specimen, culture and the like that is suspected of including a target. In some implementations, the sample comprises DNA, RNA, PNA, LNA, chimeric or hybrid forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some implementations, the source of nucleic acid material can include nucleic acids obtained from a newborn, for example as typically used for newborn screening.

The nucleic acid sample can include high molecular weight material such as genomic DNA (gDNA). The sample can include low molecular weight material such as nucleic acid molecules obtained from FFPE or archived DNA samples. In another implementation, low molecular weight material includes enzymatically or mechanically fragmented DNA. The sample can include cell-free circulating DNA. In some implementations, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some implementations, the sample can be an epidemiological, agricultural, forensic or pathogenic sample. In some implementations, the sample can include nucleic acid molecules obtained from an animal such as a human or mammalian source. In another implementation, the sample can include nucleic acid molecules obtained from a non-mammalian source such as a plant, bacteria, virus or fungus. In some implementations, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one implementation, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. The nucleic acid sample may be a purified sample or a crude DNA containing lysate, for example derived from a buccal swab, paper, fabric or other substrate that may be impregnated with saliva, blood, or other bodily fluids. As such, in some implementations, the nucleic acid sample may comprise low amounts of, or fragmented portions of DNA, such as genomic DNA. In some implementations, target sequences can be present in one or more bodily fluids including but not limited to, blood, sputum, plasma, semen, urine and serum. In some implementations, target sequences can be obtained from hair, skin, tissue samples, autopsy or remains of a victim. In some implementations, nucleic acids including one or more target sequences can be obtained from a deceased animal or human. In some implementations, target sequences can include nucleic acids obtained from non-human DNA such a microbial, plant or entomological DNA. In some implementations, target sequences or amplified target sequences are directed to purposes of human identification. In some implementations, the disclosure relates generally to methods for identifying characteristics of a forensic sample. In some implementations, the disclosure relates generally to human identification methods using one or more target specific primers disclosed herein or one or more target specific primers designed using the primer design criteria outlined herein. In one implementation, a forensic or human identification sample containing at least one target sequence can be amplified using any one or more of the target-specific primers disclosed herein or using the primer criteria outlined herein.

As used herein, the term "adjacent" when used with respect to two reaction sites means no other reaction site is located between the two reaction sites. The term "adjacent" may have a similar meaning when used with respect to adjacent detection paths and adjacent light detectors (e.g., adjacent light detectors have no other light detector therebetween). In some cases, a reaction site may not be adjacent to another reaction site, but may still be within an immediate vicinity of the other reaction site. A first reaction site may be in the immediate vicinity of a second reaction site when fluorescent emission signals from the first reaction site are detected by the light detector associated with the second reaction site. More specifically, a first reaction site may be in the immediate vicinity of a second reaction site when the light detector associated with the second reaction site detects, for example crosstalk from the first reaction site. Adjacent reaction sites can be contiguous such that they abut each other or the adjacent sites can be non-contiguous having an intervening space between.

Technical Improvements and Terminology

All literature and similar material cited in this application, including, but not limited to, patents, patent applications, articles, books, treatises, and web pages, regardless of the format of such literature and similar materials, are expressly incorporated by reference in their entirety.

In the event that one or more of the incorporated literature and similar materials differs from or contradicts this application, including but not limited to defined terms, term usage, described techniques, or the like, this application controls. Additional information about the terminology can be found in U.S. Nonprovisional patent application Ser. No. 16/826,168, entitled "Artificial Intelligence-Based Sequencing," filed 21 Mar. 2020 and U.S. Provisional Patent Application No. 62/821,766, entitled "Artificial Intelligence-Based Sequencing," filed 21 Mar. 2019.

The technology disclosed uses neural networks to improve the quality and quantity of nucleic acid sequence information that can be obtained from a nucleic acid sample such as a nucleic acid template or its complement, for instance, a DNA or RNA polynucleotide or other nucleic acid sample. Accordingly, certain implementations of the technology disclosed provide higher throughput polynucleotide sequencing, for instance, higher rates of collection of DNA or RNA sequence data, greater efficiency in sequence data collection, and/or lower costs of obtaining such sequence data, relative to previously available methodologies.

The technology disclosed uses neural networks to identify the center of a solid-phase nucleic acid cluster and to analyze optical signals that are generated during sequencing of such clusters, to discriminate unambiguously between adjacent, abutting or overlapping clusters in order to assign a sequencing signal to a single, discrete source cluster. These and related implementations thus permit retrieval of meaningful information, such as sequence data, from regions of high-density cluster arrays where useful information could not previously be obtained from such regions due to confounding effects of overlapping or very closely spaced adjacent clusters, including the effects of overlapping signals (e.g., as used in nucleic acid sequencing) emanating therefrom.

As described in greater detail below, in certain implementations there is provided a composition that comprises a solid support having immobilized thereto one or a plurality of nucleic acid clusters as provided herein. Each cluster comprises a plurality of immobilized nucleic acids of the same sequence and has an identifiable center having a detectable center label as provided herein, by which the identifiable center is distinguishable from immobilized nucleic acids in a surrounding region in the cluster. Also described herein are methods for making and using such clusters that have identifiable centers.

The presently disclosed implementations will find uses in numerous situations where advantages are obtained from the ability to identify, determine, annotate, record or otherwise assign the position of a substantially central location within a cluster, such as high-throughput nucleic acid sequencing, development of image analysis algorithms for assigning optical or other signals to discrete source clusters, and other applications where recognition of the center of an immobilized nucleic acid cluster is desirable and beneficial.

In certain implementations, the present invention contemplates methods that relate to high-throughput nucleic acid analysis such as nucleic acid sequence determination (e.g., "sequencing"). Exemplary high-throughput nucleic acid analyses include without limitation de novo sequencing, re-sequencing, whole genome sequencing, gene expression analysis, gene expression monitoring, epigenetic analysis, genome methylation analysis, allele specific primer extension (APSE), genetic diversity profiling, whole genome polymorphism discovery and analysis, single nucleotide polymorphism analysis, hybridization based sequence determination methods, and the like. One skilled in the art will appreciate that a variety of different nucleic acids can be analyzed using the methods and compositions of the present invention.

Although the implementations of the present invention are described in relation to nucleic acid sequencing, they are applicable in any field where image data acquired at different time points, spatial locations or other temporal or physical perspectives is analyzed. For example, the methods and systems described herein are useful in the fields of molecular and cell biology where image data from microarrays, biological specimens, cells, organisms and the like is acquired and at different time points or perspectives and analyzed. Images can be obtained using any number of techniques known in the art including, but not limited to, fluorescence microscopy, light microscopy, confocal microscopy, optical imaging, magnetic resonance imaging, tomography scanning or the like. As another example, the methods and systems described herein can be applied where image data obtained by surveillance, aerial or satellite imaging technologies and the like is acquired at different time points or perspectives and analyzed. The methods and systems are particularly useful for analyzing images obtained for a field of view in which the analytes being viewed remain in the same locations relative to each other in the field of view. The analytes may however have characteristics that differ in separate images, for example, the analytes may appear different in separate images of the field of view. For example, the analytes may appear different with regard to the color of a given analyte detected in different images, a change in the intensity of signal detected for a given analyte in different images, or even the appearance of a signal for a given analyte in one image and disappearance of the signal for the analyte in another image.

As used herein, the term "analyte" is intended to mean a point or area in a pattern that can be distinguished from other points or areas according to relative location. An individual analyte can include one or more molecules of a particular type. For example, an analyte can include a single target nucleic acid molecule having a particular sequence or an analyte can include several nucleic acid molecules having the same sequence (and/or complementary sequence, thereof). Different molecules that are at different analytes of a pattern can be differentiated from each other according to the locations of the analytes in the pattern. Example analytes include without limitation, wells in a substrate, beads (or other particles) in or on a substrate, projections from a substrate, ridges on a substrate, pads of gel material on a substrate, or channels in a substrate.

Any of a variety of target analytes that are to be detected, characterized, or identified can be used in an apparatus, system or method set forth herein. Exemplary analytes include, but are not limited to, nucleic acids (e.g., DNA, RNA or analogs thereof), proteins, polysaccharides, cells, antibodies, epitopes, receptors, ligands, enzymes (e.g. kinases, phosphatases or polymerases), small molecule drug candidates, cells, viruses, organisms, or the like.

The terms "analyte", "nucleic acid", "nucleic acid molecule", and "polynucleotide" are used interchangeably herein. In various implementations, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain implementations include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other implementations, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular implementations, a nucleic acid may have one or more detectable labels, as described elsewhere herein.

The terms "analyte", "cluster", "nucleic acid cluster", "nucleic acid colony", and "DNA cluster" are used interchangeably and refer to a plurality of copies of a nucleic acid template and/or complements thereof attached to a solid support. Typically and in certain preferred implementations, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

Colonies of nucleic acids can also be referred to as "nucleic acid clusters". Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. In a particular implementation, the diameter of a nucleic acid cluster is about 0.5 µm, about 1 µm, about 1.5 µm, about 2 µm, about 2.5 µm, about 3 µm, about 4 µm, about 5 µm, or about 6 µm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, $100,000/mm^2$ to $1,000,000/mm^2$ and $1,000,000/mm^2$ to $10,000,000/mm^2$.

As used herein, an "analyte" is an area of interest within a specimen or field of view. When used in connection with microarray devices or other molecular analytical devices, an analyte refers to the area occupied by similar or identical molecules. For example, an analyte can be an amplified oligonucleotide or any other group of a polynucleotide or polypeptide with a same or similar sequence. In other implementations, an analyte can be any element or group of elements that occupy a physical area on a specimen. For example, an analyte could be a parcel of land, a body of water or the like. When an analyte is imaged, each analyte will have some area. Thus, in many implementations, an analyte is not merely one pixel.

The distances between analytes can be described in any number of ways. In some implementations, the distances between analytes can be described from the center of one analyte to the center of another analyte. In other implementations, the distances can be described from the edge of one analyte to the edge of another analyte, or between the outer-most identifiable points of each analyte. The edge of an analyte can be described as the theoretical or actual physical boundary on a chip, or some point inside the boundary of the analyte. In other implementations, the distances can be described in relation to a fixed point on the specimen or in the image of the specimen.

Generally several implementations will be described herein with respect to a method of analysis. It will be understood that systems are also provided for carrying out the methods in an automated or semi-automated way. Accordingly, this disclosure provides neural network-based template generation and base calling systems, wherein the systems can include a processor; a storage device; and a program for image analysis, the program including instructions for carrying out one or more of the methods set forth herein. Accordingly, the methods set forth herein can be carried out on a computer, for example, having components set forth herein or otherwise known in the art.

The methods and systems set forth herein are useful for analyzing any of a variety of objects. Particularly useful objects are solid supports or solid-phase surfaces with attached analytes. The methods and systems set forth herein provide advantages when used with objects having a repeating pattern of analytes in an xy plane. An example is a microarray having an attached collection of cells, viruses, nucleic acids, proteins, antibodies, carbohydrates, small molecules (such as drug candidates), biologically active molecules or other analytes of interest.

An increasing number of applications have been developed for arrays with analytes having biological molecules such as nucleic acids and polypeptides. Such microarrays typically include deoxyribonucleic acid (DNA) or ribonucleic acid (RNA) probes. These are specific for nucleotide sequences present in humans and other organisms. In certain applications, for example, individual DNA or RNA probes can be attached at individual analytes of an array. A test sample, such as from a known person or organism, can be exposed to the array, such that target nucleic acids (e.g., gene fragments, mRNA, or amplicons thereof) hybridize to complementary probes at respective analytes in the array. The probes can be labeled in a target specific process (e.g., due to labels present on the target nucleic acids or due to enzymatic labeling of the probes or targets that are present in hybridized form at the analytes). The array can then be examined by scanning specific frequencies of light over the analytes to identify which target nucleic acids are present in the sample.

Biological microarrays may be used for genetic sequencing and similar applications. In general, genetic sequencing comprises determining the order of nucleotides in a length of target nucleic acid, such as a fragment of DNA or RNA. Relatively short sequences are typically sequenced at each analyte, and the resulting sequence information may be used in various bioinformatics methods to logically fit the sequence fragments together so as to reliably determine the sequence of much more extensive lengths of genetic material from which the fragments were derived. Automated, computer-based algorithms for characteristic fragments have been developed, and have been used more recently in genome mapping, identification of genes and their function, and so forth. Microarrays are particularly useful for characterizing genomic content because a large number of variants are present and this supplants the alternative of performing many experiments on individual probes and targets. The microarray is an ideal format for performing such investigations in a practical manner.

Any of a variety of analyte arrays (also referred to as "microarrays") known in the art can be used in a method or system set forth herein. A typical array contains analytes, each having an individual probe or a population of probes. In the latter case, the population of probes at each analyte is typically homogenous having a single species of probe. For example, in the case of a nucleic acid array, each analyte can have multiple nucleic acid molecules each having a common sequence. However, in some implementations the populations at each analyte of an array can be heterogeneous. Similarly, protein arrays can have analytes with a single protein or a population of proteins typically, but not always, having the same amino acid sequence. The probes can be attached to the surface of an array for example, via covalent linkage of the probes to the surface or via non-covalent interaction(s) of the probes with the surface. In some implementations, probes, such as nucleic acid molecules, can be attached to a surface via a gel layer as described, for example, in U.S. patent application Ser. No. 13/784,368 and US Pat. App. Pub. No. 2011/0059865 A1, each of which is incorporated herein by reference.

Example arrays include, without limitation, a BeadChip Array available from Illumina, Inc. (San Diego, Calif.) or others such as those where probes are attached to beads that are present on a surface (e.g. beads in wells on a surface) such as those described in U.S. Pat. Nos. 6,266,459; 6,355, 431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in a method or system according to some implementations of the present disclosure. An example spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; WO 91/06678; WO 07/123744; U.S. Pat. Nos. 7,329,492; 7,211,414; 7,315,019; 7,405,281, or 7,057,026; or US Pat. App. Pub. No. 2008/0108082 A1, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US Pat. App. Pub. No. 2005/0130173 or US Pat. App. Pub. No. 2005/0064460, each of which is incorporated herein by reference in its entirety.

Arrays used for nucleic acid sequencing often have random spatial patterns of nucleic acid analytes. For example, HiSeq or MiSeq sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Example patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The analytes of such patterned arrays can be used to capture a single nucleic acid template molecule to seed subsequent formation of a homogenous colony, for example, via bridge amplification. Such patterned arrays are particularly useful for nucleic acid sequencing applications.

The size of an analyte on an array (or other object used in a method or system herein) can be selected to suit a particular application. For example, in some implementations, an analyte of an array can have a size that accommodates only a single nucleic acid molecule. A surface having a plurality of analytes in this size range is useful for constructing an array of molecules for detection at single molecule resolution. Analytes in this size range are also useful for use in arrays having analytes that each contain a colony of nucleic acid molecules. Thus, the analytes of an array can each have an area that is no larger than about 1 mm$^2$, no larger than about 500 µm$^2$, no larger than about 100 µm$^2$, no larger than about 10 µm$^2$, no larger than about 1 µm$^2$, no larger than about 500 nm$^2$, or no larger than about 100 nm$^2$, no larger than about 10 nm$^2$, no larger than about 5 nm$^2$, or no larger than about 1 nm$^2$. Alternatively or additionally, the analytes of an array will be no smaller than about 1 mm$^2$, no smaller than about 500 µm$^2$, no smaller than about 100 µm$^2$, no smaller than about 10 µm$^2$, no smaller than about 1 µm$^2$, no smaller than about 500 nm$^2$, no smaller than about 100 nm$^2$, no smaller than about 10 nm$^2$, no smaller than about 5 nm$^2$, or no smaller than about 1 nm$^2$. Indeed, an analyte can have a size that is in a range between an upper and lower limit selected from those exemplified above. Although several size ranges for analytes of a surface have been exemplified with respect to nucleic acids and on the scale of nucleic acids, it will be understood that analytes in these size ranges can be used for applications that do not include nucleic acids. It will be further understood that the size of the analytes need not necessarily be confined to a scale used for nucleic acid applications.

For implementations that include an object having a plurality of analytes, such as an array of analytes, the analytes can be discrete, being separated with spaces between each other. An array useful in the invention can have analytes that are separated by edge to edge distance of at most 100 µm, 50 µm, 10 µm, 5 µm, 1 µm, 0.5 µm, or less. Alternatively or additionally, an array can have analytes that are separated by an edge to edge distance of at least 0.5 µm, 1 µm, 5 µm, 10 µm, 50 µm, 100 µm, or more. These ranges can apply to the average edge to edge spacing for analytes as well as to the minimum or maximum spacing.

In some implementations the analytes of an array need not be discrete and instead neighboring analytes can abut each other. Whether or not the analytes are discrete, the size of the analytes and/or pitch of the analytes can vary such that arrays can have a desired density. For example, the average analyte pitch in a regular pattern can be at most 100 µm, 50 µm, 10 µm, 5 µm, 1 µm, 0.5 or less. Alternatively or additionally, the average analyte pitch in a regular pattern can be at least 0.5 µm, 1 µm, 5 µm, 10 µm, 50 µm, 100 µm, or more. These ranges can apply to the maximum or minimum pitch for a regular pattern as well. For example, the maximum analyte pitch for a regular pattern can be at most 100 µm, 50 µm, 10 µm, 5 µm, 1 µm, 0.5 µm, or less; and/or the minimum analyte pitch in a regular pattern can be at least 0.5 µm, 1 µm, 5 µm, 10 µm, 5µm, 100 µm, or more.

The density of analytes in an array can also be understood in terms of the number of analytes present per unit area. For example, the average density of analytes for an array can be at least about $1\times10^3$ analytes/mm$^2$, $1\times10^4$ analytes/mm$^2$, $1\times10^5$ analytes/mm$^2$, $1\times10^6$ analytes/mm$^2$, $1\times10^7$ analytes/mm$^2$, $1\times10^8$ analytes/mm$^2$, or $1\times10^9$ analytes/mm$^2$, or higher. Alternatively or additionally the average density of analytes for an array can be at most about $1\times10^9$ analytes/mm$^2$, $1\times10^8$ analytes/mm$^2$, $1\times10^7$ analytes/mm$^2$, $1\times10^6$ analytes/mm$^2$, $1\times10^5$ analytes/mm$^2$, $1\times10^4$ analytes/mm$^2$, or $1\times10^3$ analytes/mm$^2$, or less.

The above ranges can apply to all or part of a regular pattern including, for example, all or part of an array of analytes.

The analytes in a pattern can have any of a variety of shapes. For example, when observed in a two dimensional plane, such as on the surface of an array, the analytes can appear rounded, circular, oval, rectangular, square, symmetric, asymmetric, triangular, polygonal, or the like. The analytes can be arranged in a regular repeating pattern including, for example, a hexagonal or rectilinear pattern. A pattern can be selected to achieve a desired level of packing. For example, round analytes are optimally packed in a hexagonal arrangement. Of course other packing arrangements can also be used for round analytes and vice versa.

A pattern can be characterized in terms of the number of analytes that are present in a subset that forms the smallest geometric unit of the pattern. The subset can include, for example, at least about 2, 3, 4, 5, 6, 10 or more analytes. Depending upon the size and density of the analytes the geometric unit can occupy an area of less than 1 mm$^2$, 500 μm$^2$, 100 μm$^2$, 50 μm$^2$, 10 μm$^2$, 1 μm$^2$, 500 nm$^2$, 100 nm$^2$, 50 nm$^2$, 10 nm$^2$, or less. Alternatively or additionally, the geometric unit can occupy an area of greater than 10 nm$^2$, 50 nm$^2$, 100 nm$^2$, 500 nm$^2$, 1 μm$^2$, 10 μm$^2$, 50 μm$^2$, 100 μm$^2$, 500 μm$^2$, 1 mm$^2$, or more. Characteristics of the analytes in a geometric unit, such as shape, size, pitch and the like, can be selected from those set forth herein more generally with regard to analytes in an array or pattern.

An array having a regular pattern of analytes can be ordered with respect to the relative locations of the analytes but random with respect to one or more other characteristic of each analyte. For example, in the case of a nucleic acid array, the nuclei acid analytes can be ordered with respect to their relative locations but random with respect to one's knowledge of the sequence for the nucleic acid species present at any particular analyte. As a more specific example, nucleic acid arrays formed by seeding a repeating pattern of analytes with template nucleic acids and amplifying the template at each analyte to form copies of the template at the analyte (e.g., via cluster amplification or bridge amplification) will have a regular pattern of nucleic acid analytes but will be random with regard to the distribution of sequences of the nucleic acids across the array. Thus, detection of the presence of nucleic acid material generally on the array can yield a repeating pattern of analytes, whereas sequence specific detection can yield non-repeating distribution of signals across the array.

It will be understood that the description herein of patterns, order, randomness and the like pertain not only to analytes on objects, such as analytes on arrays, but also to analytes in images. As such, patterns, order, randomness and the like can be present in any of a variety of formats that are used to store, manipulate or communicate image data including, but not limited to, a computer readable medium or computer component such as a graphical user interface or other output device.

As used herein, the term "image" is intended to mean a representation of all or part of an object. The representation can be an optically detected reproduction. For example, an image can be obtained from fluorescent, luminescent, scatter, or absorption signals. The part of the object that is present in an image can be the surface or other xy plane of the object. Typically, an image is a 2 dimensional representation, but in some cases information in the image can be derived from 3 or more dimensions. An image need not include optically detected signals. Non-optical signals can be present instead. An image can be provided in a computer readable format or medium such as one or more of those set forth elsewhere herein.

As used herein, "image" refers to a reproduction or representation of at least a portion of a specimen or other object. In some implementations, the reproduction is an optical reproduction, for example, produced by a camera or other optical detector. The reproduction can be a non-optical reproduction, for example, a representation of electrical signals obtained from an array of nanopore analytes or a representation of electrical signals obtained from an ion-sensitive CMOS detector. In particular implementations non-optical reproductions can be excluded from a method or apparatus set forth herein. An image can have a resolution capable of distinguishing analytes of a specimen that are present at any of a variety of spacings including, for example, those that are separated by less than 100 μm, 50 μm, 10 μm, 5 μm, 1 μm or 0.5 μm.

As used herein, "acquiring", "acquisition" and like terms refer to any part of the process of obtaining an image file. In some implementations, data acquisition can include generating an image of a specimen, looking for a signal in a specimen, instructing a detection device to look for or generate an image of a signal, giving instructions for further analysis or transformation of an image file, and any number of transformations or manipulations of an image file.

As used herein, the term "template" refers to a representation of the location or relation between signals or analytes. Thus, in some implementations, a template is a physical grid with a representation of signals corresponding to analytes in a specimen. In some implementations, a template can be a chart, table, text file or other computer file indicative of locations corresponding to analytes. In implementations presented herein, a template is generated in order to track the location of analytes of a specimen across a set of images of the specimen captured at different reference points. For example, a template could be a set of x,y coordinates or a set of values that describe the direction and/or distance of one analyte with respect to another analyte.

As used herein, the term "specimen" can refer to an object or area of an object of which an image is captured. For example, in implementations where images are taken of the surface of the earth, a parcel of land can be a specimen. In other implementations where the analysis of biological molecules is performed in a flow cell, the flow cell may be divided into any number of subdivisions, each of which may be a specimen. For example, a flow cell may be divided into various flow channels or lanes, and each lane can be further divided into 2, 3, 4, 5, 6, 7, 8, 9, 10, 20, 30, 40, 50, 6070, 80, 90, 100, 110, 120, 140, 160, 180, 200, 400, 600, 800, 1000 or more separate regions that are imaged. One example of a flow cell has 8 lanes, with each lane divided into 120 specimens or tiles. In another implementation, a specimen may be made up of a plurality of tiles or even an entire flow cell. Thus, the image of each specimen can represent a region of a larger surface that is imaged.

It will be appreciated that references to ranges and sequential number lists described herein include not only the enumerated number but all real numbers between the enumerated numbers.

As used herein, a "reference point" refers to any temporal or physical distinction between images. In a preferred implementation, a reference point is a time point. In a more preferred implementation, a reference point is a time point or cycle during a sequencing reaction. However, the term "reference point" can include other aspects that distinguish or separate images, such as angle, rotational, temporal, or other aspects that can distinguish or separate images.

As used herein, a "subset of images" refers to a group of images within a set. For example, a subset may contain 1, 2, 3, 4, 6, 8, 10, 12, 14, 16, 18, 20, 30, 40, 50, 60 or any number of images selected from a set of images. In particular implementations, a subset may contain no more than 1, 2, 3, 4, 6, 8, 10, 12, 14, 16, 18, 20, 30, 40, 50, 60 or any number of images selected from a set of images. In a preferred implementation, images are obtained from one or more sequencing cycles with four images correlated to each cycle. Thus, for example, a subset could be a group of 16 images obtained through four cycles.

A base refers to a nucleotide base or nucleotide, A (adenine), C (cytosine), T (thymine), or G (guanine). This application uses "base(s)" and "nucleotide(s)" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding subsequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects. The application uses "read(s)" and "sequence read(s)" interchangeably.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual. In other implementations, the "genome" also covers so-called "graph genomes", which use a particular storage format and representation of the genome sequence. In one implementation, graph genomes store data in a linear file. In another implementation, the graph genomes refer to a representation where alternative sequences (e.g., different copies of a chromosome with small differences) are stored as different paths in a graph. Additional information regarding graph genome implementations can be found in https://www.biorxiv.org/content/biorxiv/early/2018/03/20/194530.full.pdf, the content of which is hereby incorporated herein by reference in its entirety.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, the DNA sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105× with 98% of targeted bases covered >100×.

The terms "base call quality score" or "Q score" refer to a PHRED-scaled probability ranging from 0-50 inversely proportional to the probability that a single sequenced base is correct. For example, a T base call with Q of 20 is considered likely correct with a probability of 99.99%. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Regarding "strandedness" (or DNA strandedness), the genetic message in DNA can be represented as a string of the letters A, G, C, and T. For example, 5'-AGGACA-3'. Often, the sequence is written in the direction shown here, i.e., with the 5' end to the left and the 3' end to the right. DNA may sometimes occur as single-stranded molecule (as in certain viruses), but normally we find DNA as a double-stranded unit. It has a double helical structure with two antiparallel strands. In this case, the word "antiparallel" means that the two strands run in parallel, but have opposite polarity. The double-stranded DNA is held together by pairing between bases and the pairing is always such that adenine (A) pairs with thymine (T) and cytosine (C) pairs with guanine (G). This pairing is referred to as complementarity, and one strand of DNA is said to be the complement of the other. The double-stranded DNA may thus be represented as two strings, like this: 5'-AGGACA-3' and 3'-TCCTGT-5'. Note that the two strands have opposite polarity. Accordingly, the strandedness of the two DNA strands can be referred to as the reference strand and its complement, forward and reverse strands, top and bottom strands, sense and antisense strands, or Watson and Crick strands.

The reads alignment (also called reads mapping) is the process of figuring out where in the genome a sequence is from. Once the alignment is performed, the "mapping quality" or the "mapping quality score (MAPQ)" of a given read quantifies the probability that its position on the genome is correct. The mapping quality is encoded in the phred scale where P is the probability that the alignment is not correct. The probability is calculated as: $P=10^{(-MAPQ/10)}$, where MAPQ is the mapping quality. For example, a mapping quality of 40=10 to the power of −4, meaning that there is a 0.01% chance that the read was aligned incorrectly. The mapping quality is therefore associated with several alignment factors, such as the base quality of the read, the complexity of the reference genome, and the paired-end information. Regarding the first, if the base quality of the read is low, it means that the observed sequence might be wrong and thus its alignment is wrong. Regarding the second, the mappability refers to the complexity of the genome. Repeated regions are more difficult to map and reads falling in these regions usually get low mapping quality. In this context, the MAPQ reflects the fact that the reads are not uniquely aligned and that their real origin cannot be determined. Regarding the third, in case of paired-end sequencing data, concordant pairs are more likely to be well aligned. The higher is the mapping quality, the better is the alignment. A read aligned with a good mapping quality usually means that the read sequence was good and was aligned with few mismatches in a high mappability region. The MAPQ value can be used as a quality control of the alignment results. The proportion of reads aligned with an MAPQ higher than 20 is usually for downstream analysis.

As used herein, a "signal" refers to a detectable event such as an emission, preferably light emission, for example, in an image. Thus, in preferred implementations, a signal can represent any detectable light emission that is captured in an image (i.e., a "spot"). Thus, as used herein, "signal" can refer to both an actual emission from an analyte of the specimen, and can refer to a spurious emission that does not correlate to an actual analyte. Thus, a signal could arise from noise and could be later discarded as not representative of an actual analyte of a specimen.

As used herein, the term "clump" refers to a group of signals. In particular implementations, the signals are derived from different analytes. In a preferred implementation, a signal clump is a group of signals that cluster together. In a more preferred implementation, a signal clump represents a physical region covered by one amplified oligonucleotide. Each signal clump should be ideally observed as several signals (one per template cycle, and possibly more due to cross-talk). Accordingly, duplicate signals are detected where two (or more) signals are included in a template from the same clump of signals.

As used herein, terms such as "minimum," "maximum," "minimize," "maximize" and grammatical variants thereof can include values that are not the absolute maxima or minima. In some implementations, the values include near maximum and near minimum values. In other implementations, the values can include local maximum and/or local minimum values. In some implementations, the values include only absolute maximum or minimum values.

As used herein, "cross-talk" refers to the detection of signals in one image that are also detected in a separate image. In a preferred implementation, cross-talk can occur when an emitted signal is detected in two separate detection channels. For example, where an emitted signal occurs in one color, the emission spectrum of that signal may overlap with another emitted signal in another color. In a preferred implementation, fluorescent molecules used to indicate the presence of nucleotide bases A, C, G and T are detected in separate channels. However, because the emission spectra of A and C overlap, some of the C color signal may be detected during detection using the A color channel. Accordingly, cross-talk between the A and C signals allows signals from one color image to appear in the other color image. In some implementations, G and T cross-talk. In some implementations, the amount of cross-talk between channels is asymmetric. It will be appreciated that the amount of cross-talk between channels can be controlled by, among other things, the selection of signal molecules having an appropriate emission spectrum as well as selection of the size and wavelength range of the detection channel.

As used herein, "register", "registering", "registration" and like terms refer to any process to correlate signals in an image or data set from a first time point or perspective with signals in an image or data set from another time point or perspective. For example, registration can be used to align signals from a set of images to form a template. In another example, registration can be used to align signals from other images to a template. One signal may be directly or indirectly registered to another signal. For example, a signal from image "S" may be registered to image "G" directly. As another example, a signal from image "N" may be directly registered to image "G", or alternatively, the signal from image "N" may be registered to image "S", which has previously been registered to image "G". Thus, the signal from image "N" is indirectly registered to image "G".

As used herein, the term "fiducial" is intended to mean a distinguishable point of reference in or on an object. The point of reference can be, for example, a mark, second object, shape, edge, area, irregularity, channel, pit, post or the like. The point of reference can be present in an image of the object or in another data set derived from detecting the object. The point of reference can be specified by an x and/or y coordinate in a plane of the object. Alternatively or additionally, the point of reference can be specified by a z coordinate that is orthogonal to the xy plane, for example, being defined by the relative locations of the object and a detector. One or more coordinates for a point of reference can be specified relative to one or more other analytes of an object or of an image or other data set derived from the object.

As used herein, the term "optical signal" is intended to include, for example, fluorescent, luminescent, scatter, or absorption signals. Optical signals can be detected in the ultraviolet (UV) range (about 200 to 390 nm), visible (VIS) range (about 391 to 770 nm), infrared (IR) range (about 0.771 to 25 microns), or other range of the electromagnetic spectrum. Optical signals can be detected in a way that excludes all or part of one or more of these ranges.

As used herein, the term "signal level" is intended to mean an amount or quantity of detected energy or coded information that has a desired or predefined characteristic. For example, an optical signal can be quantified by one or more of intensity, wavelength, energy, frequency, power, luminance or the like. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

As used herein, the term "simulate" is intended to mean creating a representation or model of a physical thing or action that predicts characteristics of the thing or action. The representation or model can in many cases be distinguishable from the thing or action. For example, the representation or model can be distinguishable from a thing with respect to one or more characteristic such as color, intensity of signals detected from all or part of the thing, size, or shape. In particular implementations, the representation or model can be idealized, exaggerated, muted, or incomplete when compared to the thing or action. Thus, in some implementations, a representation of model can be distinguishable from the thing or action that it represents, for example, with respect to at least one of the characteristics set forth above. The representation or model can be provided in a computer readable format or medium such as one or more of those set forth elsewhere herein.

As used herein, the term "specific signal" is intended to mean detected energy or coded information that is selectively observed over other energy or information such as background energy or information. For example, a specific signal can be an optical signal detected at a particular intensity, wavelength or color; an electrical signal detected at a particular frequency, power or field strength; or other signals known in the art pertaining to spectroscopy and analytical detection.

As used herein, the term "swath" is intended to mean a rectangular portion of an object. The swath can be an elongated strip that is scanned by relative movement between the object and a detector in a direction that is parallel to the longest dimension of the strip. Generally, the width of the rectangular portion or strip will be constant along its full length. Multiple swaths of an object can be parallel to each other. Multiple swaths of an object can be adjacent to each other, overlapping with each other, abutting each other, or separated from each other by an interstitial area.

As used herein, the term "variance" is intended to mean a difference between that which is expected and that which is observed or a difference between two or more observations. For example, variance can be the discrepancy between an expected value and a measured value.

Variance can be represented using statistical functions such as standard deviation, the square of standard deviation, coefficient of variation or the like.

As used herein, the term "xy coordinates" is intended to mean information that specifies location, size, shape, and/or orientation in an xy plane. The information can be, for example, numerical coordinates in a Cartesian system. The coordinates can be provided relative to one or both of the x and y axes or can be provided relative to another location in the xy plane. For example, coordinates of a analyte of an object can specify the location of the analyte relative to location of a fiducial or other analyte of the object.

As used herein, the term "xy plane" is intended to mean a 2 dimensional area defined by straight line axes x and y.

When used in reference to a detector and an object observed by the detector, the area can be further specified as being orthogonal to the direction of observation between the detector and object being detected.

As used herein, the term "z coordinate" is intended to mean information that specifies the location of a point, line or area along an axes that is orthogonal to an xy plane. In particular implementations, the z axis is orthogonal to an area of an object that is observed by a detector.

For example, the direction of focus for an optical system may be specified along the z axis.

In some implementations, acquired signal data is transformed using an affine transformation. In some such implementations, template generation makes use of the fact that the affine transforms between color channels are consistent between runs. Because of this consistency, a set of default offsets can be used when determining the coordinates of the analytes in a specimen. For example, a default offsets file can contain the relative transformation (shift, scale, skew) for the different channels relative to one channel, such as the A channel. In other implementations, however, the offsets between color channels drift during a run and/or between runs, making offset-driven template generation difficult. In such implementations, the methods and systems provided herein can utilize offset-less template generation, which is described further below.

In some aspects of the above implementations, the system can comprise a flow cell. In some aspects, the flow cell comprises lanes, or other configurations, of tiles, wherein at least some of the tiles comprise one or more arrays of analytes. In some aspects, the analytes comprise a plurality of molecules such as nucleic acids. In certain aspects, the flow cell is configured to deliver a labeled nucleotide base to an array of nucleic acids, thereby extending a primer hybridized to a nucleic acid within a analyte so as to produce a signal corresponding to a analyte comprising the nucleic acid. In preferred implementations, the nucleic acids within a analyte are identical or substantially identical to each other.

In some of the systems for image analysis described herein, each image in the set of images includes color signals, wherein a different color corresponds to a different nucleotide base. In some aspects, each image of the set of images comprises signals having a single color selected from at least four different colors. In some aspects, each image in the set of images comprises signals having a single color selected from four different colors. In some of the systems described herein, nucleic acids can be sequenced by providing four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, the system comprises a flow cell that is configured to deliver additional labeled nucleotide bases to the array of molecules, thereby producing a plurality of cycles of color images.

In preferred implementations, the methods provided herein can include determining whether a processor is actively acquiring data or whether the processor is in a low activity state. Acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. Accordingly, as used herein, the term low activity state refers to the processing capacity of a processor at a given time. In some implementations, a low activity state occurs when a processor is not acquiring and/or storing data. In some implementations, a low activity state occurs when some data acquisition and/or storage is taking place, but additional processing capacity remains such that image analysis can occur at the same time without interfering with other functions.

As used herein, "identifying a conflict" refers to identifying a situation where multiple processes compete for resources. In some such implementations, one process is given priority over another process. In some implementations, a conflict may relate to the need to give priority for allocation of time, processing capacity, storage capacity or any other resource for which priority is given. Thus, in some implementations, where processing time or capacity is to be distributed between two processes such as either analyzing a data set and acquiring and/or storing the data set, a conflict between the two processes exists and can be resolved by giving priority to one of the processes.

Also provided herein are systems for performing image analysis. The systems can include a processor; a storage capacity; and a program for image analysis, the program comprising instructions for processing a first data set for storage and the second data set for analysis, wherein the processing comprises acquiring and/or storing the first data set on the storage device and analyzing the second data set when the processor is not acquiring the first data set. In certain aspects, the program includes instructions for identifying at least one instance of a conflict between acquiring and/or storing the first data set and analyzing the second data set; and resolving the conflict in favor of acquiring and/or storing image data such that acquiring and/or storing the first data set is given priority. In certain aspects, the first data set comprises image files obtained from an optical imaging device. In certain aspects, the system further comprises an optical imaging device. In some aspects, the optical imaging device comprises a light source and a detection device.

As used herein, the term "program" refers to instructions or commands to perform a task or process. The term "program" can be used interchangeably with the term module. In certain implementations, a program can be a compilation of various instructions executed under the same set of commands. In other implementations, a program can refer to a discrete batch or file.

Set forth below are some of the surprising effects of utilizing the methods and systems for performing image analysis set forth herein. In some sequencing implementations, an important measure of a sequencing system's utility is its overall efficiency. For example, the amount of mappable data produced per day and the total cost of installing and running the instrument are important aspects of an economical sequencing solution. To reduce the time to generate mappable data and to increase the efficiency of the system, real-time base calling can be enabled on an instrument computer and can run in parallel with sequencing chemistry and imaging. This allows much of the data processing and analysis to be completed before the sequencing chemistry finishes. Additionally, it can reduce the storage required for intermediate data and limit the amount of data that needs to travel across the network.

While sequence output has increased, the data per run transferred from the systems provided herein to the network and to secondary analysis processing hardware has substantially decreased. By transforming data on the instrument computer (acquiring computer), network loads are dramatically reduced. Without these on-instrument, off-network data reduction techniques, the image output of a fleet of DNA sequencing instruments would cripple most networks.

The widespread adoption of the high-throughput DNA sequencing instruments has been driven in part by ease of use, support for a range of applications, and suitability for virtually any lab environment. The highly efficient algorithms presented herein allow significant analysis functionality to be added to a simple workstation that can control sequencing instruments. This reduction in the requirements for computational hardware has several practical benefits that will become even more important as sequencing output levels continue to increase. For example, by performing image analysis and base calling on a simple tower, heat production, laboratory footprint, and power consumption are kept to a minimum. In contrast, other commercial sequencing technologies have recently ramped up their computing infrastructure for primary analysis, with up to five times more processing power, leading to commensurate increases in heat output and power consumption. Thus, in some implementations, the computational efficiency of the methods and systems provided herein enables customers to increase their sequencing throughput while keeping server hardware expenses to a minimum.

Accordingly, in some implementations, the methods and/or systems presented herein act as a state machine, keeping track of the individual state of each specimen, and when it detects that a specimen is ready to advance to the next state, it does the appropriate processing and advances the specimen to that state. A more detailed example of how the state machine monitors a file system to determine when a specimen is ready to advance to the next state according to a preferred implementation is set forth in Example 1 below.

In preferred implementations, the methods and systems provided herein are multi-threaded and can work with a configurable number of threads. Thus, for example in the context of nucleic acid sequencing, the methods and systems provided herein are capable of working in the background during a live sequencing run for real-time analysis, or it can be run using a pre-existing set of image data for off-line analysis. In certain preferred implementations, the methods and systems handle multi-threading by giving each thread its own subset of specimen for which it is responsible. This minimizes the possibility of thread contention.

A method of the present disclosure can include a step of obtaining a target image of an object using a detection apparatus, wherein the image includes a repeating pattern of analytes on the object. Detection apparatus that are capable of high resolution imaging of surfaces are particularly useful. In particular implementations, the detection apparatus will have sufficient resolution to distinguish analytes at the densities, pitches, and/or analyte sizes set forth herein.

Particularly useful are detection apparatus capable of obtaining images or image data from surfaces. Example detectors are those that are configured to maintain an object and detector in a static relationship while obtaining an area image. Scanning apparatus can also be used. For example, an apparatus that obtains sequential area images (e.g., so called 'step and shoot' detectors) can be used. Also useful are devices that continually scan a point or line over the surface of an object to accumulate data to construct an image of the surface. Point scanning detectors can be configured to scan a point (i.e., a small detection area) over the surface of an object via a raster motion in the x-y plane of the surface. Line scanning detectors can be configured to scan a line along the y dimension of the surface of an object, the longest dimension of the line occurring along the x dimension. It will be understood that the detection device, object or both can be moved to achieve scanning detection. Detection apparatus that are particularly useful, for example in nucleic acid sequencing applications, are described in US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference.

The implementations disclosed herein may be implemented as a method, apparatus, system or article of manufacture using programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), coarse grained reconfigurable architectures (CGRAs), application-specific integrated circuits (ASICs), complex programmable logic devices (CPLDs), programmable logic arrays (PLAs), microprocessors, or other similar processing devices. In particular implementations, information or algorithms set forth herein are present in non-transient storage media.

In particular implementations, a computer implemented method set forth herein can occur in real time while multiple images of an object are being obtained. Such real time analysis is particularly useful for nucleic acid sequencing applications wherein an array of nucleic acids is subjected to repeated cycles of fluidic and detection steps. Analysis of the sequencing data can often be computationally intensive such that it can be beneficial to perform the methods set forth herein in real time or in the background while other data acquisition or analysis algorithms are in process. Example real time analysis methods that can be used with the present methods are those used for the MiSeq and HiSeq sequencing devices commercially available from Illumina, Inc.

(San Diego, Calif.) and/or described in US Pat. App. Pub. No. 2012/0020537 A1, which is incorporated herein by reference.

An example data analysis system, formed by one or more programmed computers, with programming being stored on one or more machine readable media with code executed to carry out one or more steps of methods described herein. In one implementation, for example, the system includes an interface designed to permit networking of the system to one or more detection systems (e.g., optical imaging systems) that are configured to acquire data from target objects. The interface may receive and condition data, where appropriate. In particular implementations the detection system will output digital image data, for example, image data that is representative of individual picture elements or pixels that, together, form an image of an array or other object. A processor processes the received detection data in accordance with a one or more routines defined by processing code. The processing code may be stored in various types of memory circuitry.

In accordance with the presently contemplated implementations, the processing code executed on the detection data includes a data analysis routine designed to analyze the detection data to determine the locations and metadata of individual analytes visible or encoded in the data, as well as locations at which no analyte is detected (i.e., where there is no analyte, or where no meaningful signal was detected from an existing analyte). In particular implementations, analyte locations in an array will typically appear brighter than non-analyte locations due to the presence of fluorescing dyes attached to the imaged analytes. It will be understood that the analytes need not appear brighter than their surrounding area, for example, when a target for the probe at the analyte is not present in an array being detected. The color at which individual analytes appear may be a function of the dye employed as well as of the wavelength of the light used by the imaging system for imaging purposes. Analytes to which targets are not bound or that are otherwise devoid of a particular label can be identified according to other characteristics, such as their expected location in the microarray.

Once the data analysis routine has located individual analytes in the data, a value assignment may be carried out. In general, the value assignment will assign a digital value to each analyte based upon characteristics of the data represented by detector components (e.g., pixels) at the corresponding location. That is, for example when imaging data is processed, the value assignment routine may be designed to recognize that a specific color or wavelength of light was detected at a specific location, as indicated by a group or cluster of pixels at the location. In a typical DNA imaging application, for example, the four common nucleotides will be represented by four separate and distinguishable colors. Each color, then, may be assigned a value corresponding to that nucleotide.

As used herein, the terms "module", "system," or "system controller" may include a hardware and/or software system and circuitry that operates to perform one or more functions. For example, a module, system, or system controller may include a computer processor, controller, or other logic-based device that performs operations based on instructions stored on a tangible and non-transitory computer readable storage medium, such as a computer memory. Alternatively, a module, system, or system controller may include a hard-wired device that performs operations based on hard-wired logic and circuitry. The module, system, or system controller shown in the attached figures may represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or computer microprocessors.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are examples only, and are thus not limiting as to the types of memory usable for storage of a computer program.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the implementations of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year, and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some implementations of the methods and systems presented herein can reduce the time, hardware, networking, and laboratory infrastructure requirements needed to produce usable sequence data.

The present disclosure describes various methods and systems for carrying out the methods. Examples of some of the methods are described as a series of steps. However, it should be understood that implementations are not limited to the particular steps and/or order of steps described herein. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other implementations.

In some implementations, a processing unit, processor, module, or computing system that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

Moreover, the operations of the methods described herein can be sufficiently complex such that the operations cannot be mentally performed by an average human being or a person of ordinary skill in the art within a commercially reasonable time period. For example, the methods may rely on relatively complex computations such that such a person cannot complete the methods within a commercially reasonable time.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

As used herein, the term "each", when used in reference to a collection of items, is intended to identify an individual item in the collection but does not necessarily refer to every item in the collection. Exceptions can occur if explicit disclosure or context clearly dictates otherwise.

Although the invention has been described with reference to the examples provided above, it should be understood that various modifications can be made without departing from the invention.

The modules in this application can be implemented in hardware or software, and need not be divided up in precisely the same blocks as shown in the figures. Some can also be implemented on different processors or computers, or spread among a number of different processors or computers. In addition, it will be appreciated that some of the modules can be combined, operated in parallel or in a different sequence than that shown in the figures without affecting the functions achieved. Also as used herein, the term "module" can include "sub-modules", which themselves can be considered herein to constitute modules. The blocks in the figures designated as modules can also be thought of as flowchart steps in a method.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify".

As used herein, a given signal, event or value is "in dependence upon" a predecessor signal, event or value of the predecessor signal, event or value influenced by the given signal, event or value. If there is an intervening processing element, step or time period, the given signal, event or value can still be "in dependence upon" the predecessor signal, event or value. If the intervening processing element or step combines more than one signal, event or value, the signal output of the processing element or step is considered "in dependence upon" each of the signal, event or value inputs. If the given signal, event or value is the same as the predecessor signal, event or value, this is merely a degenerate case in which the given signal, event or value is still considered to be "in dependence upon" or "dependent on" or "based on" the predecessor signal, event or value. "Responsiveness" of a given signal, event or value upon another signal, event or value is defined similarly.

As used herein, "concurrently" or "in parallel" does not require exact simultaneity. It is sufficient if the evaluation of one of the individuals begins before the evaluation of another of the individuals completes.

Computer System

Figure 17:
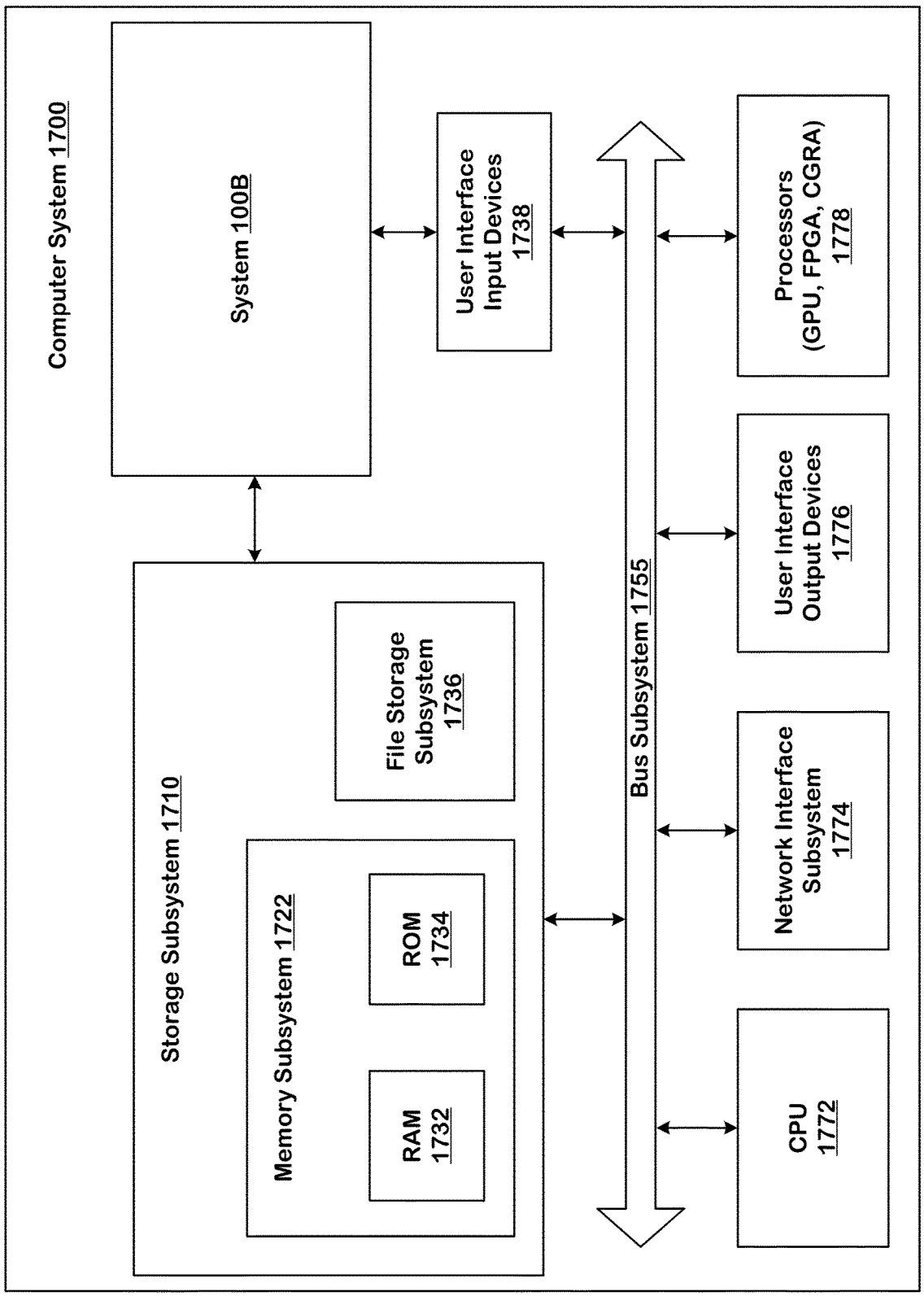
FIG. 17 is a computer system that can be used to implement the technology disclosed.

FIG. 17 is a computer system 1700 that can be used to implement the technology disclosed. Computer system 1700 includes at least one central processing unit (CPU) 1772 that communicates with a number of peripheral devices via bus subsystem 1755. These peripheral devices can include a storage subsystem 1710 including, for example, memory devices and a file storage subsystem 1736, user interface input devices 1738, user interface output devices 1776, and a network interface subsystem 1774. The input and output devices allow user interaction with computer system 1700. Network interface subsystem 1774 provides an interface to outside networks, including an interface to corresponding interface devices in other computer systems.

In one implementation, the equalizer base caller 104 is communicably linked to the storage subsystem 1710 and the user interface input devices 1738.

User interface input devices 1738 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1700.

User interface output devices 1776 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1700 to the user or to another machine or computer system.

Storage subsystem 1710 stores programming and data constructs that provide the functionality of some or all of the modules and methods described herein. These software modules are generally executed by processors 1778.

Processors 1778 can be graphics processing units (GPUs), field-programmable gate arrays (FPGAs), application-specific integrated circuits (ASICs), and/or coarse-grained reconfigurable architectures (CGRAs). Processors 1778 can be hosted by a deep learning cloud platform such as Google Cloud Platform™, Xilinx™, and Cirrascale™. Examples of processors 1778 include Google's Tensor Processing Unit (TPU)™, rackmount solutions like GX4 Rackmount Series™, GX17 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 1722 used in the storage subsystem 1710 can include a number of memories including a main random access memory (RAM) 1732 for storage of instructions and data during program execution and a read only memory (ROM) 1734 in which fixed instructions are stored. A file storage subsystem 1736 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1736 in the storage subsystem 1710, or in other machines accessible by the processor.

Bus subsystem 1755 provides a mechanism for letting the various components and subsystems of computer system 1700 communicate with each other as intended. Although bus subsystem 1755 is shown schematically as a single bus, alternative implementations of the bus subsystem can use multiple busses.

Computer system 1700 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1700 depicted in FIG. 17 is intended only as a specific example for purposes of illustrating the preferred implementations of the present invention. Many other configurations of computer system 1700 are possible having more or less components than the computer system depicted in FIG. 17.

Particular Implementations

The technology disclosed attenuates spatial crosstalk from sensor pixels using equalization-based image processing techniques. The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

In one implementation, the technology disclosed proposes a computer-implemented method of attenuating spatial crosstalk from sensor pixels.

The technology disclosed resolves spatial crosstalk over sensor pixels in a pixel plane caused by periodically distributed fluorescent samples in a sample plane. Signal cones from the fluorescent samples are optically coupled to local grids of the sensor pixels through at least one lens. The signal cones overlap and impinge on the sensor pixels, thereby creating the spatial crosstalk.

The technology disclosed captures in at least one subpixel lookup table a characteristic spread of a characteristic signal cone projected through the lens and resulting contributions of the characteristic signal cone to fluorescence detected by sensor pixels in a local grid of the sensor pixels. The local grid of the sensor pixels is substantially concentric with a center of the characteristic signal cone.

The technology disclosed interpolates among a set of subpixel lookup tables that express the characteristic spread with subpixel resolution to generate an interpolated lookup table based on a target fluorescent sample center.

The technology disclosed isolates a signal from the target fluorescent sample that projects a center of a signal cone onto substantially a center of a target local grid of the sensor pixels by convolving the interpolated lookup table with sensor pixels in the target local grid.

The technology disclosed uses a sum of convolved contributions of the isolated signal as intensity of fluorescence from the target fluorescent sample.

The technology disclosed then base calls the first target fluorescent sample using the intensity of fluorescence. The intensity of fluorescence is determined for the first target fluorescent sample for each imaging channel in a plurality of imaging channels. Consider the four-channel chemistry that generates four images per sequencing cycle using four imaging channels. Then, for the first target fluorescent sample, four intensities of fluorescence are determined using the technology disclosed, as described above. Then, the four intensities of fluorescence are processed by a base caller to base call the first target fluorescent sample. Similarly, for two-channel chemistry, two intensities of fluorescence are used to base call the first target fluorescent sample.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in this method can readily be combined with sets of base features identified as implementations in other sections of this application.

In some implementations, the periodically distributed fluorescent samples are arranged in a diamond shape. In other implementations, the periodically distributed fluorescent samples are arranged in a hexagonal shape.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In another implementation, the technology disclosed proposes a computer-implemented method of base calling.

The technology disclosed accesses an image whose pixels depict intensity emissions from a target cluster and intensity emissions from additional adjacent clusters. The pixels include a center pixel that contains a center of the target cluster. Each pixel in the pixels is divisible into a plurality of subpixels.

Depending upon a particular subpixel, in a plurality of subpixels of the center pixel, which contains the center of the target cluster, the technology disclosed selects, from a bank of subpixel lookup tables, a subpixel lookup table that corresponds to the particular subpixel. The selected subpixel lookup table contains pixel coefficients that are configured to accept the intensity emissions from the target cluster and reject the intensity emissions from the adjacent clusters.

The technology disclosed element-wise multiplies the pixel coefficients to intensity values of the pixels in the image, and sums products of the multiplications to produce an output.

The technology disclosed uses the output to base call the target cluster.

Each of the features discussed in this particular implementation section for other implementations apply equally to this method implementation. As indicated above, all the method features are not repeated here and should be considered repeated by reference.

In some implementations, the technology disclosed further includes (i) selecting additional subpixel lookup tables, from the bank of subpixel look tables, which correspond to subpixels that are most contiguously adjacent to the particular subpixel, (ii) interpolating among pixel coefficients of the selected subpixel lookup table and the selected additional subpixel lookup tables and generating interpolated pixel coefficients that are configured to accept the intensity emissions from the target cluster and reject the intensity emissions from the adjacent clusters, (iii) element-wise multiplying the interpolated pixel coefficients to the intensity values of the pixels in the image and summing products of the multiplications to produce an output, and (iv) using the output to base call the target cluster.

In some implementations, the target cluster and the additional adjacent clusters are periodically distributed on a flow cell in a diamond shape and immobilized on wells of the flow cell. In other implementations, the target cluster and the additional adjacent clusters are periodically distributed on the flow cell in a hexagonal shape and immobilized on wells of the flow cell.

In some implementations, the interpolating is based on at least one of linear interpolation, bilinear interpolation, and bicubic interpolation.

In some implementations, pixel coefficients of subpixel lookup tables in the bank of subpixel lookup tables are learned as a result of training an equalizer using decision-directed equalization. In one implementation, the decision-directed equalization uses least square estimation as a loss function. In one implementation, the least square estimation minimizes a squared error using ground truth base calls. In one implementation, the ground truth base calls are modified to account for DC offset, amplification coefficient, and degree of polyclonality.

In some implementations, pixel coefficients of subpixel lookup tables in the bank of subpixel lookup tables are derived from a combination of (i) a single subpixel lookup table whose pixel coefficients are learned as a result of training an equalizer using decision-directed equalization, and (ii) a precalculated set of interpolation filters. Each interpolation filter in the set of interpolation filters respectively corresponds to each subpixel in the plurality of subpixels.

The technology disclosed further includes making the center of the target cluster substantially concentric with a center of the center pixel by (i) registering the image against a template image and determining affine transformation and nonlinear transformation parameters, (ii) using the parameters to transform location coordinates of the target cluster and the additional adjacent clusters to image coordinates of the image and generating a transformed image with transformed pixels, and (iii) applying interpolation using the transformed location coordinates of the target cluster and the additional adjacent clusters to make their respective cluster centers substantially concentric with centers of respective transformed pixels that contain the cluster centers.

The technology disclosed further includes producing the output for each image in a plurality of images captured using respective imaging channels at a particular sequencing cycle, and base calling the target cluster using the output respectively produced for each image.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose the following clauses:

1. A computer-implemented method of base calling, the method including:

accessing an image whose pixels depict intensity emissions from a target cluster and intensity emissions from additional adjacent clusters, the pixels including a center pixel that contains a center of the target cluster, and each pixel in the pixels divisible into a plurality of subpixels;

depending upon a particular subpixel, in a plurality of subpixels of the center pixel, which contains the center of the target cluster, selecting, from a bank of subpixel lookup tables, a subpixel lookup table that corresponds to the particular subpixel, the selected subpixel lookup table containing pixel coefficients that are configured to maximize a signal-to-noise ratio;

element-wise multiplying the pixel coefficients to intensity values of the pixels in the image and summing products of the multiplications to produce an output, the pixel coefficients serving as weights and the output being a weighted sum of the intensity values; and using the output to base call the target cluster.

2. The computer-implemented method of clause 1, wherein the signal maximized in the signal-to-noise ratio is the intensity emissions from the target cluster, and the noise minimized in the signal-to-noise ratio is the intensity emissions from the adjacent clusters.

3. The computer-implemented method of clause 1, wherein the element-wise multiplication adds a bias for given set of equalizer coefficients.

4. The computer-implemented method of clause 3, wherein the bias is a DC offset that averages background noise intensity.

5. The computer-implemented method of clause 1, further including:
  selecting additional subpixel lookup tables, from the bank of subpixel look tables, which correspond to subpixels that are most contiguously adjacent to the particular subpixel;
  interpolating among pixel coefficients of the selected subpixel lookup table and the selected additional subpixel lookup tables and generating interpolated pixel coefficients that are configured to maximize the signal-to-noise ratio;
  element-wise multiplying the interpolated pixel coefficients to the intensity values of the pixels in the image and summing products of the multiplications to produce an output, the interpolated pixel coefficients serving as weights and the output being a weighted sum of the intensity values; and
  using the output to base call the target cluster.

6. The computer-implemented method of clause 1, wherein the target cluster and the additional adjacent clusters are periodically distributed on a flow cell in a diamond shape and immobilized on wells of the flow cell.

7. The computer-implemented method of clause 6, wherein the target cluster and the additional adjacent clusters are periodically distributed on the flow cell in a hexagonal shape and immobilized on wells of the flow cell.

8. The computer-implemented method of clause 1, wherein the interpolating is based on at least one of linear interpolation, bilinear interpolation, and bicubic interpolation.

9. The computer-implemented method of clause 1, wherein pixel coefficients of subpixel lookup tables in the bank of subpixel lookup tables are learned as a result of training an equalizer using at least one of least squares estimation, ordinary least squares, least-mean squares, and recursive least-squares. In other implementations, other estimation algorithms and adaptive algorithms can be used to train the equalizer.

10. The computer-implemented method of clause 9, further including training the equalizer in an offline mode in which the pixel coefficients of subpixel lookup tables are fixed after being trained on batches of training data from a previously executed sequencing run.

11. The computer-implemented method of clause 10, further including training the equalizer in an online mode in which the pixel coefficients of subpixel lookup tables are iteratively updated as training data from an ongoing sequencing run becomes available.

12. The computer-implemented method of clause 11, further including accessing base-wise intensity distributions of each of the four bases A, C, G, and T generated during prior base calling of images in the training data, selecting respective centers of the base-wise intensity distributions as base-wise ground truth target intensities, and using the base-wise ground truth target intensities to train the equalizer.

13. The computer-implemented method of clause 12, further including pre-training the equalizer in the offline mode and retraining the equalizer in the online mode.

14. The computer-implemented method of clause 9, further including generating the lookup tables in the bank of subpixel lookup tables by together applying a single set of equalizer coefficients and a precalculated set of interpolation filters, including interpolating pixel intensities to generate inputs for the equalizer. This includes calculating pixel weights for clusters that have a substantially different alignment with respect to pixels compared to the trained equalizer coefficients, by using interpolated pixel intensity values to generate the equalizer inputs. Interpolation and equalizer filter responses can be convolved together for an efficient implementation with a single shared LUT. In other implementations, the interpolation filter calculation can be done directly, without binning to subpixels.

15. The computer-implemented method of clause 1, further including making the center of the target cluster substantially concentric with a center of the center pixel by:
  registering the image against a template image and determining affine transformation and nonlinear transformation parameters;
  using the parameters to transform location coordinates of the target cluster and the additional adjacent clusters to image coordinates of the image and generating a transformed image with transformed pixels; and
  applying interpolation using the transformed location coordinates of the target cluster and the additional adjacent clusters to make their respective cluster centers substantially concentric with centers of respective transformed pixels that contain the cluster centers.

16. The computer-implemented method of clause 4, further including producing the output for each image in a plurality of images captured using respective imaging channels and/or color channels at a particular sequencing cycle, and base calling the target cluster using the output respectively produced for each image.

17. A computer-implemented method of recovering an underlying signal from a fluorescent sample positioned in a sample plane from a signal that is corrupted by surrounding fluorescent sources also in the sample plane, the method including:
  capturing in at least one subpixel lookup table a characteristic collection of illumination in an image plane by a sensor pixel array based on sampling that takes into account corruption from the surrounding fluorescent sources and then generating a set of lookup tables for the characteristic collection of illumination by the sensor pixel array when a center coordinate of the fluorescent sample is at positions distributed over a center pixel of the sensor array, the positions distributed relative to a center of coordinate of the center pixel;
  receiving an image that has the center coordinate of the fluorescent sample somewhere in the center pixel of the sensor pixel array, wherein the image is corrupted by the surrounding fluorescent sources, and receiving the center coordinate of the fluorescent sample within the center pixel;
  calculating an interpolated table of characteristic collection of illumination by a sensor pixel array customized to the received center coordinate of the fluorescent sample based on interpolating between lookup tables in the set of lookup table;
  recovering a signal from the target fluorescent sample that projects a center of a signal cone onto substantially a center of a target local grid of the sensor pixels by element-wise multiplying the interpolated lookup table with sensor pixels in the target local grid;
  using a sum of products of the element-wise multiplications as intensity of fluorescence from the target fluorescent sample; and
  base calling the first target fluorescent sample using the intensity of fluorescence.

1. A computer-implemented method of base calling, the method including:

accessing an image whose pixels depict intensity emissions from a target cluster and intensity emissions from additional adjacent clusters;

selecting a lookup table that contains pixel coefficients that are configured to maximize a signal-to-noise ratio;

convolving the pixel coefficients with intensity values of the pixels in the image to produce an output; and base calling the target cluster based on the output.

2. The computer-implemented method of claim 1, wherein the signal maximized in the signal-to-noise ratio is the intensity emissions from the target cluster, and the noise minimized in the signal-to-noise ratio is the intensity emissions from the adjacent clusters, plus additional noise sources.

3. The computer-implemented method of claim 1, wherein the pixels include a center pixel that contains a center of the target cluster, and each pixel in the pixels is divisible into a plurality of sub pixels.

4. The computer-implemented method of claim 3, wherein the lookup table is a subpixel lookup table.

5. The computer-implemented method of claim 4, further including:

depending upon a particular subpixel, in a plurality of subpixels of the center pixel, which contains the center of the target cluster, selecting, from a bank of subpixel lookup tables, the subpixel lookup table that corresponds to the particular subpixel, the selected subpixel lookup table containing the pixel coefficients;

element-wise multiplying the pixel coefficients to the intensity values of the pixels in the image and summing products of the multiplications to produce the output, the pixel coefficients serving as weights and the output being a weighted sum of the intensity values; and using the output to base call the target cluster, including generating the output for each imaging channel in a plurality of imaging channels and base calling the target cluster using the output for each imaging channel.

6. The computer-implemented method of claim 5, wherein the element-wise multiplication adds a bias for given set of equalizer coefficients, wherein the bias is a DC offset that averages background noise intensity.

7. The computer-implemented method of claim 5, further including:

selecting additional subpixel lookup tables, from the bank of subpixel look tables, which correspond to subpixels that are contiguously adjacent to the particular subpixel;

generating, based on pixel coefficients of the selected subpixel lookup table and the selected additional subpixel lookup tables, interpolated pixel coefficients that are configured to maximize the signal-to-noise ratio;

convolving the interpolated pixel coefficients with the intensity values of the pixels in the image to produce an output; and base calling the target cluster based on the output.

8. The computer-implemented method of claim 7, further including:

element-wise multiplying the interpolated pixel coefficients to the intensity values of the pixels in the image and summing products of the multiplications to produce the output, the interpolated pixel coefficients serving as weights and the output being a weighted sum of the intensity values.

9. The computer-implemented method of claim 1, further including training an equalizer using at least one of least squares estimation, ordinary least squares, least-mean squares, and recursive least-squares to generate the pixel coefficients.

10. The computer-implemented method of claim 9, further including training the equalizer in an offline mode in which the pixel coefficients of subpixel lookup tables are fixed after being trained on batches of training data from a previously executed sequencing run.

11. The computer-implemented method of claim 10, further including training the equalizer in an online mode in which the pixel coefficients of subpixel lookup tables are iteratively updated during an ongoing sequencing run.

12. The computer-implemented method of claim 11, further including accessing base-wise intensity distributions of each of the four bases A, C, G, and T generated during prior base calling of images in the training data, selecting respective centers of the base-wise intensity distributions as base-wise ground truth target intensities for corresponding color channels, and using the base-wise ground truth target intensities to train the equalizer.

13. The computer-implemented method of claim 12, further including pre-training the equalizer in the offline mode and retraining the equalizer in the online mode.

14. The computer-implemented method of claim 9, further including generating the lookup tables in the bank of subpixel lookup tables by together applying a single set of equalizer coefficients and a precalculated set of interpolation filters, including interpolating pixel intensities to generate inputs for the equalizer.

15. The computer-implemented method of claim 1, further including making the center of the target cluster concentric with a center of the center pixel by:

registering the image against a template image and determining affine transformation and nonlinear transformation parameters;

using the parameters to transform location coordinates of the target cluster and the additional adjacent clusters to image coordinates of the image and generating a transformed image with transformed pixels; and applying interpolation using the transformed location coordinates of the target cluster and the additional adjacent clusters to make their respective cluster centers concentric with centers of respective transformed pixels that contain the cluster centers.

16. A non-transitory computer readable storage medium impressed with computer program instructions to perform base calling, the instructions, when executed on a processor, implement a method comprising:

accessing an image whose pixels depict intensity emissions from a target cluster and intensity emissions from additional adjacent clusters;

selecting a lookup table that contains pixel coefficients that are configured to maximize a signal-to-noise ratio;

convolving the pixel coefficients with intensity values of the pixels in the image to produce an output; and base calling the target cluster based on the output.

17. The non-transitory computer readable storage medium of claim 16, wherein the signal maximized in the signal-to-noise ratio is the intensity emissions from the target cluster, and the noise minimized in the signal-to-noise ratio is the intensity emissions from the adjacent clusters, plus additional noise sources.

18. The non-transitory computer readable storage medium of claim 16, implementing the method further comprising training an equalizer using at least one of least squares estimation, ordinary least squares, least-mean squares, and recursive least-squares to generate the pixel coefficients.

19. A system including one or more processors coupled to memory, the memory loaded with computer instructions to perform base calling, the instructions, when executed on the processors, implement actions comprising:

accessing an image whose pixels depict intensity emissions from a target cluster and intensity emissions from additional adjacent clusters;

selecting a lookup table that contains pixel coefficients that are configured to maximize a signal-to-noise ratio;

convolving the pixel coefficients with intensity values of the pixels in the image to produce an output; and base calling the target cluster based on the output.

20. The system of claim 19, further implementing actions comprising training an equalizer using at least one of least squares estimation, ordinary least squares, least-mean squares, and recursive least-squares to generate the pixel coefficients.

While the present invention is disclosed by reference to the preferred implementations and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A computer-implemented method of base calling, the method including:

accessing an image whose pixels depict intensity emissions from a target cluster and intensity emissions from additional adjacent clusters;

selecting a lookup table that contains pixel coefficients that are configured to maximize a signal-to-noise ratio;

convolving the pixel coefficients with intensity values of the pixels in the image to produce an output; and base calling the target cluster based on the output.

2. The computer-implemented method of claim 1, wherein the signal maximized in the signal-to-noise ratio is the intensity emissions from the target cluster, and the noise minimized in the signal-to-noise ratio is the intensity emissions from the adjacent clusters, plus additional noise sources.

3. The computer-implemented method of claim 1, wherein the pixels include a center pixel that contains a center of the target cluster, and each pixel in the pixels is divisible into a plurality of sub pixels.

4. The computer-implemented method of claim 3, wherein the lookup table is a subpixel lookup table.

5. The computer-implemented method of claim 4, further including:

depending upon a particular subpixel, in a plurality of subpixels of the center pixel, which contains the center of the target cluster, selecting, from a bank of subpixel lookup tables, the subpixel lookup table that corresponds to the particular subpixel, the selected subpixel lookup table containing the pixel coefficients;

element-wise multiplying the pixel coefficients to the intensity values of the pixels in the image and summing products of the multiplications to produce the output, the pixel coefficients serving as weights and the output being a weighted sum of the intensity values; and using the output to base call the target cluster, including generating the output for each imaging channel in a plurality of imaging channels and base calling the target cluster using the output for each imaging channel.

6. The computer-implemented method of claim 5, wherein the element-wise multiplication adds a bias for given set of equalizer coefficients, wherein the bias is a DC offset that averages background noise intensity.

7. The computer-implemented method of claim 5, further including:

selecting additional subpixel lookup tables, from the bank of subpixel look tables, which correspond to subpixels that are contiguously adjacent to the particular subpixel;

generating, based on pixel coefficients of the selected subpixel lookup table and the selected additional subpixel lookup tables, interpolated pixel coefficients that are configured to maximize the signal-to-noise ratio;

convolving the interpolated pixel coefficients with the intensity values of the pixels in the image to produce an output; and base calling the target cluster based on the output.

8. The computer-implemented method of claim 7, further including:

element-wise multiplying the interpolated pixel coefficients to the intensity values of the pixels in the image and summing products of the multiplications to produce the output, the interpolated pixel coefficients serving as weights and the output being a weighted sum of the intensity values.

9. The computer-implemented method of claim 1, further including training an equalizer using at least one of least squares estimation, ordinary least squares, least-mean squares, and recursive least-squares to generate the pixel coefficients.

10. The computer-implemented method of claim 9, further including training the equalizer in an offline mode in which the pixel coefficients of subpixel lookup tables are fixed after being trained on batches of training data from a previously executed sequencing run.

11. The computer-implemented method of claim 10, further including training the equalizer in an online mode in which the pixel coefficients of subpixel lookup tables are iteratively updated during an ongoing sequencing run.

12. The computer-implemented method of claim 11, further including accessing base-wise intensity distributions of each of the four bases A, C, G, and T generated during prior base calling of images in the training data, selecting respective centers of the base-wise intensity distributions as base-wise ground truth target intensities for corresponding color channels, and using the base-wise ground truth target intensities to train the equalizer.

13. The computer-implemented method of claim 12, further including pre-training the equalizer in the offline mode and retraining the equalizer in the online mode.

14. The computer-implemented method of claim 9, further including generating the lookup tables in the bank of subpixel lookup tables by together applying a single set of equalizer coefficients and a precalculated set of interpolation filters, including interpolating pixel intensities to generate inputs for the equalizer.

15. The computer-implemented method of claim 1, further including making the center of the target cluster concentric with a center of the center pixel by:

registering the image against a template image and determining affine transformation and nonlinear transformation parameters;

using the parameters to transform location coordinates of the target cluster and the additional adjacent clusters to image coordinates of the image and generating a transformed image with transformed pixels; and applying interpolation using the transformed location coordinates of the target cluster and the additional adjacent clusters to make their respective cluster centers concentric with centers of respective transformed pixels that contain the cluster centers.

16. A non-transitory computer readable storage medium impressed with computer program instructions to perform base calling, the instructions, when executed on a processor, implement a method comprising:

accessing an image whose pixels depict intensity emissions from a target cluster and intensity emissions from additional adjacent clusters;

selecting a lookup table that contains pixel coefficients that are configured to maximize a signal-to-noise ratio;

convolving the pixel coefficients with intensity values of the pixels in the image to produce an output; and base calling the target cluster based on the output.

17. The non-transitory computer readable storage medium of claim 16, wherein the signal maximized in the signal-to-noise ratio is the intensity emissions from the target cluster, and the noise minimized in the signal-to-noise ratio is the intensity emissions from the adjacent clusters, plus additional noise sources.

18. The non-transitory computer readable storage medium of claim 16, implementing the method further comprising training an equalizer using at least one of least squares estimation, ordinary least squares, least-mean squares, and recursive least-squares to generate the pixel coefficients.

19. A system including one or more processors coupled to memory, the memory loaded with computer instructions to perform base calling, the instructions, when executed on the processors, implement actions comprising:

accessing an image whose pixels depict intensity emissions from a target cluster and intensity emissions from additional adjacent clusters;

selecting a lookup table that contains pixel coefficients that are configured to maximize a signal-to-noise ratio;

convolving the pixel coefficients with intensity values of the pixels in the image to produce an output; and base calling the target cluster based on the output.

20. The system of claim 19, further implementing actions comprising training an equalizer using at least one of least squares estimation, ordinary least squares, least-mean squares, and recursive least-squares to generate the pixel coefficients.

* * * * *

UNITED STATES PATENT AND TRADEMARK OFFICE
CERTIFICATE OF CORRECTION

| | | |
|---|---|---|
| PATENT NO. | : 11,188,778 B1 | Page 1 of 1 |
| APPLICATION NO. | : 17/308035 | |
| DATED | : November 30, 2021 | |
| INVENTOR(S) | : Ojard et al. | |

It is certified that error appears in the above-identified patent and that said Letters Patent is hereby corrected as shown below:

In the Claims

In Claim 7, at Column 56, Line 8, delete the word "look" and insert the word --lookup--.

Signed and Sealed this
Fifteenth Day of August, 2023

*Katherine Kelly Vidal*

Katherine Kelly Vidal
*Director of the United States Patent and Trademark Office*